(12) United States Patent
Jadhav et al.

(10) Patent No.: US 6,214,834 B1
(45) Date of Patent: Apr. 10, 2001

(54) INTEGRIN INHIBITOR PRODRUGS

(75) Inventors: Prabhakar K. Jadhav; Douglas G. Batt; Munir A. Hussain, all of Wilmington; William J. Pitts, Newark; Arnold J. Repta, Wilmington, all of DE (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/049,305

(22) Filed: Mar. 27, 1998

Related U.S. Application Data

(60) Provisional application No. 60/041,759, filed on Mar. 28, 1997.

(51) Int. Cl.[7] .................... C07D 231/56; A61K 31/416
(52) U.S. Cl. .................... 514/275; 514/338; 514/397; 514/406; 514/407; 544/331; 546/275.7; 548/311.7; 548/312.1; 548/361.5; 548/362.1; 548/362.5
(58) Field of Search ..................... 514/275, 338, 514/397, 406, 407; 544/331; 546/275.7; 548/311.7, 312.1, 361.5, 362.1, 362.5

(56) References Cited

U.S. PATENT DOCUMENTS 5,629,322   5/1997   Guthikonda et al. ............... 514/313

FOREIGN PATENT DOCUMENTS

| | | |
|---|---|---|
| 0655439 | 5/1995 | (EP) . |
| WO9418981 | 9/1994 | (WO) . |
| WO9514682 | 6/1995 | (WO) . |
| WO9514683 | 6/1995 | (WO) . |
| WO9528145 | 10/1995 | (WO) . |
| WO9600730 | 1/1996 | (WO) . |
| WO9620192 | 7/1996 | (WO) . |
| WO9637492 | 11/1996 | (WO) . |
| WO9638426 | 12/1996 | (WO) . |
| WO9723480 | 7/1997 | (WO) . |
| WO9733887 | 9/1997 | (WO) . |
| WO9748395 | 12/1997 | (WO) . |

OTHER PUBLICATIONS

Bundgaard, H., "Design of Prodrugs", *Elsevier Science*, 1985, pp. 1–10.

Zhang et al., The Chiral Specific Synthesis of DMP 754, a Platelet GP IIb/IIIa Antagonist, *Tetrahedron Lett.*, vol. 37, No. 26 (1996), pp. 4455–4458.

*Primary Examiner*—Mukund J. Shah
*Assistant Examiner*—Deepak R. Rao

(57) ABSTRACT

This invention relates to novel heterocycles which are useful as antagonists of the $\alpha_v\beta_3$ integrin and related cell surface adhesive protein receptors, to pharmaceutical compositions containing such compounds, to iontophoretic delivery of such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

42 Claims, No Drawings

INTEGRIN INHIBITOR PRODRUGS

This application claims the benefit of U.S. Provisional Application No. 60/041,759, filed Mar. 28, 1997.

FIELD OF THE INVENTION

This invention relates to novel heterocycles which are useful as antagonists of the $\alpha_v\beta_3$ integrin and related cell surface adhesive protein receptors, to pharmaceutical compositions containing such compounds, to iontophoretic delivery of such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

BACKGROUND OF THE INVENTION

Angiogenesis or neovascularization is critical for normal physiological processes such as embryonic development and wound repair (Folkman and Shing, J. Biol. Chem. 1992, 267:10931–10934; D'Amore and Thompson, Ann. Rev. Physiol. 1987, 49:453–464). However, angiogenesis also occurs pathologically, for example, in ocular neovascularization (leading to diabetic retinopathy, neovascular glaucoma, retinal vein occlusion and blindness), in rheumatoid arthritis and in solid tumors (Folkman and Shing, J. Biol. Chem., 1992, 267:10931–10934; Blood and Zetter, Biochim. Biophys. Acta., 1990, 1032:118–128).

Tumor dissemination, or metastasis, involves several distinct and complementary components, including the penetration and traversing of tumor cells through basement membranes and the establishment of self-sustaining tumor foci in diverse organ systems. To this end, angiogenesis is critical to tumor survival. Without neovascularization, tumor cells lack the nourishment to divide and will not be able to leave the primary tumor site (Folkman and Shing, J. Biol. Chem., 1992, 267:10931–10934).

Inhibition of angiogenesis in animal models of cancer has been shown to result in tumor growth suppression and prevention of metastatic growth (Herblin et al., Exp. Opin. Ther. Patents, 1994, 1–14). Many angiogenic inhibitors have been directed toward blocking initial cytokine-dependent induction of new vessel growth, e.g. antibodies to endothelial cell growth factors. However, these approaches are problematic because tumor and inflammatory cells can secrete multiple activators of angiogenesis (Brooks et al., Cell, 1994, 79:1157–1164). Therefore, a more general approach that would allow inhibition of angiogenesis due to a variety of stimuli would be of benefit.

The integrin $\alpha_v\beta_3$, sometimes called the vitronectin receptor, is preferentially expressed on angiogenic blood vessels in chick and man (Brooks et al., Science, 1994, 264:569–571; Enenstein and Kramer, J. Invest. Dermatol., 1994, 103:381–386). $\alpha_v\beta_3$ is the most promiscuous member of the integrin family, allowing endothelial cells to interact with a wide variety of extracellular matrix components (Hynes, Cell, 1992, 69:11–25). These adhesive interactions are considered to be critical for angiogenesis since vascular cells must ultimately be capable of invading virtually all tissues.

While integrin $\alpha_v\beta_3$ promotes adhesive events important for angiogenesis, this receptor also transmits signals from the extracellular environment to the intracellular compartment (Leavesley et al., J. Cell Biol., 1993, 121:163–170, 1993). For example, the interaction between the $\alpha_v\beta_3$ integrin and extracellular matrix components promotes a calcium signal required for cell motility.

During endothelium injury, the basement membrane zones of blood vessels express several adhesive proteins, including but not limited to von Willebrand factor, fibronectin, and fibrin. Additionally, several members of the integrin family of adhesion receptors are expressed on the surface of endothelial, smooth muscle and on other circulating cells. Among these integrins is $\alpha_v\beta_3$, the endothelial cell, fibroblast, and smooth muscle cell receptor for adhesive proteins including von Willebrand factor, fibrinogen (fibrin), vitronectin, thrombospondin, and osteopontin. These integrins initiate a calcium-dependent signaling pathway that can lead to endothelial cell and smooth muscle cell migration and, therefore, may play a fundamental role in vascular cell biology.

Recently, an antibody to the $\alpha_v\beta_3$ integrin has been developed that inhibits the interaction of this integrin with agonists such as vitronectin (Brooks et al., Science, 1994, 264:569–571). Application of this antibody has been shown to disrupt ongoing angiogenesis on the chick chorioallantoic membrane (CAM), leading to rapid regression of histologically distinct human tumor transplanted onto the CAM (Brooks et al., Cell, 1994, 79:1157–1164). In this model, antagonists of the $\alpha_v\beta_3$ integrin induced apoptosis of the proliferating angiogenic vascular cells, leaving pre-existing quiescent blood vessels unaffected. Thus, $\alpha_v\beta_3$ integrin antagonists have been shown to inhibit angiogenesis and are recognized as being useful as therapeutic agents for the treatment of human diseases such as cancer, restenosis, thromboembolic disorders, rheumatoid arthritis and ocular vasculopathies (Folkman and Shing, J. Biol. Chem., 1992, 267:10931–10934).

Increasing numbers of other cell surface receptors have been identified which bind to extracellular matrix ligands or other cell adhesion ligands thereby mediating cell-cell and cell-matrix adhesion processes. Like the $\alpha_v\beta_3$ integrin, these receptors belong to the integrin gene superfamily and are composed of heterodimeric transmembrane glycoproteins containing $\alpha$- and $\beta$-subunits. Integrin subfamilies contain a common $\beta$-subunit combined with different $\alpha$-subunits to form adhesion receptors with unique specificity. The genes for eight distinct $\beta$-subunits have been cloned and sequenced to date.

The integrin $\alpha_v\beta_3$ is a member of the $\beta_3$ integrin subfamily and has been described on platelets, endothelial cells, melanoma, smooth muscle cells, and osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like the major platelet integrin GPIIb/IIIa, the vitronectin receptor binds a variety of RGD-containing adhesive proteins such as vitronectin, fibronectin, von Willibrand factor, fibrinogen, osteopontin, bone sialoprotein II and thrombospondin in a manner mediated by the RGD sequence.

A key event in bone resorption is the adhesion of osteoclasts to the matrix of bone. Studies with monoclonal antibodies have implicated the $\alpha_v\beta_3$ receptor in this process and suggest that a selective $\alpha_v\beta_3$ antagonist would have utility in blocking bone resorption in diseases such as osteoporosis (Horton et al., J. Bone Miner. Res., 1993, 8:239–247; Helfrich et al., J. Bone Miner. Res., 1992, 7:335–343).

The use of iontophoresis, also referred to as electrotransport, in drug delivery is well known. Controlled, continuous delivery of drugs at constant rates is a highly useful method of delivering medications. This kind of delivery ensures relatively constant plasma concentrations and, more importantly, proper control of pharmacologic and toxic drug effect. Transdermal delivery can be an especially useful means of controlled, continuous delivery of drugs that exhibit no/low oral bioavailability while avoiding the inconvenience and discomfort of administration by injection. However, most drugs do not diffuse through the skin at rates sufficient for delivering therapeutic doses. Skin is specially impermeable to polar and ionic drugs. The transdermal administration of drugs for which the skin is normally impermeable requires utilizing techniques for enhancing the skin permeation of the drug. One of these techniques is iontophoresis. In order to deliver molecules across the skin in adequate quantity, it must have a net charge. However, we found that sometimes even if the molecule has a net charge, it cannot be delivered effectively iontophoretically due to other physical chemical characteristics, such as surface activity and relatively high partition coefficient which can result in low delivery rate. This invention is related to the iontophoretic delivery of $\alpha_v\beta_3$ antagonists through special prodrugs that provide relatively high delivery rates.

$\alpha_v\beta_3$ receptor antagonists typically have very low/no oral bioavailability and short plasma half-life which make them poor candidates for oral delivery. Controlled delivery systems that administer these compounds or suitable prodrugs of these compounds at constant rate can produce plasma concentrations that would be maintained in the desired range.

This invention relates to novel methods and devices for iontophoretically administering therapeutic doses of integrin receptor antagonists in a controlled manner through the skin. Alkyl esters of the $\alpha_v\beta_3$ integrin inhibitors cannot be delivered efficiently through transdermal iontophoresis because they exhibit high surface activity and self-association. Prodrugs that carry an amine or ammonium functional group on the promoiety provide minimal self-association and high transdermal iontophoretic flux.

SUMMARY OF THE INVENTION

The present invention provides amine/ammonium prodrugs to novel nonpeptide compounds which bind to integrin receptors thereby altering cell-matrix and cell-cell adhesion processes. The prodrugs of the present invention result in compounds useful for the inhibition of cell adhesion and the treatment (including prevention) of angiogenic disorders, inflammation, bone degradation, cancer metastases, diabetic retinopathy, thrombosis, restenosis, macular degeneration, and other conditions mediated by cell adhesion and/or cell migration and/or angiogenesis.

One aspect of this invention provides novel compounds of Formula Ia, Ib, Ic, Id, and Ie (described below) which are prodrugs useful in antagonism of the $\alpha_v\beta_3$ integrin. The $\alpha_v\beta_3$ integrin is also referred to as the $\alpha_v\beta_3$ receptor or the vitronectin receptor. The prodrugs of the present invention result in compounds which inhibit the binding of vitronectin or other RGD-containing ligands to $\alpha_v\beta_3$ and inhibit cell adhesion. The present invention also includes pharmaceutical compositions containing such compounds, and methods of using such compounds for the inhibition of angiogenesis, and/or for the treatment of disorders mediated by angiogenesis. One method of particular importance is the iontophoretic transdermal delivery of the novel prodrug compounds of this invention.

The present invention provides the structural requirements, method and device for the controlled continuous delivery of $\alpha_v\beta_3$ integrin receptor antagonists iontophoretically through skin. It further provides a means of attaining consistent plasma concentration of $\alpha_v\beta_3$ receptor antagonists and for controlling their pharmacologic and toxic effects. More specifically, this invention relates to prodrugs of the zwitterionic form of the drug by derivitizing the carboxyl group with promoiety that carries ammonium/amine functional groups. It is known that zwitterionic compounds do not permeate skin by iontophoresis as extensively as cationic or anionic compounds. Prodrugs are, therefore, used to affect the net charge. These prodrugs are converted to the active zwitterionic compound after transdermal absorption.

Another aspect of the present invention comprises agents that inhibit the binding of vitronectin to the $\alpha_v\beta_3$ receptor for the treatment (including prevention) of thrombosis, which do not significantly alter hemostatic balance and do not significantly inhibit platelet aggregation and do not significantly inhibit coagulation. Also, the compounds of the current invention can be used for the treatment or prevention of restenosis.

The present invention also provides novel compounds, pharmaceutical compositions and methods which may be used in the treatment or prevention of other diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, ocular vasculopathies, inflammatory bowel disease and other autoimmune diseases.

DETAILED DESCRIPTION OF THE INVENTION

The present invention provides novel compounds of Formula Ia, Ib, Ic, Id or Ie (described below) which bind to integrin receptors thereby altering cell-matrix and cell-cell adhesion processes. The compounds of the present invention are useful for the inhibition of cell adhesion and the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis, in a mammal.

One aspect of this invention provides novel compounds of Formula Ia, Ib, Ic, Id or Ie (described below) which are useful as antagonists of the $\alpha_v\beta_3$ integrin. The $\alpha_v\beta_3$ integrin is also referred to as the $\alpha_v\beta_3$ receptor or the vitronectin receptor. The compounds of the present invention inhibit the binding of vitronectin or other RGD-containing ligands to $\alpha_v\beta_3$ and inhibit cell adhesion. The present invention also includes pharmaceutical compositions containing such compounds of Formula Ia, Ib, Ic, Id or Ie, and methods of using such compounds for the inhibition of angiogenesis, and/or for the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis, in a mammal.

[1] One embodiment of the present invention comprises compounds of Formula Ia:

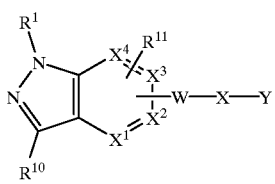

including stereoisomeric forms thereof, or mixtures of stereoisomeric forms thereof, or pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

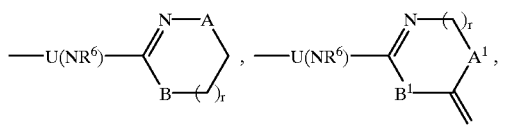

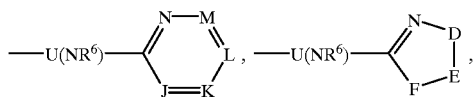

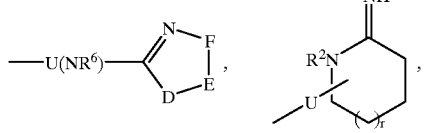

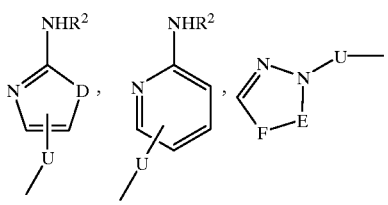

or

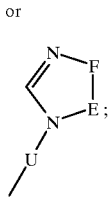

A and B are independently —CH$_2$—, —O—, —N(R$^2$)—, or —C(=O)—;

A$^1$ and B$^1$ are independently —CH$_2$— or —N(R$^3$)—;

D is —N(R$^2$)—, —O—, —S—, —C(=O)— or —SO$_2$—;

E—F is —C(R$^4$)=C(R$^5$)—, —N=C(R$^4$)—, —C(R$^4$)=N—, or —C(R$^4$)$_2$C(R$^5$)$_2$—;

J, K, L and M are independently selected from —C(R$^4$)—, —C(R$^5$)— or —N—, provided that at least one of J, K, L and M is not —N—;

$R^2$ is selected from: H, C$_1$–C$_6$ alkyl, (C$_1$–C$_6$ alkyl)carbonyl, (C$_1$–C$_6$ alkoxy)carbonyl; (C$_1$–C$_6$ alkyl)aminocarbonyl, C$_3$–C$_6$ alkenyl, C$_3$–C$_7$ cycloalkyl, C$_4$–C$_{11}$ cycloalkylalkyl, aryl, heteroaryl(C$_1$–C$_6$ alkyl)carbonyl, heteroarylcarbonyl, aryl(C$_1$–C$_6$ alkyl)-, (C$_1$–C$_6$ alkyl)carbonyl-, arylcarbonyl, C$_1$–C$_6$ alkylsulfonyl, arylsulfonyl, aryl(C$_1$–C$_6$ alkyl)sulfonyl, heteroarylsulfonyl, heteroaryl(C$_1$–C$_6$ alkyl)sulfonyl, aryloxycarbonyl, or aryl(C$_1$–C$_6$ alkoxy)carbonyl, wherein said aryl groups are substituted with 0–2 substituents selected from the group consisting of C$_1$–C$_4$ alkyl, C$_1$–C$_4$ alkoxy, halo, CF$_3$, and nitro;

$R^3$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_1$–C$_6$ alkyl)-;

$R^4$ and $R^5$ are independently selected from: H, C$_1$–C$_4$ alkoxy, NR$^2$R$^3$, halogen, NO$_2$, CN, CF$_3$, C$_1$–C$_6$ alkyl, C$_3$–C$_6$ alkenyl, C$_3$–C$_7$ cycloalkyl, C$_4$–C$_{11}$ cycloalkylalkyl, aryl, aryl(C$_1$–C$_6$ alkyl)-, (C$_1$–C$_6$ alkyl)carbonyl, (C$_1$–C$_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: C$_1$–C$_4$ alkyl, C$_1$–C$_4$ alkoxy, halo, cyano, amino, CF$_3$, or NO$_2$;

U is selected from:
—(CH$_2$)$_n$—,
—(CH$_2$)$_n$(CR$^7$=CR$^8$)(CH$_2$)$_m$—,
—(CH$_2$)$_n$(C≡C)(CH$_2$)$_m$—,
—(CH$_2$)$_t$Q(CH$_2$)$_m$—,
—(CH$_2$)$_n$O(CH$_2$)$_m$—,
—(CH$_2$)$_n$N(R$^6$)(CH$_2$)$_m$—,
—(CH$_2$)$_n$C(=O)(CH$_2$)$_m$—,
—(CH$_2$)$_n$(C=O)N(R$^6$)(CH$_2$)$_m$—
—(CH$_2$)$_n$N(R$^6$)(C=O)(CH$_2$)$_m$—, or
—(CH$_2$)$_n$S(O)$_p$(CH$_2$)$_m$—;
wherein one or more of the methylene groups in U is optionally substituted with R$^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, C$_1$–C$_4$ alkyl, or benzyl;

$R^7$ and $R^8$ are independently selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_0$–C$_6$ alkyl)-;

$R^{10}$ is selected from: H, N(R$^6$)$_2$, halogen, NO$_2$, CN, CF$_3$, CO$_2$R$^{17}$, C(=O)R$^{17}$, CONR$^{17}$R$^{20}$, —SO$_2$R$^{17}$, —SO$_2$NR$^{17}$R$^{20}$, C$_1$–C$_6$ alkyl substituted with 0–1 R$^{15}$ or 0–1 R$^{21}$, C$_1$–C$_4$ alkoxy substituted with 0–1 R$^{21}$, C$_3$–C$_6$ alkenyl substituted with 0–1 R$^{15}$ or 0–1 R$^{21}$, C$_3$–C$_7$ cycloalkyl substituted with 0–1 R$^{15}$ or 0–1 R$^{21}$, C$_4$–C$_{11}$ cycloalkylalkyl substituted with 0–1 R$^{15}$ or 0–1 R$^{21}$, aryl substituted with 0–1 R$^{15}$ or 0–2 R$^{11}$ or 0–1 R$^{21}$, or aryl(C$_1$–C$_6$ alkyl)- substituted with 0–1 R$^{15}$ or 0–2 R$^{11}$ or 0–1 R$^{21}$;

$R^{11}$ is selected from H, halogen, CF$_3$, CN, NO$_2$, hydroxy, NR$^2$R$^3$, C$_1$–C$_4$ alkyl substituted with 0–1 R$^{21}$, C$_1$–C$_4$ alkoxy substituted with 0–1 R$^{21}$, aryl substituted with 0–1 R$^{21}$, aryl(C$_1$–C$_6$ alkyl)- substituted with 0–1 R$^{21}$, (C$_1$–C$_4$ alkoxy)carbonyl substituted with 0–1 R$^{21}$, (C$_1$–C$_4$ alkyl)carbonyl substituted with 0–1 R$^{21}$, C$_1$–C$_4$ alkylsulfonyl substituted with 0–1 R$^{21}$, or C$_1$–C$_4$ alkylaminosulfonyl substituted with 0–1 R$^{21}$;

W is selected from:
—(C(R$^{12}$)$_2$)$_q$C(=O)N(R$^{13}$)—, or
—C(=O) —N(R$^{13}$)—(C(R$^{12}$)$_2$)$_q$—;

X is —C(R$^{12}$)(R$^{14}$)—C(R$^{12}$)(R$^{15}$)—; or alternatively, W and X can be taken together to be

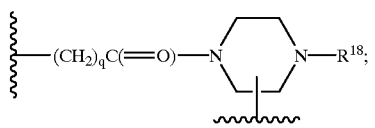

$R^{12}$ is selected from H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl ($C_1$–$C_6$ alkyl)-;

$R^{13}$ is selected from H, $C_1$–$C_6$ alkyl, $C_3$–$C_7$ cycloalkylmethyl, or aryl($C_1$–$C_6$ alkyl)-;

$R^{14}$ is selected from: H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl ($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R_{17}$, $C(=O)R_{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is —$COR^{19}$;

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R^{17}$, or
—$N(R^{20})SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from: H, $C_1$–$C_9$ alkyl, $C_4$–$C_{11}$ cycloalkylalkyl, aryl, aryl($C_1$–$C_6$ alkyl), heteroaryl, heteroaryl($C_1$–$C_6$ alkyl) wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl);

$R^{21}$ is selected from: COOH or $NR^6_2$;

k is 2, 3, 4, 5, or 6;
m is 0, 1, 2, 3, or 4;
n is 0, 1, 2, 3, or 4;
t is 0, 1, 2, 3, or 4;
p is 0, 1, or 2;
q is 0, 1, or 2; and
r is 0, 1, or 2;

with the following provisos:
(1) t, n, m and q are chosen such that the number of atoms connecting $R^1$ and Y is in the range of 10–14; and
(2) n and m are chosen such that the value of n plus m is greater than one unless U is —$(CH_2)_tQ(CH_2)_m$—.

[2] Preferred compounds of the invention as described above are compounds of the Formula Ia:

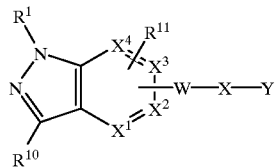

Ia including stereoisomeric forms thereof, or mixtures of stereoisomeric forms thereof, or pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

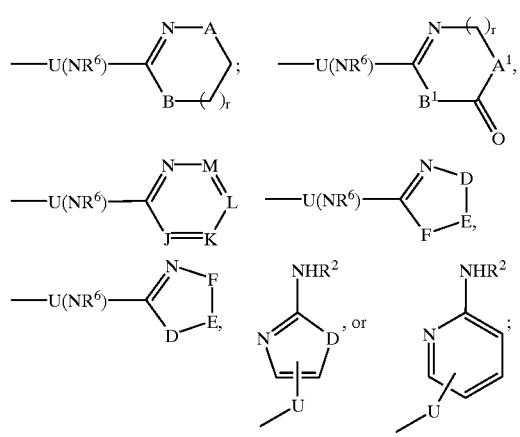

A and B are independently —$CH_2$—, —O—, —$N(R^2)$—, or —$C(=O)$—;
$A^1$ and $B^1$ are independently —$CH_2$— or —$N(R^3)$—;
D is —$N(R^2)$—, —O—, —S—, —$C(=O)$— or —$SO_2$—;
E—F is —$C(R^4)=C(R^5)$—, —$N=C(R^4)$—, —$C(R^4)=N$—, or —$C(R^4)_2C(R^5)_2$—;

J, K, L and M are independently selected from —C(R$^4$)—, —C(R$^5$)— or —N—, provided that at least one of J, K, L and M is not —N—;

R$^2$ is selected from: H, C$_1$–C$_6$ alkyl, (C$_1$–C$_6$ alkyl)carbonyl, (C$_1$–C$_6$ alkoxy)carbonyl, C$_1$–C$_6$ alkylaminocarbonyl, C$_3$–C$_6$ alkenyl, C$_3$–C$_7$ cycloalkyl, C$_4$–C$_{11}$ cycloalkylalkyl, aryl, heteroaryl (C$_1$–C$_6$ alkyl)carbonyl, heteroarylcarbonyl, aryl (C$_1$–C$_6$ alkyl)-, (C$_1$–C$_6$ alkyl)carbonyl, arylcarbonyl, alkylsulfonyl, arylsulfonyl, aryl(C$_1$–C$_6$ alkyl)sulfonyl, heteroarylsulfonyl, heteroaryl(C$_1$–C$_6$ alkyl)sulfonyl, aryloxycarbonyl, or aryl(C$_1$–C$_6$ alkoxy)carbonyl, wherein said aryl groups are substituted with 0–2 substituents selected from the group consisting of C$_1$–C$_4$ alkyl, C$_1$–C$_4$ alkoxy, halo, CF$_3$, and nitro;

R$^3$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_1$–C$_6$ alkyl)-;

R$^4$ and R$^5$ are independently selected from: H, C$_1$–C$_4$ alkoxy, NR$^2$R$^3$, halogen, NO$_2$, CN, CF$_3$, C$_1$–C$_6$ alkyl, C$_3$–C$_6$ alkenyl, C$_3$–C$_7$ cycloalkyl, C$_4$–C$_{11}$ cycloalkylalkyl, aryl, aryl(C$_1$–C$_6$ alkyl)-, C$_2$–C$_7$ alkylcarbonyl, arylcarbonyl or alternatively, when substituents on adjacent atoms, R$^4$ and R$^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: C$_1$–C$_4$ alkyl, C$_1$–C$_4$ alkoxy, halo, cyano, amino, CF$_3$, or NO$_2$;

U is selected from:
 —(CH$_2$)$_n$—,
 —(CH$_2$)$_n$(CR$^7$=CR$^8$)(CH$_2$)$_m$—,
 —(CH$_2$)$_n$Q(CH$_2$)$_m$—,
 —(CH$_2$)$_n$O(CH$_2$)$_m$—,
 —(CH$_2$)$_n$N(R$^6$)(CH$_2$)$_m$—,
 —(CH$_2$)$_n$C(=O)(CH$_2$)$_m$—, or
 —(CH$_2$)$_n$S(O)$_p$(CH$_2$)$_m$—;
 wherein one or more of the methylene groups in U is optionally substituted with R$^7$;

Q is selected from 1,2-phenylene, 1,3-phenylene, 2,3-pyridinylene, 3,4-pyridinylene, or 2,4-pyridinylene;

R$^6$ is selected from: H, C$_1$–C$_4$ alkyl, or benzyl;

R$^7$ and R$^8$ are independently selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_0$–C$_6$ alkyl)-;

R$^{10}$ is selected from: H, N(R$^6$)$_2$, halogen, NO$_2$, CN, CF$_3$, CO$_2$R$^{17}$, C(=O)R$^{17}$, CONR$^{17}$R$^{20}$, —SO$_2$R$^{17}$, —SO$_2$NR$^{17}$R$^{20}$, C$_1$–C$_6$ alkyl substituted with 0–1 R$^{15}$ or 0–1 R$^{21}$, C$_1$–C$_4$ alkoxy substituted with 0–1 R$^{21}$, C$_3$–C$_6$ alkenyl substituted with 0–1 R$^{15}$ or 0–1 R$^{21}$, C$_3$–C$_7$ cycloalkyl substituted with 0–1 R$^{15}$ or 0–1 R$^{21}$, C$_4$–C$_{11}$ cycloalkylalkyl substituted with 0–1 R$^{15}$ or 0–1 R$^{21}$, aryl substituted with 0–1 R$^{15}$ or 0–2 R$^{11}$ or 0–1 R$^{21}$, or aryl(C$_1$–C$_6$ alkyl)- substituted with 0–1 R$^{15}$ or 0–2 R$^{11}$ or 0–1 R$^{21}$;

R$^{11}$ is selected from: H, halogen, CF$_3$, CN, NO$_2$, hydroxy, NR$^2$R$^3$, C$_1$–C$_4$ alkyl substituted with 0–1 R$^{21}$, C$_1$–C$_4$ alkoxy substituted with 0–1 R$^{21}$, aryl substituted with 0–1 R$^{21}$, aryl(C$_1$–C$_6$ alkyl)- substituted with 0–1 R$^{21}$, (C$_1$–C$_4$ alkoxy)carbonyl substituted with 0–1 R$^{21}$, (C$_1$–C$_4$ alkyl)carbonyl substituted with 0–1 R$^{21}$, C$_1$–C$_4$ alkylsulfonyl substituted with 0–1 R$^{21}$, or C$_1$–C$_4$ alkylaminosulfonyl substituted with 0–1 R$^{21}$;

W is —C(=O)—N(R$^{13}$)—(C(R$^{12}$)$_2$)$_q$—;

X is —C(R$^{12}$)(R$^{14}$)—C(R$^{12}$)(R$^{15}$)—;

alternatively, W and X can be taken together to be

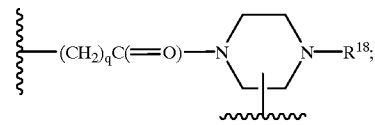

R$^{12}$ is H or C$_1$–C$_6$ alkyl;

R$^{13}$ is selected from: H, C$_1$–C$_6$ alkyl, C$_3$–C$_7$ cycloalkylmethyl, or aryl(C$_1$–C$_6$ alkyl)-;

R$^{14}$ is selected from: H, C$_1$–C$_6$ alkylthioalkyl, aryl (C$_1$–C$_{10}$ alkylthioalkyl)-, aryl(C$_1$–C$_{10}$ alkoxyalkyl)-, C$_1$–C$_{10}$ alkyl, C$_1$–C$_{10}$ alkoxyalkyl, C$_1$–C$_6$ hydroxyalkyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl (C$_1$–C$_6$ alkyl)-, heteroaryl(C$_1$–C$_6$ alkyl)-, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be substituted independently with 0–1 R$^{16}$ or 0–2 R$^{11}$;

R$^{15}$ is selected from: H, R$^{16}$, C$_1$–C$_{10}$ alkyl, C$_1$–C$_{10}$ alkoxyalkyl, C$_1$–C$_{10}$ alkylaminoalkyl, C$_1$–C$_{10}$ dialkylaminoalkyl, C$_1$–C$_{10}$ alkylcarbonyl, aryl(C$_0$–C$_6$ alkyl)carbonyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl (C$_1$–C$_6$ alkyl)-, heteroaryl(C$_1$–C$_6$ alkyl)-, aryl, heteroaryl, CO$_2$R$^{17}$, C(=O)R$^{17}$, CONR$^{17}$R$^{20}$, SO$_2$R$^{17}$, or SO$_2$NR$^{17}$R$^{20}$, provided that any of the above alkyl, cycloalkyl, aryl or heteroaryl groups may be substituted independently with 0–2 R$^{11}$;

Y is —COR$^{19}$;

R$^{16}$ is selected from:
 —N(R$^{20}$)—C(=O)—O—R$^{17}$,
 —N(R$^{20}$)—C(=O)—R$^{17}$,
 —N(R$^{20}$)—C(=O)—NH—R$^{17}$,
 —N(R$^{20}$)SO$_2$—R$^{17}$, or
 —N(R$^{20}$)SO$_2$—NR$^{20}$R$^{17}$;

R$^{17}$ is selected from: C$_1$–C$_{10}$ alkyl, C$_3$–C$_{11}$ cycloalkyl, aryl(C$_1$–C$_6$ alkyl)-, (C$_1$–C$_6$ alkyl)aryl, heteroaryl (C$_1$–C$_6$ alkyl)-, (C$_1$–C$_6$ alkyl)heteroaryl, biaryl(C$_1$–C$_6$ alkyl)-, heteroaryl, or aryl, wherein said aryl or heteroaryl groups are optionally substituted with 0–3 substituents selected from the group consisting of: C$_1$–C$_4$ alkyl, C$_1$–C$_4$ alkoxy, aryl, heteroaryl, halo, cyano, amino, CF$_3$, and NO$_2$;

R$^{19}$ is —O—(CH$_2$)$_k$N$^+$(R$^{22}$)(R$^{23}$)(R$^{24}$)Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{22}$, R$^{23}$ and R$^{24}$ are independently selected from: H, C$_1$–C$_6$ alkyl, C$_4$–C$_{11}$ cycloalkylalkyl, aryl, aryl(C$_1$–C$_6$ alkyl), heteroaryl, heteroaryl(C$_1$–C$_6$ alkyl) wherein said alkyl or aryl groups are substituted with 0–2 substituents selected from the group consisting of C$_1$–C$_4$ alkyl, C$_1$–C$_4$ alkoxy, OH, halo, CF$_3$, and nitro;

alternatively R$^{22}$ and R$^{23}$ can be taken together to form a 5–7 membered heterocyclic aromatic or non-aromatic ring system containing 1–3 heteroatoms selected from N, O and S and R$^{24}$ is defined as above or R$^{22}$, R$^{23}$, and R$^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ selected from: H, $C_1$–$C_6$ alkyl, $C_3$–$C_7$ cycloalkyl, $C_4$–$C_{11}$ cycloalkylalkyl, aryl($C_1$–$C_6$ alkyl)-, or heteroaryl($C_1$–$C_6$ alkyl)-;

$R^{21}$ is selected from COOH or $NR^6_2$;

k is 2–4;
m is 0–4;
n is 0–4;
p is 0–2;
q is 0–2;
t is 0–4; and
r is 0–2.

[3] Further preferred compounds of the invention as described above are compounds of the Formula IIa or IIb:

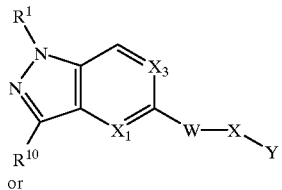

IIa or

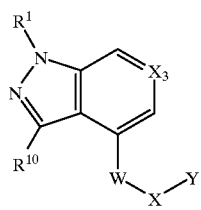

IIb including stereoisomeric forms thereof, or mixtures of stereoisomeric forms thereof, or pharmaceutically acceptable salt forms thereof wherein:

$X_1$ and $X_3$ are independently selected from nitrogen or carbon;

$R^1$ is selected from:

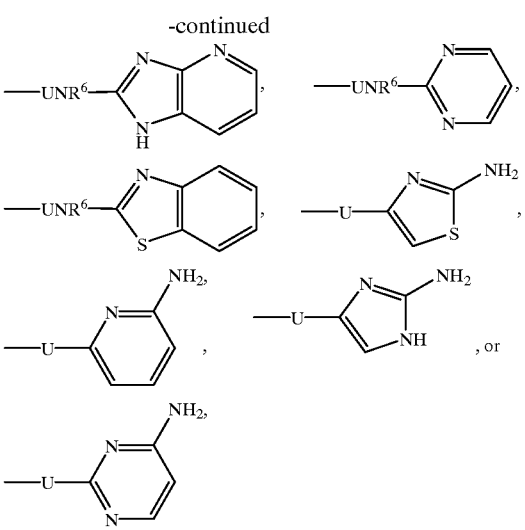

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_tQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

R7 is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, halogen, $CO_2R^{17}$, $CONR^{17}R^{20}$, $C_1$–$C_6$ alkyl substituted with 0–1 $R^{15}$ or 0–1 $R^{21}$, $C_1$–$C_4$ alkoxy substituted with 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—N($R^{20}$)$R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_k$$N^+$$(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, $C_1$–$C_4$ alkyl, and $C_4$–$C_{11}$cycloalkylalkyl;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{20}$ is H or $CH_3$;

$R^{21}$ is selected from COOH or $NR^6_2$;

k is 2;

m is 0 or 1;

n is 1–4; and t is 0 or 1.

[4] Still further preferred compounds of the above invention are compounds of the Formula IIa or IIb:

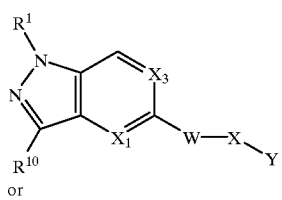

IIa or

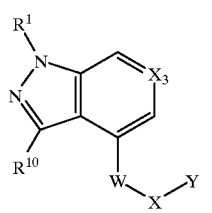

IIb including stereoisomeric forms thereof, or mixtures of stereoisomeric forms thereof, or pharmaceutically acceptable salt forms thereof wherein:

$X_1$ and $X_3$ are independently selected from nitrogen or carbon, provided that at least one of $X_1$ and $X_3$ is carbon;

$R^1$ is selected from:

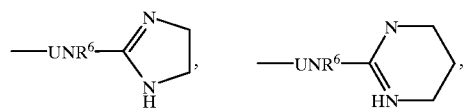

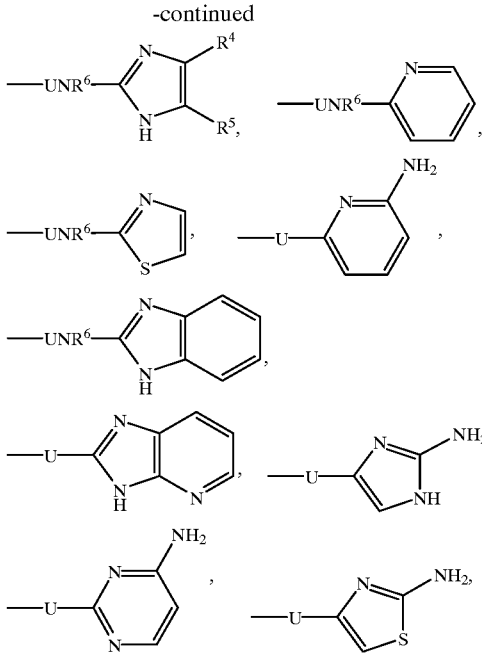

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_rQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, halogen, $CO_2R^{17}$, $CONR^{17}R^{20}$, $C_1$–$C_6$ alkyl substituted with 0–1 $R^{15}$ or 0–1 $R^{21}$, $C_1$–$C_4$ alkoxy substituted with 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

R¹⁶ is selected from:
—N(R²⁰)—C(=O)—O—R¹⁷,
—N(R²⁰)—C(=O)—R¹⁷,
—N(R²⁰)—C(=O)—NH—R¹⁷,
—N(R²⁰)SO₂—R¹⁷, or
—N(R²⁰)SO₂—NR²⁰R¹⁷;

R¹⁷ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

R¹⁹ is —O—(CH₂)$_k$N⁺(R²²)(R²³)(R²⁴)Z⁻;

Z⁻ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R²², R²³, and R²⁴ are independently selected from: H, methyl, ethyl, propyl and butyl;

alternatively R²² and R²³ can be taken together to form a 5–7 membered heterocyclic ring system containing 1–2 heteroatoms selected from N, O and S and R²⁴ is defined as above;

R²⁰ is H or $CH_3$;

R²¹ is selected from COOH or NR⁶₂;

k is 2;

m is 0 or 1;

n is 1–4; and t is 0 or 1.

[5] Specifically preferred compounds of the present invention are ammonium esters of compounds of Formula Ia, including enantiomeric forms, diasteriomeric forms or mixtures of enantiomeric or diasteriomeric forms thereof, and pharmaceutically acceptable salt forms thereof, wherein:

the ammonium ester is selected from:

(trimethylammonium)ethyl, (triethylammonium)ethyl, (diethylmethylammonium)ethyl,
(1-morpholinomethylammonium)ethyl,
(1-morpholinoethylammonium)ethyl,
(1-pyrrolidinomethylammonium)ethyl, and
(1-pyrrolidinoethylammoniumethyl ester; and the acid is selected from:

3-[1-[3-(imidazolin-2-ylamino)propyl]indazol-5-ylcarbonylamino]-2-(benzyloxycarbonylamino)-propionic acid,
3-[1-[3-(imidazolin-2-ylamino)propyl]indazol-5-ylcarbonylamino]-2-(2,4,6-trimethylbenzenesulfonylamino)propionic acid,
3-[1-[3-(imidazolin-2-ylamino)propyl]indazol-5-ylcarbonylamino]-2-(benzenesulfonylamino)propionic acid,
3-[1-[3-(imidazolin-2-ylamino)propyl]indazol-5-ylcarbonylamino]-2-(2,6-dichlorobenzene-sulfonylamino)propionic acid,
3-[1-[3-(imidazolin-2-ylamino)propyl]indazol-5-ylcarbonylamino]-2-(3,5-dimethylisoxazol-4-ylsulfonylamino)propionic acid,
3-[1-[3-(imidazolin-2-ylamino)propyl]indazol-5-ylcarbonylamino]-2-(2,6-dimethylbenzene-sulfonylamino)propionic acid,
3-[1-[3-(imidazolin-2-ylamino)propyl]indazol-5-ylcarbonylamino]-2-(2,6-dimethyl-4-phenylbenzenesulfonylamino)propionic acid,
3-[1-[3-(imidazolin-2-ylamino)propyl]indazol-5-ylcarbonylamino]-2-(4-phenylbenzenesulfonyl-amino)propionic acid,
3-[1-[3-(tetrahydropyrimid-2-ylamino)propyl]-indazol-5-ylcarbonylamino]-2-(benzyloxy-carbonylamino)propionic acid,
3-[1-[3-(tetrahydropyrimid-2-ylamino)propyl]-indazol-5-ylcarbonylamino]-2-(2,4,6-trimethylbenzenesulfonylamino)propionic acid,
3-[1-[3-(tetrahydropyrimid-2-ylamino)propyl]-indazol-5-ylcarbonylamino]-2-(benzenesulfonyl-amino)propionic acid,
3-[1-[3-(tetrahydropyrimid-2-ylamino)propyl]-indazol-5-ylcarbonylamino]-2-(2,6-dichlorobenzenesulfonylamino) propionic acid,
3-[1-[3-(tetrahydropyrimid-2-ylamino)propyl]-indazol-5-ylcarbonylamino]-2-(3,5-dimethyl-isoxazol-4-ylsulfonylamino)propionic acid,
3-[1-[3-(tetrahydropyrimid-2-ylamino)propyl]-indazol-5-ylcarbonylamino]-2-(2,6-dimethylbenzenesulfonylamino)propionic acid,
3-[1-[3-(tetrahydropyrimid-2-ylamino)propyl]-indazol-5-ylcarbonylamino]-2-(2,6-dimethyl-4-phenylbenzenesulfonylamino)propionic acid,
3-[1-[3-(tetrahydropyrimid-2-ylamino)propyl]-indazol-5-ylcarbonylamino]-2-(4-phenylbenzenesulfonylamino) propionic acid,
3-[1-[3-(imidazol-2-ylamino)propyl]indazol-5-yl-carbonylamino]-2-(benzyloxycarbonylamino)-propionic acid,
3-[1-[3-(imidazol-2-ylamino)propyl]indazol-5-yl-carbonylamino]-2-(2,4,6-trimethylbenzene-sulfonylamino)propionic acid,
3-[1-[3-(imidazol-2-ylamino)propyl]indazol-5-yl-carbonylamino]-2-(benzenesulfonylamino)-propionic acid,
3-[1-[3-(imidazol-2-ylamino)propyl]indazol-5-yl-carbonylamino]-2-(2,6-dichlorobenzene-sulfonylamino) propionic acid,
3-[1-[3-(imidazol-2-ylamino)propyl]indazol-5-yl-carbonylamino]-2-(3,5-dimethylisoxazol-4-ylsulfonylamino)propionic acid,
3-[1-[3-(imidazol-2-ylamino)propyl]indazol-5-yl-carbonylamino]-2-(2,6-dimethylbenzene-sulfonylamino) propionic acid,
3-[1-[3-(imidazol-2-ylamino)propyl]indazol-5-yl-carbonylamino]-2-(2,6-dimethyl-4-phenylbenzenesulfonylamino)propionic acid,
3-[1-[3-(imidazol-2-ylamino)propyl]indazol-5-yl-carbonylamino]-2-(4-phenylbenzenesulfonyl-amino) propionic acid,
3-[1-[3-(pyridin-2-ylamino)propyl]indazol-5-yl-carbonylamino]-2-(benzyloxycarbonylamino)-propionic acid,
3-[1-[3-(pyridin-2-ylamino)propyl]indazol-5-yl-carbonylamino]-2-(2,4,6-trimethylbenzene-sulfonylamino)propionic acid,
3-[1-[3-(pyridin-2-ylamino)propyl]indazol-5-yl-carbonylamino]-2-(benzenesulfonylamino)-propionic acid,
3-[1-[3-(pyridin-2-ylamino)propyl]indazol-5-yl-carbonylamino]-2-(2,6-dichlorobenzene-sulfonylamino) propionic acid,
3-[1-[3-(pyridin-2-ylamino)propyl]indazol-5-yl-carbonylamino]-2-(3,5-dimethylisoxazol-4-ylsulfonylamino)propionic acid, 3-[1-[3-(pyridin-2-ylamino)propyl]indazol-5-yl-carbonylamino]-2-(2,6-dimethylbenzene-sulfonylamino) propionic acid,
3-[1-[3-(pyridin-2-ylamino)propyl]indazol-5-yl-carbonylamino]-2-(2,6-dimethyl-4-phenylbenzenesulfonylamino)propionic acid,
3-[1-[3-(pyridin-2-ylamino)propyl]indazol-5-yl-carbonylamino]-2-(4-phenylbenzenesulfonyl-amino) propionic acid,
3-[1-[3-(imidazolin-2-ylamino)propyl]indazol-4-ylcarbonylamino]-2-(benzyloxycarbonylamino)-propionic acid,
3-[1-[3-(imidazolin-2-ylamino)propyl]indazol-4-ylcarbonylamino]-2-(2,4,6-trimethylbenzene-sulfonylamino)propionic acid,
3-[1-[3-(imidazolin-2-ylamino)propyl]indazol-4-ylcarbonylamino]-2-(benzenesulfonylamino)propionic acid,
3-[1-[3-(imidazolin-2-ylamino)propyl]indazol-4-ylcarbonylamino]-2-(2,6-dichlorobenzene-sulfonylamino)propionic acid,
3-[1-[3-(imidazolin-2-ylamino)propyl]indazol-4-ylcarbonylamino]-2-(3,5-dimethylisoxazol-4-ylsulfonylamino)propionic acid,
3-[1-[3-(imidazolin-2-ylamino)propyl]indazol-4-ylcarbonylamino]-2-(2,6-dimethylbenzene-sulfonylamino)propionic acid,
3-[1-[3-(imidazolin-2-ylamino)propyl]indazol-4-ylcarbonylamino]-2-(2,6-dimethyl-4-phenylbenzenesulfonylamino)propionic acid,
3-[1-[3-(imidazolin-2-ylamino)propyl]indazol-4-ylcarbonylamino]-2-(4-phenylbenzenesulfonyl-amino) propionic acid,
3-[1-[3-(tetrahydropyrimid-2-ylamino)propyl]-indazol-4-ylcarbonylamino]-2-(benzyloxy-carbonylamino) propionic acid,
3-[1-[3-(tetrahydropyrimid-2-ylamino)propyl]-indazol-4-ylcarbonylamino]-2-(2,4,6-trimethylbenzenesulfonylamino)propionic acid,
3-[1-[3-(tetrahydropyrimid-2-ylamino)propyl]-indazol-4-ylcarbonylamino]-2-(benzenesulfonyl-amino)propionic acid,
3-[1-[3-(tetrahydropyrimid-2-ylamino)propyl]-indazol-4-ylcarbonylamino]-2-(2,6-dichlorobenzenesulfonylamino) propionic acid,
3-[1-[3-(tetrahydropyrimid-2-ylamino)propyl]-indazol-4-ylcarbonylamino]-2-(3,5-dimethyl-isoxazol-4-ylsulfonylamino)propionic acid,
3-[1-[3-(tetrahydropyrimid-2-ylamino)propyl]-indazol-4-ylcarbonylamino]-2-(2,6-dimethylbenzenesulfonylamino)propionic acid,
3-[1-[3-(tetrahydropyrimid-2-ylamino)propyl]-indazol-4-ylcarbonylamino]-2-(2,6-dimethyl-4-phenylbenzenesulfonylamino)propionic acid,
3-[1-[3-(tetrahydropyrimid-2-ylamino)propyl]-indazol-4-ylcarbonylamino]-2-(4-phenylbenzene-sulfonylamino) propionic acid,
3-[1-[3-(imidazol-2-ylamino)propyl]indazol-4-yl-carbonylamino]-2-(benzyloxycarbonylamino)-propionic acid,
3-[1-[3-(imidazol-2-ylamino)propyl]indazol-4-yl-carbonylamino]-2-(2,4,6-trimethylbenzene-sulfonylamino)propionic acid,
3-[1-[3-(imidazol-2-ylamino)propyl]indazol-4-yl-carbonylamino]-2-(benzenesulfonylamino)-propionic acid,
3-[1-[3-(imidazol-2-ylamino)propyl]indazol-4-yl-carbonylamino]-2-(2,6-dichlorobenzene-sulfonylamino)propionic acid,
3-[1-[3-(imidazol-2-ylamino)propyl]indazol-4-yl-carbonylamino]-2-(3,5-dimethylisoxazol-4-ylsulfonylamino)propionic acid,
3-[1-[3-(imidazol-2-ylamino)propyl]indazol-4-yl-carbonylamino]-2-(2,6-dimethylbenzene-sulfonylamino) propionic acid,
3-[1-[3-(imidazol-2-ylamino)propyl]indazol-4-yl-carbonylamino]-2-(2,6-dimethyl-4-phenylbenzenesulfonylamino)propionic acid,
3-[1-[3-(imidazol-2-ylamino)propyl]indazol-4-yl-carbonylamino]-2-(4-phenylbenzenesulfonyl-amino) propionic acid,
3-[1-[3-(pyridin-2-ylamino)propyl]indazol-4-yl-carbonylamino]-2-(benzyloxycarbonylamino)-propionic acid,
3-[1-[3-(pyridin-2-ylamino)propyl]indazol-4-yl-carbonylamino]-2-(2,4,6-trimethylbenzene-sulfonylamino)propionic acid,
3-[1-[3-(pyridin-2-ylamino)propyl]indazol-4-yl-carbonylamino]-2-(benzenesulfonylamino)-propionic acid,
3-[1-[3-(pyridin-2-ylamino)propyl]indazol-4-yl-carbonylamino]-2-(2,6-dichlorobenzene-sulfonylamino) propionic acid,
3-[1-[3-(pyridin-2-ylamino)propyl]indazol-4-yl-carbonylamino]-2-(3,5-dimethylisoxazol-4-ylsulfonylamino)propionic acid,
3-[1-[3-(pyridin-2-ylamino)propyl]indazol-4-yl-carbonylamino]-2-(2,6-dimethylbenzene-sulfonylamino) propionic acid,
3-[1-[3-(pyridin-2-ylamino)propyl]indazol-4-yl-carbonylamino]-2-(2,6-dimethyl-4-phenylbenzenesulfonylamino)propionic acid, and
3-[1-[3-(pyridin-2-ylamino)propyl]indazol-4-yl-carbonylamino]-2-(4-phenylbenzenesulfonyl-amino) propionic acid.

[6] A second embodiment of the present invention comprises compounds of Formula Ib:

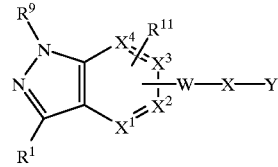

Ib including stereoisomeric forms thereof, or mixtures of stereoisomeric forms thereof, or pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

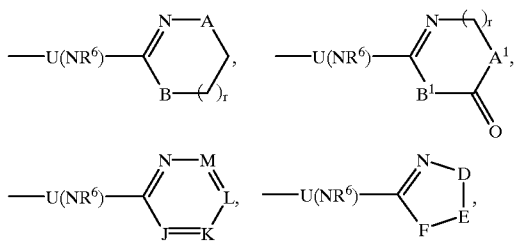

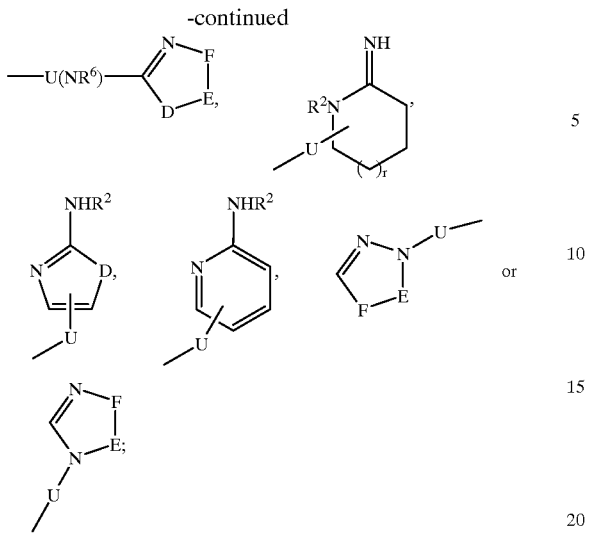

A and B are independently —CH$_2$—, —O—, —N(R$^2$)—, or —C(=O)—;

A$^1$ and B$^1$ are independently —CH$_2$— or —N(R$^3$)—;

D is —N(R$^2$)—, —O—, —S—, —C(=O)— or —SO$_2$—;

E—F is —C(R$^4$)=C(R$^5$)—, —N=C(R$^4$)—, —C(R$^4$)=N—, or —C(R$^4$)$_2$C(R$^5$)$_2$—;

J, K, L and M are independently selected from: —C(R$^4$)—, —C(R$^5$)— or —N—, provided that at least one of J, K, L and M is not —N—;

R$^2$ is selected from: H, C$_1$–C$_6$ alkyl, (C$_1$–C$_6$ alkyl)carbonyl, (C$_1$–C$_6$ alkoxy)carbonyl; (C$_1$–C$_6$ alkyl)aminocarbonyl, C$_3$–C$_6$ alkenyl, C$_3$–C$_7$ cycloalkyl, C$_4$–C$_{11}$ cycloalkylalkyl, aryl, heteroaryl(C$_1$–C$_6$ alkyl)carbonyl, heteroarylcarbonyl, aryl C$_1$–C$_6$ alkyl, (C$_1$–C$_6$ alkyl)carbonyl, or arylcarbonyl, C$_1$–C$_6$ alkylsulfonyl, arylsulfonyl, aryl(C$_1$–C$_6$ alkyl)sulfonyl, heteroarylsulfonyl, heteroaryl(C$_1$–C$_6$ alkyl)sulfonyl, aryloxycarbonyl, or aryl(C$_1$–C$_6$ alkoxy)carbonyl, wherein said aryl groups are substituted with 0–2 substituents selected from the group consisting of C$_1$–C$_4$ alkyl, C$_1$–C$_4$ alkoxy, halo, CF$_3$, and nitro;

R$^3$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_1$–C$_6$ alkyl)-;

R$^4$ and R$^5$ are independently selected from: H, C$_1$–C$_4$ alkoxy, NR$^2$R$^3$, halogen, NO$_2$, CN, CF$_3$, C$_1$–C$_6$ alkyl, C$_3$–C$_6$ alkenyl, C$_3$–C$_7$ cycloalkyl, C$_4$–C$_{11}$ cycloalkylalkyl, aryl, aryl(C$_1$–C$_6$ alkyl)-, (C$_1$–C$_6$ alkyl)carbonyl, (C$_1$–C$_6$ alkoxy)carbonyl, arylcarbonyl, or alternatively, when substituents on adjacent atoms, R$^4$ and R$^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: C$_1$–C$_4$ alkyl, C$_1$–C$_4$ alkoxy, halo, cyano, amino, CF$_3$, or NO$_2$;

U is selected from:
—(CH$_2$)$_n$—,
—(CH$_2$)$_n$(CR$^7$=CR$^8$)(CH$_2$)$_m$—
—(CH$_2$)$_n$(C≡C)(CH$_2$)$_m$—
—(CH$_2$)$_n$Q(CH$_2$)$_m$—
—(CH$_2$)$_n$O(CH$_2$)$_m$—,
—(CH$_2$)$_n$N(R$^6$)(CH$_2$)$_m$—,
—(CH$_2$)$_n$C(=O)(CH$_2$)$_m$—,
—(CH$_2$)$_n$(C=O)N(R$^6$)(CH$_2$)$_m$—
—(CH$_2$)$_n$N(R$^6$)(C=O)(CH$_2$)$_m$—, or
—(CH$_2$)$_n$S(O)$_p$(CH$_2$)$_m$—;
wherein one of the methylene groups is optionally substituted with R$^7$;

Q is selected from: 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

R$^6$ is selected from: H, C$_1$–C$_4$ alkyl, or benzyl;

R$^7$ and R$^8$ are independently selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_0$–C$_6$ alkyl)-;

R$^9$ is selected from: H, CO$_2$R$^{17}$, C(=O)R$^{17}$, CONR$^{17}$R$^{20}$, —SO$_2$R$^{17}$, —SO$_2$NR$^{17}$R$^{20}$, C$_1$–C$_6$ alkyl substituted with 0–1 R$^{15}$ or 0–1 R$^{21}$, C$_3$–C$_6$ alkenyl substituted with 0–1 R$^{15}$ or 0–1 R$^{21}$, C$_3$–C$_7$ cycloalkyl substituted with 0–1 R$^{15}$ or 0–1 R$^{21}$, C$_4$–C$_{11}$ cycloalkylalkyl substituted with 0–1 R$^{15}$ or 0–1 R$^{21}$, aryl substituted with 0–1 R$^{15}$ or 0–2 R$^{11}$ or 0–1 R$^{21}$, or aryl(C$_1$–C$_6$ alkyl)- substituted with 0–1 R$^{15}$ or 0–2 R$^{11}$ or 0–1 R$^{21}$;

R$^{11}$ is selected from H, halogen, CF$_3$, CN, NO$_2$, hydroxy, NR$^2$R$^3$, C$_1$–C$_4$ alkyl substituted with 0–1 R$^{21}$, C$_1$–C$_4$ alkoxy substituted with 0–1 R$^{21}$, aryl substituted with 0–1 R$^{21}$aryl(C$_1$–C$_6$ alkyl)- substituted with 0–1 R$^{21}$, (C$_1$–C$_4$ alkoxy)carbonyl substituted with 0–1 R$^{21}$, (C$_1$–C$_4$ alkyl)carbonyl substituted with 0–1 R$^{21}$, C$_1$–C$_4$ alkylsulfonyl substituted with 0–1 R$^{21}$, or C$_1$–C$_4$ alkylaminosulfonyl substituted with 0–1 R$^{21}$;

W is selected from:
—(C(R$^{12}$)$_2$)$_q$C(=O)N(R$^{13}$)—, or
—C(=O)—N(R$^{13}$)—(C(R$^{12}$)$_2$)$_q$—;

X is —C(R$^{12}$)(R$^{14}$)—C(R$^{12}$)(R$^{15}$)—; or alternatively, W and X can be taken together to be

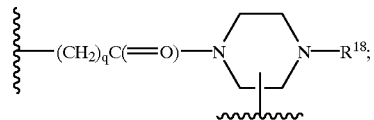

R$^{12}$ is selected from: H, halogen, C$_1$–C$_6$ alkyl, C$_2$–C$_6$ alkenyl, C$_2$–C$_6$ alkynyl, C$_3$–C$_7$ cycloalkyl, C$_4$–C$_{10}$ cycloalkylalkyl, (C$_1$–C$_4$ alkyl)carbonyl, aryl, or aryl (C$_1$–C$_6$ alkyl)-;

R$^{13}$ is selected from: H, C$_1$–C$_6$ alkyl, C$_3$–C$_7$ cycloalkylmethyl, or aryl(C$_1$–C$_6$ alkyl)-;

R$^{14}$ is selected from: H, C$_1$–C$_6$ alkylthio(C$_1$–C$_6$ alkyl)-, aryl(C$_1$–C$_{10}$ alkylthioalkyl)-, aryl(C$_1$–C$_{10}$ alkoxyalkyl)-, C$_1$–C$_{10}$ alkyl, C$_1$–C$_{10}$ alkoxyalkyl, C$_1$–C$_6$ hydroxyalkyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl (C$_1$–C$_6$ alkyl)-, heteroaryl(C$_1$–C$_6$ alkyl)-, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be unsubstituted or substituted independently with 0–1 R$^{16}$ or 0–2 R$^{11}$;

R$^{15}$ is selected from: H, R$^{16}$, C$_1$–C$_{10}$ alkyl, C$_1$–C$_{10}$ alkoxyalkyl, C$_1$–C$_{10}$ alkylaminoalkyl, C$_1$–C$_{10}$ dialkylaminoalkyl, (C$_1$–C$_{10}$ alkyl)carbonyl, aryl (C$_0$–C$_6$ alkyl)carbonyl, C$_1$–C$_{10}$ alkenyl, C$_1$–C$_{10}$ alkynyl, C$_3$–C$_{10}$ cycloalkyl, C$_3$–C$_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is —$COR^{19}$;

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R^{17}$, or
—$N(R^{20})SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_k N^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from H, $C_1$–$C_9$ alkyl, $C_4$–$C_{11}$ cycloalkylalkyl, aryl, aryl($C_1$–$C_6$ alkyl), heteroaryl, and heteroaryl($C_1$–$C_6$ alkyl), wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from: COOH or $NR^6_2$; and k is 2, 3, 4, 5, or 6;
m is 0, 1, 2, 3, or 4;
n is 0, 1, 2, 3, or 4;
t is 0, 1, 2, 3, or 4;
p is 0, 1, or 2;
q is 0, 1, or 2; and
r is 0, 1, or 2;

with the following provisos:
(1) t, n, m and q are chosen such that the number of atoms connecting $R^1$ and Y is in the range of 10–14; and
(2) n and m are chosen such that the value of n plus m is greater than one unless U is —$(CH_2)_t Q(CH_2)_m$—.

[7] Preferred compounds of the invention as described above are compounds of the Formula Ib:

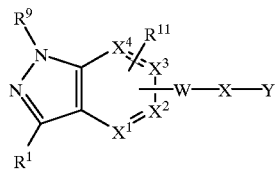

Ib including stereoisomeric forms thereof, or mixtures of stereoisomeric forms thereof, or pharmaceutically acceptable salt or prodrug forms thereof, wherein: including stereoisomeric forms thereof, or mixtures of stereoisomeric forms thereof, or pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

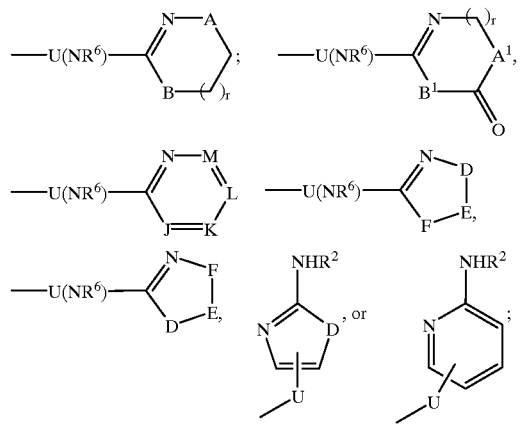

A and B are independently —$CH_2$—, —O—, —$N(R^2)$—, or —$C(=O)$—;
$A^1$ and $B^1$ are independently —$CH_2$— or —$N(R^3)$—;
D is —$N(R^2)$—, —O—, —S—, —$C(=O)$— or —$SO_2$—;
E—F is —$C(R^4)=C(R^5)$—, —$N=C(R^4)$—, —$C(R^4)=N$—, or —$C(R^4)_2 C(R^5)_2$—;
J, K, L and M are independently selected from —$C(R^4)$—, —$C(R^5)$— or —N—, provided that at least one of J, K, L and M is not —N—;
$R^2$ is selected from: H, $C_1$–$C_6$ alkyl, ($C_1$–$C_6$ alkyl)carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylalkyl, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, aryl($C_1$–$C_6$ alkoxy) carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7=CR^8)(CH_2)_m$—
—$(CH_2)_tQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—, or
—$(CH_2)_nS(O)_p(CH_2)_m$—;
wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–C6 alkyl)- substituted with 0–1 $R^{21}$, ($C_1$–$C_4$ alkoxy)carbonyl substituted with 0–1 $R^{21}$, ($C_1$–$C_4$ alkyl) carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —$C(=O)$—$N(R^{13})$—$(C(R^{12})_2)_q$-;

X is —$C(R^{12})(R^{14})$—$C(R^{12})(R^{15})$-;

alternatively, W and X can be taken together to be

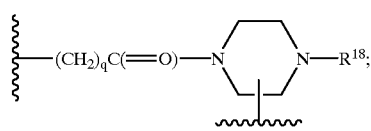

$R^{12}$ is H or $C_1$–$C_6$ alkyl;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from: H, $C_1$–$C_6$ alkylthioalkyl, aryl ($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is —$COR^{19}$;

$R^{16}$ is selected from:
—$N(R^{20})$—$C(=O)$—O—$R^{17}$,
—$N(R^{20})$—$C(=O)$—$R^{17}$,
—$N(R^{20})$—$C(=O)$—NH—$R^{17}$,
—$N(R^{20})SO_2$—$R^{17}$, or
—$N(R^{20})SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_k N^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from H, $C_1$–$C_6$ alkyl, $C_4$–$C_{11}$ cycloalkylalkyl, aryl, aryl($C_1$–$C_6$ alkyl), heteroaryl, and heteroaryl($C_1$–$C_6$ alkyl), wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from: COOH or $NR^6_2$;

k is 2–4;
m is 0–4;
n is 0–4;
t is 0–4;
p is 0–2;
q is 0–2; and
r is 0–2.

[8] Further preferred compounds of the invention as described above are compounds of the Formula IIc or IId:

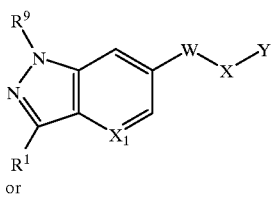

IIc or

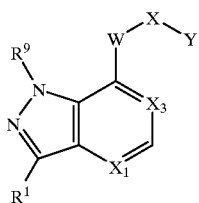

IId including stereoisomeric forms thereof, or mixtures of stereoisomeric forms thereof, or pharmaceutically acceptable salt forms thereof, wherein:

$X_1$ and $X_3$ are independently selected from nitrogen or carbon;

$R^1$ is selected from:

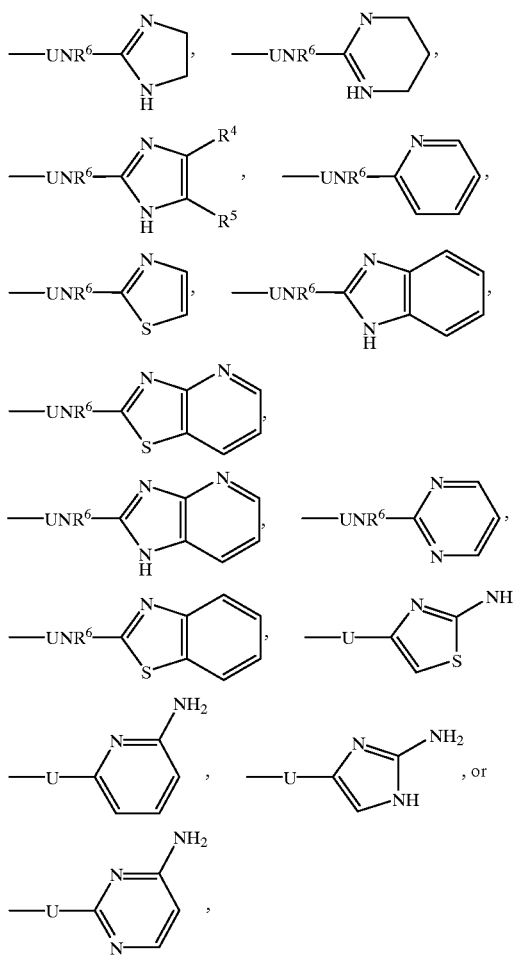

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(H_2)_tQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

R7 is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—N($R^{20}$)$R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, $C_1$–$C_4$ alkyl, and $C_4$–$C_{11}$ cycloalkylalkyl;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{20}$ is H or $CH_3$;

$R^{21}$ is selected from COOH or $NR^6{}_2$;
k is 2;
m is 0 or 1;
n is 1–4; and
t is 0 or 1.

[9] Still further preferred compounds of the above invention are compounds of the Formula IIc or IId:

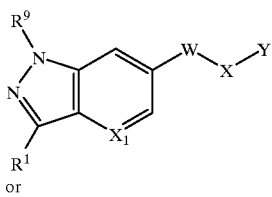

IIc or

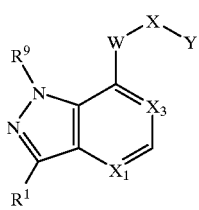

IId including stereoisomeric forms thereof, or mixtures of stereoisomeric forms thereof, or pharmaceutically acceptable salt forms thereof, wherein:

$X_1$ and $X_3$ are independently selected from nitrogen or carbon, provided that at least one of $X_1$ and $X_3$ is carbon;

$R^1$ is selected from:

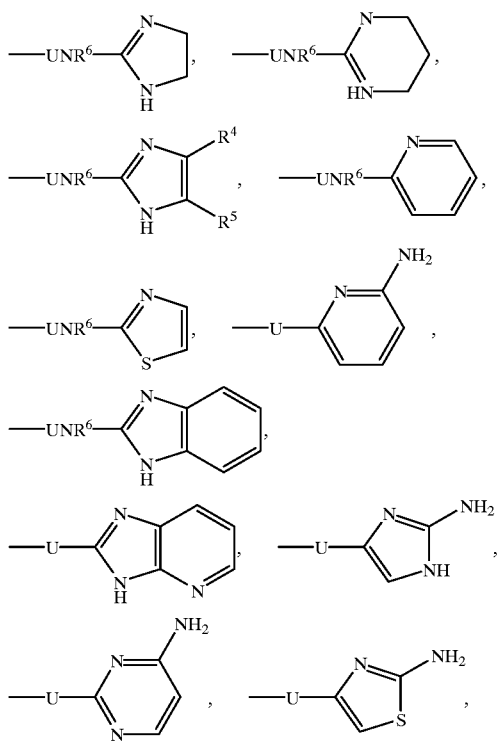

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl:

U is —$(CH_2)_n$—, —$(CH_2)_rQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

R7 is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—N($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, methyl, ethyl, propyl and butyl;

alternatively $R^{22}$ and $R^{23}$ can be taken together to form a 5–7 membered heterocyclic ring system containing 1–2 heteroatoms selected from N, O and S and $R^{24}$ is defined as above;

$R^{20}$ is H or $CH_3$;

$R^{21}$ is selected from COOH or $NR^6_2$; and
k is 2;
m is 0 or 1;
n is 1–4; and
t is 0 or 1.

[10] Specifically preferred compounds of the present invention are ammonium esters of compounds of Formula Ib, including enantiomeric forms, diasteriomeric forms or mixtures of enantiomeric or diasteriomeric forms thereof, and pharmaceutically acceptable salt forms thereof, wherein:

the ammonium ester is selected from:

(trimethylammonium)ethyl, (triethylammonium)ethyl, (diethylmethylammonium)ethyl,
(1-morpholinomethylammonium)ethyl,
(1-morpholinoethylammonium)ethyl,
(1-pyrrolidinomethylammonium)ethyl, and
(1-pyrrolidinoethylammoniumethyl ester; and the acid is selected from:

3-[3-[3-(imidazolin-2-ylamino)propyl]indazol-6-ylcarbonyl amino]-2-(benzyloxycarbonylamino)-propionic acid,
3-[1-methyl-3-[3-(imidazolin-2-ylamino)propyl]-indazol-6-ylcarbonylamino]-2-(2,4,6-trimethylbenzenesulfonylamino)propionic acid,
3-[3-[3-(imidazolin-2-ylamino)propyl]indazol-6-ylcarbonyl amino]-2-(benzenesulfonylamino)propionic acid,
3-[1-methyl-3-[3-(imidazolin-2-ylamino)propyl]-indazol-6-ylcarbonylamino]-2-(2,6-dichlorobenzenesulfonylamino) propionic acid,
3-[3-[3-(imidazolin-2-ylamino)propyl]indazol-6-ylcarbonylamino]-2-(3,5-dimethylisoxazol-4-ylsulfonylamino) propionic acid,
3-[1-methyl-3-[3-(imidazolin-2-ylamino)propyl]-indazol-6-ylcarbonyl amino]-2-(2,6-dimethylbenzenesulfonylamino)propionic acid,
3-[3-[3-(imidazolin-2-ylamino)propyl]indazol-6-ylcarbonylamino]-2-(2,6-dimethyl-4-phenylbenzenesulfonylamino)propionic acid,
3-[1-methyl-3-[3-(imidazolin-2-ylamino)propyl]-indazol-6-ylcarbonyl amino]-2-(4-phenylbenzene-sulfonylamino) propionic acid,
3-[3-[3-(tetrahydropyrimid-2-ylamino)propyl]-indazol-6-ylcarbonylamino]-2-(benzyloxy-carbonylamino) propionic acid,
3-[1-methyl-3-[3-(tetrahydropyrimid-2-ylamino)propyl]indazol-6-ylcarbonylamino]-2-(2,4,6-trimethylbenzenesulfonylamino)propionic acid,
3-[3-[3-(tetrahydropyrimid-2-ylamino)propyl]-indazol-6-ylcarbonylamino]-2-(benzenesulfonyl-amino)propionic acid,
3-[1-methyl-3-[3-(tetrahydropyrimid-2-ylamino)propyl]indazol-6-ylcarbonylamino]-2-(2,6-dichlorobenzenesulfonylamino)propionic acid,
3-[3-[3-(tetrahydropyrimid-2-ylamino)propyl]-indazol-6-ylcarbonylamino]-2-(3,5-dimethyl-isoxazol-4-ylsulfonylamino)propionic acid,
3-[1-methyl-3-[3-(tetrahydropyrimid-2-ylamino)propyl]indazol-6-ylcarbonylamino]-2-(2,6-dimethylbenzenesulfonylamino)propionic acid,
3-[3-[3-(tetrahydropyrimid-2-ylamino)propyl]-indazol-6-ylcarbonylamino]-2-(2,6-dimethyl-4-phenylbenzenesulfonylamino)propionic acid,
3-[1-methyl-3-[3-(tetrahydropyrimid-2-ylamino)-propyl]-indazol-6-ylcarbonylamino]-2-(4-phenylbenzenesulfonylamino)propionic acid,
3-[3-[3-(imidazol-2-ylamino)propyl]indazol-6-ylcarbonylamino]-2-(benzyloxycarbonylamino)-propionic acid,
3-[1-methyl-3-[3-(imidazol-2-ylamino)propyl]-indazol-6-ylcarbonylamino]-2-(2,4,6-trimethylbenzenesulfonylamino)propionic acid,
3-[3-[3-(imidazol-2-ylamino)propyl]indazol-6-ylcarbonylamino]-2-(benzenesulfonylamino)-propionic acid,
3-[1-methyl-3-[3-(imidazol-2-ylamino)propyl]-indazol-6-ylcarbonyl amino]-2-(2,6-dichlorobenzenesulfonylamino)propionic acid,
3-[3-[3-(imidazol-2-ylamino)propyl]indazol-6-ylcarbonylamino]-2-(3,5-dimethylisoxazol-4-ylsulfonylamino)propionic acid,
3-[1-methyl-3-[3-(imidazol-2-ylamino)propyl]-indazol-6-ylcarbonyl amino]-2-(2,6-dimethylbenzenesulfonylamino)propionic acid,
3-[3-[3-(imidazol-2-ylamino)propyl]indazol-6-ylcarbonylamino]-2-(2,6-dimethyl-4-phenylbenzenesulfonylamino)propionic acid,
3-[1-methyl-3-[3-(imidazol-2-ylamino)propyl]-indazol-6-ylcarbonylamino]-2-(4-phenylbenzene-sulfonylamino) propionic acid,
3-[3-[3-(pyridin-2-ylamino)propyl]indazol-6-ylcarbonylamino]-2-(benzyloxycarbonylamino)-propionic acid,
3-[1-methyl-3-[3-(pyridin-2-ylamino)propyl]indazol-6-ylcarbonylamino]-2-(2,4,6-trimethylbenzene-sulfonylamino)propionic acid,
3-[3-[3-(pyridin-2-ylamino)propyl]indazol-6-yl-carbonylamino]-2-(benzenesulfonylamino)- propionic acid,
3-[1-methyl-3-[3-(pyridin-2-ylamino)propyl]indazol-6-ylcarbonylamino]-2-(2,6-dichlorobenzene-sulfonylamino)propionic acid,
3-[3-[3-(pyridin-2-ylamino)propyl]indazol-6-yl-carbonylamino]-2-(3,5-dimethylisoxazol-4-ylsulfonylamino)propionic acid,
3-[1-methyl-3-[3-(pyridin-2-ylamino)propyl]indazol-6-ylcarbonylamino]-2-(2,6-dimethylbenzene-sulfonylamino)propionic acid,
3-[3-[3-(pyridin-2-ylamino)propyl]indazol-6-yl-carbonylamino]-2-(2,6-dimethyl-4-phenylbenzenesulfonylamino)propionic acid,
3-[1-methyl-3-[3-(pyridin-2-ylamino)propyl]indazol-6-ylcarbonylamino]-2-(4-phenylbenzenesulfonyl-amino) propionic acid,
3-[3-[3-(imidazolin-2-ylamino)propyl]indazol-7-ylcarbonylamino]-2-(benzyloxycarbonylamino)-propionic acid,
3-[1-methyl-3-[3-(imidazolin-2-ylamino)propyl]-indazol-7-ylcarbonylamino]-2-(2,4,6-trimethylbenzenesulfonylamino)propionic acid,
3-[3-[3-(imidazolin-2-ylamino)propyl]indazol-7-ylcarbonylamino]-2-(benzenesulfonylamino)propionic acid,
3-[1-methyl-3-[3-(imidazolin-2-ylamino)propyl]-indazol-7-ylcarbonylamino]-2-(2,6-dichlorobenzenesulfonylamino) propionic acid,
3-[3-[3-(imidazolin-2-ylamino)propyl]indazol-7-ylcarbonylamino]-2-(3,5-dimethylisoxazol-4-ylsulfonylamino)propionic acid,
3-[1-methyl-3-[3-(imidazolin-2-ylamino)propyl]-indazol-7-ylcarbonylamino]-2-(2,6-dimethylbenzenesulfonylamino)propionic acid,
3-[3-[3-(imidazolin-2-ylamino)propyl]indazol-7-ylcarbonylamino]-2-(2,6-dimethyl-4-phenylbenzenesulfonylamino)propionic acid, 3-[1-methyl-3-[3-(imidazolin-2-ylamino)propyl]-indazol-7-ylcarbonylamino]-2-(4-phenylbenzene-sulfonylamino)propionic acid,
3-[3-[3-(tetrahydropyrimid-2-ylamino)propyl]-indazol-7-ylcarbonylamino]-2-(benzyloxy-carbonylamino) propionic acid,
3-[1-methyl-3-[3-(tetrahydropyrimid-2-ylamino)propyl] indazol-7-ylcarbonylamino]-2-(2,4,6-trimethylbenzenesulfonylamino)propionic acid,
3-[3-[3-(tetrahydropyrimid-2-ylamino)propyl]-indazol-7-ylcarbonylamino]-2-(benzenesulfonyl-amino)propionic acid,
3-[1-methyl-3-[3-(tetrahydropyrimid-2-ylamino)propyl] indazol-7-ylcarbonylamino]-2-(2,6-dichlorobenzenesulfonylamino)propionic acid,
3-[3-[3-(tetrahydropyrimid-2-ylamino)propyl]-indazol-7-ylcarbonylamino]-2-(3,5-dimethyl-isoxazol-4-ylsulfonylamino)propionic acid,
3-[1-methyl-3-[3-(tetrahydropyrimid-2-ylamino)propyl] indazol-7-ylcarbonylamino]-2-(2,6-dimethylbenzenesulfonylamino)propionic acid,
3-[3-[3-(tetrahydropyrimid-2-ylamino)propyl]-indazol-7-ylcarbonylamino]-2-(2,6-dimethyl-4-phenylbenzenesulfonylamino)propionic acid,
3-[1-methyl-3-[3-(tetrahydropyrimid-2-ylamino)propyl] indazol-7-ylcarbonylamino]-2-(4-phenylbenzenesulfonylamino)propionic acid,
3-[3-[3-(imidazol-2-ylamino)propyl]indazol-7-ylcarbonylamino]-2-(benzyloxycarbonylamino)-propionic acid,
3-[1-methyl-3-[3-(imidazol-2-ylamino)propyl]-indazol-7-ylcarbonylamino]-2-(2,4,6-trimethylbenzenesulfonylamino)propionic acid,
3-[3-[3-(imidazol-2-ylamino)propyl]indazol-7-ylcarbonylamino]-2-(benzenesulfonylamino)- propionic acid,
3-[1-methyl-3-[3-(imidazol-2-ylamino)propyl]-indazol-7-ylcarbonylamino]-2-(2,6-dichlorobenzenesulfonylamino) propionic acid,
3-[3-[3-(imidazol-2-ylamino)propyl]indazol-7-ylcarbonylamino]-2-(3,5-dimethylisoxazol-4-ylsulfonylamino)propionic acid,
3-[1-methyl-3-[3-(imidazol-2-ylamino)propyl]-indazol-7-ylcarbonylamino]-2-(2,6-dimethylbenzenesulfonylamino)propionic acid,
3-[3-[3-(imidazol-2-ylamino)propyl]indazol-7-ylcarbonylamino]-2-(2,6-dimethyl-4-phenylbenzenesulfonylamino)propionic acid,
3-[1-methyl-3-[3-(imidazol-2-ylamino)propyl]-indazol-7-ylcarbonylamino]-2-(4-phenylbenzene-sulfonylamino) propionic acid,
3-[3-[3-(pyridin-2-ylamino)propyl]indazol-7-yl-carbonylamino]-2-(benzyloxycarbonylamino)-propionic acid,
3-[1-methyl-3-[3-(pyridin-2-ylamino)propyl]indazol-7-ylcarbonylamino]-2-(2,4,6-trimethylbenzene-sulfonylamino)propionic acid,
3-[3-[3-(pyridin-2-ylamino)propyl]indazol-7-yl-carbonylamino]-2-(benzenesulfonylamino)- propionic acid,
3-[1-methyl-3-[3-(pyridin-2-ylamino)propyl]indazol-7-ylcarbonylamino]-2-(2,6-dichlorobenzene-sulfonylamino)propionic acid,
3-[3-[3-(pyridin-2-ylamino)propyl]indazol-7-yl-carbonylamino]-2-(3,5-dimethylisoxazol-4-ylsulfonylamino)propionic acid,
3-[1-methyl-3-[3-(pyridin-2-ylamino)propyl]indazol-7-ylcarbonylamino]-2-(2,6-dimethylbenzene-sulfonylamino)propionic acid,
3-[3-[3-(pyridin-2-ylamino)propyl]indazol-7-yl-carbonylamino]-2-(2,6-dimethyl-4-phenylbenzenesulfonylamino)propionic acid, and
3-[1-methyl-3-[3-(pyridin-2-ylamino)propyl]indazol-7-ylcarbonylamino]-2-(4-phenylbenzenesulfonyl-amino)propionic acid;

[11] A third embodiment of the present invention comprises compounds of Formula Ic:

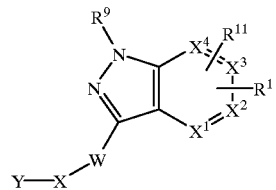

Ic including stereoisomeric forms thereof, or mixtures of stereoisomeric forms thereof, or pharmaceutically acceptable salt forms, thereof wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

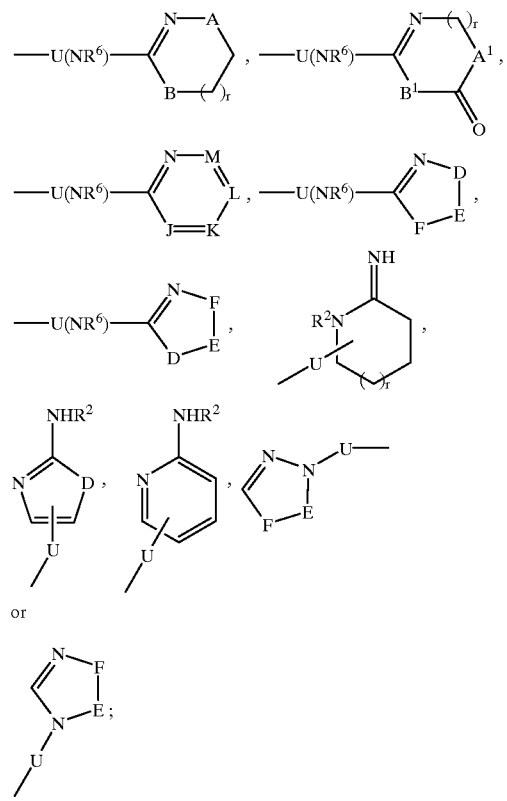

or

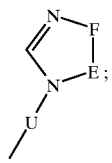

A and B are independently —$CH_2$—, —O—, —N($R^2$)—, or —C(=O)—;
$A^1$ and $B^1$ are independently —$CH_2$— or —($R^3$)—;
D is —N($R^2$)—, —O—, —S—, —C(=O)— or —$SO_2$—;
E—F is —C($R^4$)=C($R^5$)—, —N=C($R^4$)—, —C($R^4$)=N—, or —C($R^4$)$_2$C($R^5$)$_2$—;

J, K, L and M are independently selected from —C($R^4$)—, —C($R^5$)— or —N—, provided that at least one of J, K, L and M is not —N—;

$R^2$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl)aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl $C_1$–$C_6$ alkyl, ($C_1$–$C_6$ alkyl)carbonyl, or arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl)carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7=CR^8)(CH_2)_m$—
—$(CH_2)_n(C≡C)(CH_2)_m$—
—$(CH_2)_nQ(CH_2)_m$—
—$(CH_2)_nO(CH_2)_m$—,
—$(CH_2)_nN(R^6)(CH_2)_m$—,
—$(CH_2)_nC(=O)(CH_2)_m$—,
—$(CH_2)_n(C=O)N(R^6)(CH_2)_m$—
—$(CH_2)_nN(R^6)(C=O)(CH_2)_m$—, or
—$(CH_2)_nS(O)_p(CH_2)_m$—;
wherein one of the methylene groups is optionally substituted with $R^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from:
—$(C(R^{12})_2)_qC(=O)N(R^{13})$—, or
—$C(=O)$—$N(R^{13})$—$(C(R^{12})_2)_q$—;

X is —$C(R^{12})(R^{14})$—$C(R^{12})(R^{15})$—; or alternatively, W and X can be taken together to be

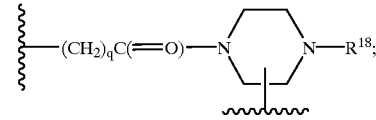

$R^{12}$ is selected from: H, halogen, $C_1$–$C_6$ alkyl, $C_2$–$C_6$ alkenyl, $C_2$–$C_6$ alkynyl, $C_3$–$C_7$ cycloalkyl, $C_4$–C cycloalkylalkyl, ($C_1$–$C_4$ alkyl)carbonyl, aryl, or aryl($C_1$–$C_6$ alkyl)-;

$R^{13}$ is selected from: H, $C_1$–$C_6$ alkyl, $C_3$–$C_7$ cycloalkylmethyl, or aryl($C_1$–$C_6$ alkyl)-

$R^{14}$ is selected from: H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–C cycloalkyl, $C_3$–C cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$—$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17,}$ $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is —$COR^{19}$;

$R^{16}$ is selected from:
—$N(R^{20})$—$C(=O)$—O—$R^{17}$,
—$N(R^{20})$—$C(=O)$—$R^{17}$,
—$N(R^{20})$—$C(=O)$—NH—$R^{17}$,
—$N(R^{20})SO_2$—$R^{17}$, or
—$N(R^{20})SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_{1-C6}$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from H, $C_1$–$C_9$ alkyl, $C_4$–$C_{11}$ cycloalkylalkyl, aryl, aryl($C_1$–$C_6$ alkyl), heteroaryl, and heteroaryl($C_1$–$C_6$ alkyl), wherein said alkyl or aryl groups are substituted with 0–2 substituents selected from the group consisting of $C_1$–$C_4$ alkyl, $C_1$–$C_4$ alkoxy, OH, halo, $CF_3$, and nitro; alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from: COOH or $NR^6{}_2$; and k is 2, 3, 4, 5, or 6;
m is 0, 1, 2, 3, or 4;
n is 0, 1, 2, 3, or 4;
t is 0, 1, 2, 3, or 4;
p is 0, 1, or 2;
q is 0, 1, or 2; and
r is 0, 1, or 2;

with the following provisos:

(1) t, n, m and q are chosen such that the number of atoms connecting $R^1$ and Y is in the range of 10–14; and
(2) n and m are chosen such that the value of n plus m is greater than one unless U is —$(CH_2)_tQ(CH_2)_m$—.

[12] Preferred compounds of the invention as described above are compounds of the Formula Ic:

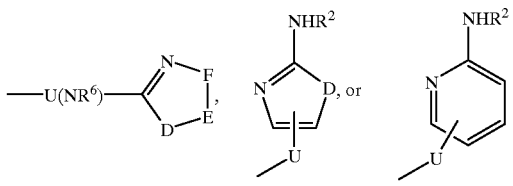

Ic including stereoisomeric forms thereof, or mixtures of stereoisomeric forms thereof, or pharmaceutically acceptable salt forms thereof wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

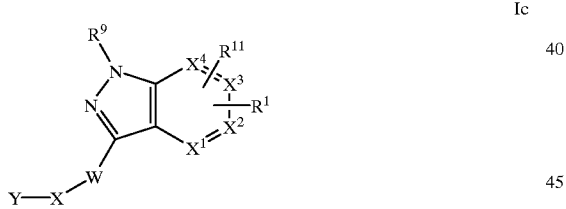

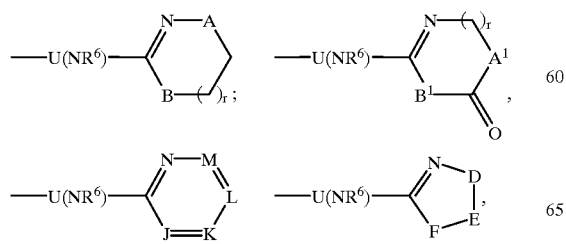

A and B are independently —$CH_2$—, —O—, —$N(R^2)$—, or —$C(=O)$—;
$A^1$ and $B^1$ are independently —$CH_2$— or —N(R3)—;
D is —$N(R^2)$—, —O—, —S—, —$C(=O)$— or —$SO_2$—;
E—F is —$C(R^4)=C(R^5)$—, —$N=C(R^4)$—, —$C(R^4)=N$—, or —$C(R^4)_2C(R^5)_2$—;
J, K, L and M are independently selected from: —$C(R^4)$—, —$C(R^5)$— or —N—, provided that at least one of J, K, L and M is not —N—;
$R^2$ is selected from: H, $C_1$–$C_6$ alkyl, ($C_1$–$C_6$ alkyl) carbonyl, ($C_{1-C6}$ alkoxy)carbonyl, $C_{1-C6}$ alkylaminocarbonyl, $C_3$–$C_6$ alkenyl, $C_3$–$C_7$ cycloalkyl, $C_4$–$C_{11}$ cycloalkylalkyl, aryl, heteroaryl ($C_1$–$C_6$ alkyl)carbonyl, heteroarylcarbonyl, aryl ($C_1$–$C_6$ alkyl)-, ($C_{1-C6}$ alkyl)carbonyl, arylcarbonyl, alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, aryl($C_1$–$C_6$ alkoxy) carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7=CR^8)(CH_2)_m$—
—$(CH_2)_tQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—, or
—$(CH_2)_nS(O)_p(CH_2)_m$—;
wherein one of the methylene groups is optionally substituted with $R^7$;

Q is selected from 1,2-phenylene, 1,3-phenylene, 2,3-pyridinylene, 3,4-pyridinylene, or 2,4-pyridinylene;
$R^6$ is selected from: H, $C_1$–$C_4$ alkyl, or benzyl;
$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;
$R^9$ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is $-C(=O)-N(R^{13})-(C(R^{12})_2)_q-$;
X is $-C(R^{12})(R^{14})-C(R^{12})(R^{15})-$;
alternatively, W and X can be taken together to be

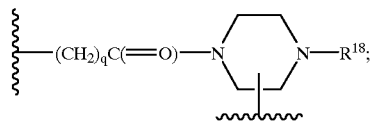

$R^{12}$ is H or $C_1$–$C_6$ alkyl;
$R^{13}$ is selected from: H, $C_1$–$C_6$ alkyl, $C_3$–$C_7$ cycloalkylmethyl, or aryl($C_1$–$C_6$ alkyl)-;
$R^{14}$ is selected from: H, $C_1$–$C_6$ alkylthioalkyl, aryl ($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;
$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;
Y is $-COR^{19}$;
$R^{16}$ is selected from:
  $-N(R^{20})-C(=O)-O-R^{17}$,
  $-N(R^{20})-C(=O)-R^{17}$,
  $-N(R^{20})-C(=O)-NH-R^{17}$,
  $-N(R^{20})SO_2-R^{17}$, or
  $-N(R^{20})SO_2-NR^{20}R^{17}$;
$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;
$R^{19}$ is $-O-(CH_2)_kN^+(R^{22})(R^{23})(R^{24})Z^-$;
$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from H, $C_1$–$C_6$ alkyl, $C_4$–$C_{11}$ cycloalkylalkyl, aryl, aryl($C_1$–$C_6$ alkyl), heteroaryl, and heteroaryl($C_1$–$C_6$ alkyl), wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from: COOH or $NR^6_2$;
k is 2–4;
m is 0–4;
n is 0–4;
t is 0–4;
p is 0–2;
q is 0–2; and
r is 0–2.

[13] Further preferred compounds of the invention as described above are compounds of the Formula IIe or IIf:

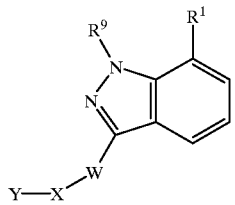

IIe

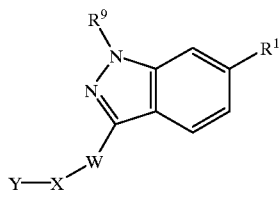

IIf including stereoisomeric forms thereof, or mixtures of stereoisomeric forms thereof, or pharmaceutically acceptable salt forms thereof, wherein:

$R^1$ is selected from:

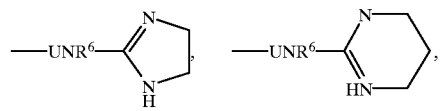

-continued

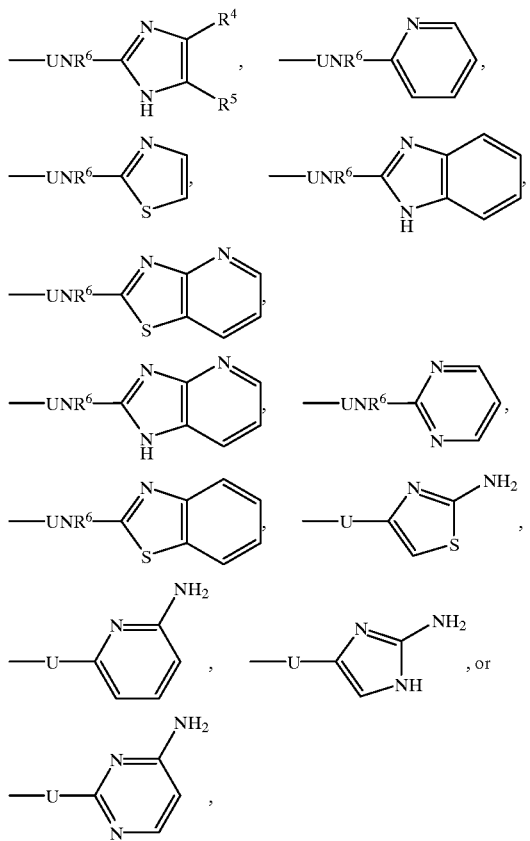

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is $—(CH_2)_n—$, $—(CH_2)_tQ(CH_2)_m—$ or $—C(=O)(CH_2)_{n-1}—$, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

R7 is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, $—SO_2R^{17}$, $—SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is $—C(=O)—N(R^{13})—$;

X is $—CH(R^{14})—CH(R^{15})—$;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is $—COR^{19}$;

$R^{16}$ is selected from:
  $—NH(R^{20})—C(=O)—O—R^{17}$,
  $—N(R^{20})—C(=O)—R^{17}$,
  $—N(R^{20})—C(=O)—NH—R^{17}$,
  $—N(R^{20})SO_2—R^{17}$, or
  $—N(R^{20})SO_2—N(R^{20})R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is $—O—(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, $C_1$–$C_4$ alkyl, and $C_4$–$C_{11}$ cycloalkylalkyl;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{20}$ is H or $CH_3$;

$R^{21}$ is selected from COOH or $NR^6_2$;

k is 2;

m is 0 or 1;

n is 1–4; and t is 0 or 1.

[14] Still further preferred compounds of the above described are compounds of the Formula IIe or IIf:

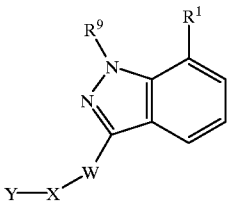

IIe

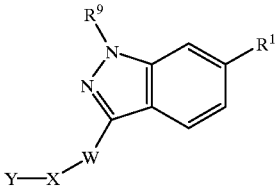

IIf including stereoisomeric forms thereof, or mixtures of stereoisomeric forms thereof, or pharmaceutically acceptable salt forms thereof, wherein:

$R^1$ is selected from:

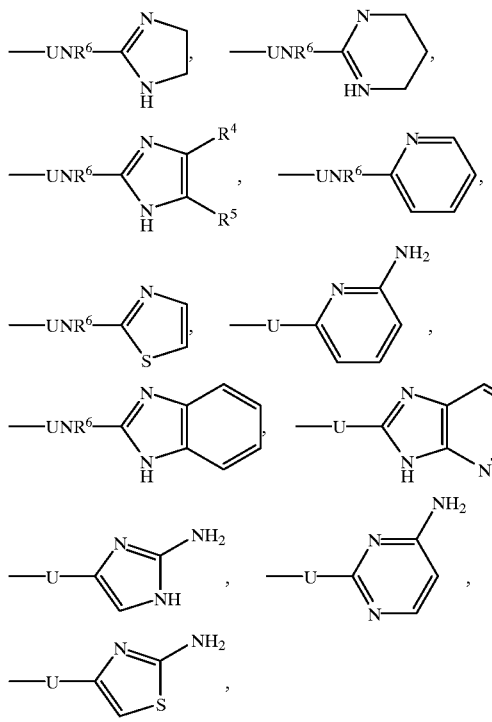

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl:

U is —$(CH_2)_n$—, —$(CH_2)_tQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ selected from: H, $C_1$–$C_4$ alkyl, or benzyl;

R7 is selected from $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from (trimethylammonium)ethyl, (triethylammonium)ethyl, (diethylmethylammonium)ethyl, (1-morpholinomethylammonium)ethyl, (1-morpholinoethylammonium)ethyl, (1-pyrrolidinomethylammonium)ethyl, and (1-pyrrolidinoethyl)ammoniumethyl ester prodrug groups;

$R^{20}$ is H or $CH_3$;

$R^{21}$ is selected from COOH or $NR^6_2$; and m is 0 or 1;
n is 1–4; and
t is 0 or 1.

[15] A fourth embodiment of the present invention comprises compounds of Formula Id:

$$R^1—Q''—W—X—Y \qquad (Id)$$

and pharmaceutically acceptable salt forms thereof, wherein:

Q" is selected from

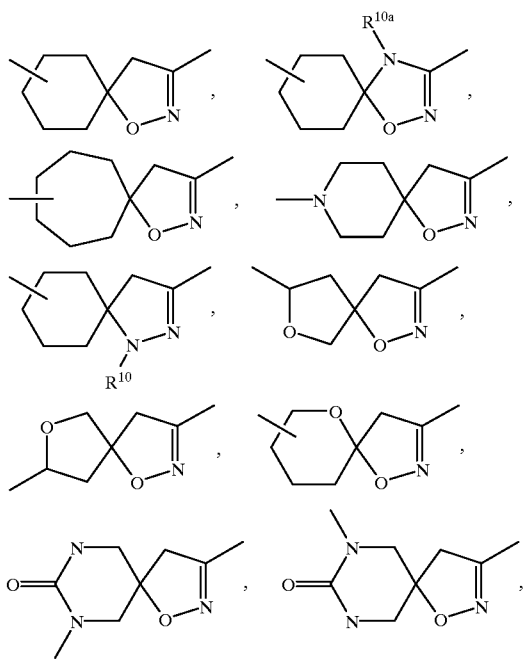

-continued

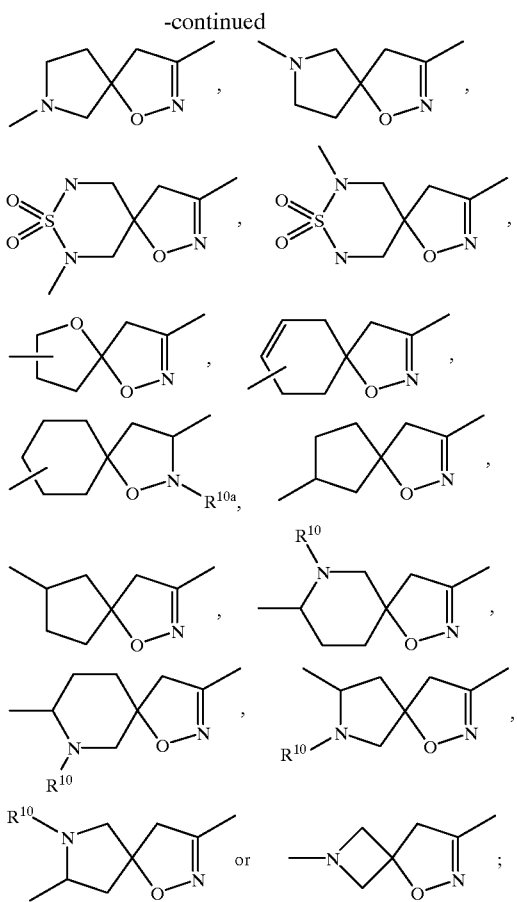

R¹ is selected from:

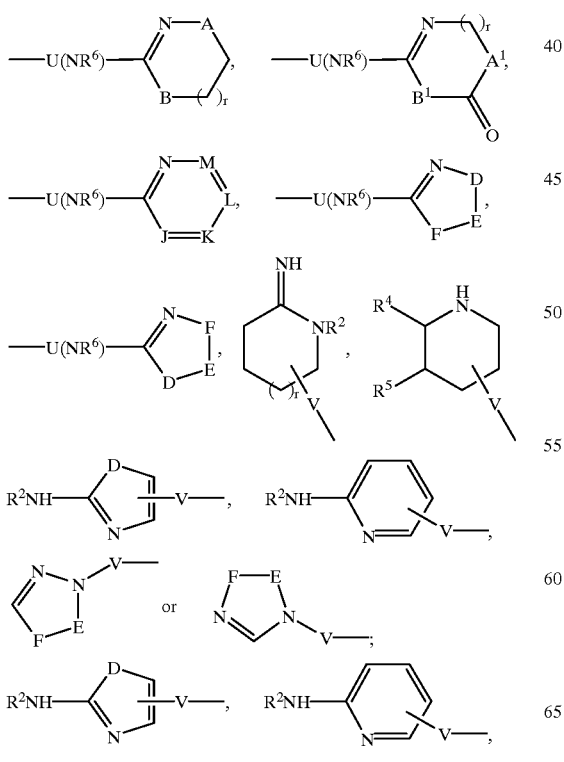

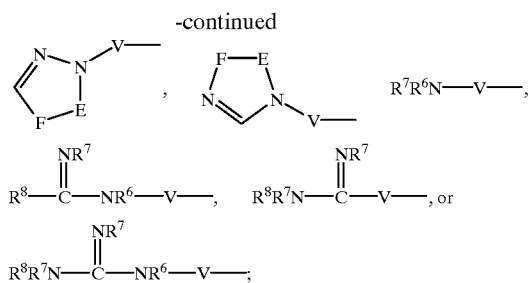

A and B are independently —CH₂—, —O—, —N(R²)—, or —C(=O)—;
A¹ and B¹ are independently —CH₂— or —N(R³)—;
D is —N(R²)—, —O—, —S—, —C(=O)— or —SO₂—;
E—F is —C(R⁴)=C(R⁵)—, —N=C(R⁴)—, —C(R⁴)=N— or —C(R⁴)₂C(R⁵)₂—;
J, K, L and M are independently selected from —C(R⁴)—, —C(R⁵)— or —N—, provided that at least one of J, K, L and M is not —N—;
R² is selected from: H, C₁–C₆ alkyl, (C₁–C₆ alkyl)carbonyl, (C₁–C₆ alkoxy)carbonyl; (C₁–C₆ alkyl)aminocarbonyl, C₃–C₆ alkenyl, C₃–C₇ cycloalkyl, C₄–C₁₁ cycloalkylalkyl, aryl, heteroaryl(C₁–C₆ alkyl)carbonyl, heteroarylcarbonyl, aryl C₁–C₆ alkyl, (C₁–C₆ alkyl)carbonyl, arylcarbonyl, C₁–C₆ alkylsulfonyl, arylsulfonyl, aryl(C₁–C₆ alkyl)sulfonyl, heteroarylsulfonyl, heteroaryl(C₁–C₆ alkyl)sulfonyl, aryloxycarbonyl, aryl(C₁–C₆ alkoxy)carbonyl, wherein said aryl groups are substituted with 0–2 substituents independently selected from the group consisting of C₁–C₄ alkyl, C₁–C₄ alkoxy, halo, CF₃, and nitro;
R³ is selected from: H, C₁–C₆ alkyl, C₃–C₇ cycloalkyl, C₄–C₁₁ cycloalkylalkyl, aryl, aryl(C₁–C₆ alkyl)-, or heteroaryl(C₁–C₆ alkyl)-;
R⁴ and R⁵ are independently selected from: H, C₁–C₄ alkoxy, NR²R³, halogen, NO₂, CN, CF₃, C₁–C₆ alkyl, C₃–C₆ alkenyl, C₃–C₇ cycloalkyl, C₄–C₁₁ cycloalkylalkyl, aryl, aryl(C₁–C₆ alkyl)-, (C₁–C₆ alkyl)carbonyl, (C₁–C₆ alkoxy)carbonyl, arylcarbonyl;
alternatively, when substituents on adjacent atoms, R⁴ and R⁵ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups independently selected from: C₁–C₄ alkyl, C₁–C₄ alkoxy, halo, cyano, amino, CF₃, or NO₂;
R⁶ is selected from: H, C₁–C₄ alkyl, or benzyl;
R⁷ and R⁸ are independently selected from: H, C₁–C₆ alkyl, C₃–C₇ cycloalkyl, C₄–C₁₁ cycloalkylalkyl, aryl, aryl(C₁–C₆ alkyl)-, or heteroaryl(C₀–C₆ alkyl)-;
U is selected from:
—(CH₂)ₙ—,
—(CH₂)ₘO—,
—(CH₂)ₘN(R⁷)—
—(CH₂)ₙS(O)ₚ—
—C(=O)(CH₂)ₙ—,
—(CH₂)ₘC(=O)—;
V is selected from:
—(CH₂)ₙ—,
—(CH₂)ₘO—(CH₂)ₙ—, —$(CH_2)_mN(R^7)(CH_2)_n$—,
—$(CH_2)_nS(O)_p(CH_2)_n$—,
—$(CH_2)_mN(R^7)C(=O)(CH_2)_n$—,
—$(CH_2)_mC(=O)N(R^7)(CH_2)_n$—,
—$(CH_2)_nC(=O)(CH_2)_n$—;

$R^9$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

$R^{10}$ is selected from: H, $CO_2R^{17}$, $C(=O)R^{17}$, $C(=O)NR^{17}R^{20}$, —$SO_2R^{17}$, —$SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{10a}$ is selected from: $CO_2R^{17}$, $C(=O)R^{17}$, $C(=O)NR^{17}R^{20}$, —$SO_2R^{17}$, —$SO_2NR^{17}R^{20}$, $C_1$–$C_6$ alkyl substituted with 0–1 $R^{15}$, $C_3$–$C_6$ alkenyl substituted with 0–1 $R^{15}$, $C_3$–$C_7$ cycloalkyl substituted with 0–1 $R^{15}$, $C_4$–$C_{11}$ cycloalkylalkyl substituted with 0–1 $R^{15}$, aryl substituted with 0–1 $R^{15}$ or 0–2 $R^{11}$, or aryl($C_1$–$C_6$ alkyl)- substituted with 0–1 $R^{15}$ or 0–2 $R^{11}$;

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is selected from:
  $C_1$–$C_4$ alkylene,
  —$(C(R^{12})_2)_qO(C(R^{12})_2)_q$—,
  —$(C(R^{12})_2)_qC(=O)(C(R^{12})_2)_q$—,
  —$(C(R^{12})_2)_qC(=O)N(R^{13})$—,
  —$C(=O)$—$N(R^{13})$—$(C(R^{12})_2)_q$—;

X is —$(C(R^{12})_2)_qC(R^{12})(R^{14})$—$C(R^{12})(R^{15})$—;
alternatively, W and X can be taken together to be

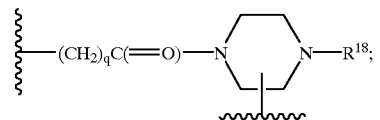

$R^{12}$ is selected from H, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl($C_1$–$C_6$ alkyl)-;

$R^{13}$ is selected from H, $C_1$–$C_6$ alkyl, $C_3$–$C_7$ cycloalkylmethyl, or aryl($C_1$–$C_6$ alkyl)-

$R^{14}$ is selected from: H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may optionally be substituted independently with 0–1 $R^{16}$ or 0–2 $R^{11}$;

$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may optionally be substituted independently with 0–2 $R^{11}$;

Y is —$COR^{19}$;

$R^{16}$ is selected from:
  —$N(R^{20})$—$C(=O)$—O—$R^{17}$,
  —$N(R^{20})$—$C(=O)$—$R^{17}$,
  —$N(R^{20})$—$C(=O)$—NH—$R^{17}$,
  —$N(R^{20})SO_2$—$R^{17}$, or
  —$N(R^{20})SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, arylaryl($C_1$–$C_6$ alkyl)-, heteroarylaryl($C_1$–$C_6$ alkyl)-, arylheteroaryl($C_1$–$C_6$ alkyl)-, heteroarylheteroaryl($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from: H, $C_1$–$C_9$ alkyl, $C_4$–$C_{11}$ cycloalkylalkyl, aryl, aryl($C_1$–$C_6$ alkyl), heteroaryl, heteroaryl($C_1$–$C_6$ alkyl) wherein said alkyl or aryl groups are substituted with 0–2 substituents selected from the group consisting of $C_1$–$C_4$ alkyl, $C_1$–$C_4$ alkoxy, OH, halo, $CF_3$, and nitro;
alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-; and k is 2, 3, 4, 5, or 6;
m is 1 or 2;
n is 0, 1, or 2;
p is 0, 1, or 2;
q is 0, 1, or 2; and
r is 0, 1, or 2;
provided that:
  n, q, and r are chosen such that the number of in-chain atoms between $R^1$ and Y is in the range of 8–18.

[16] Preferred compounds of the invention as described above are compounds of the Formula Id and pharmaceutically acceptable salt forms thereof wherein:
  Q" is selected from:

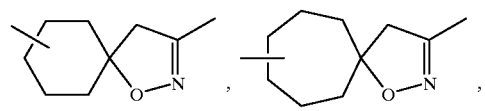

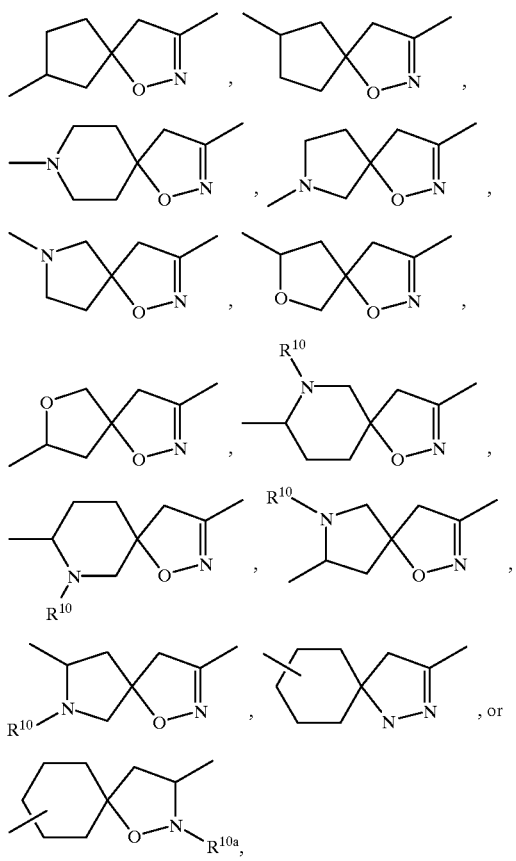

R[1] is selected from:

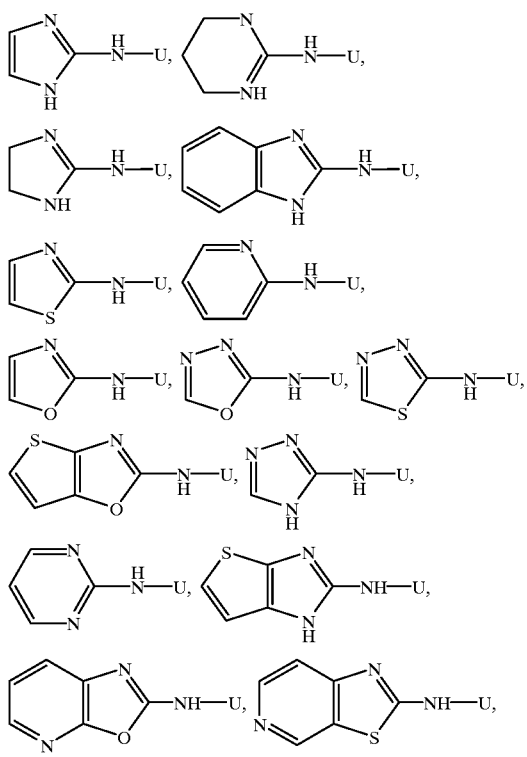

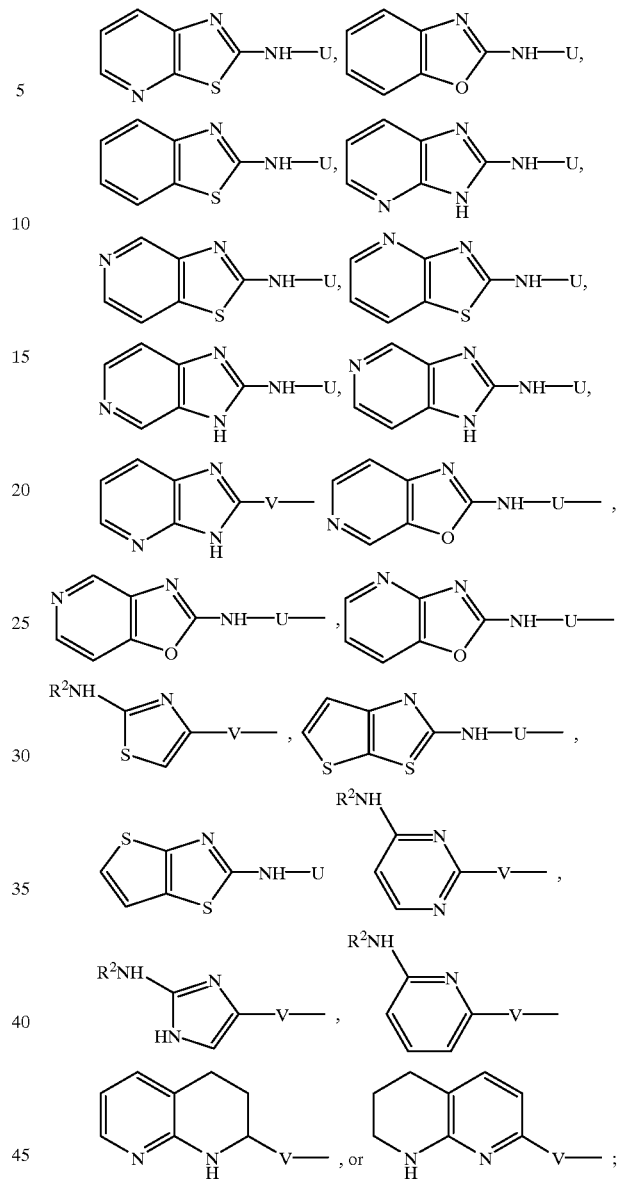

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

R[2] is selected from: H, $C_1$–$C_4$ alkyl or benzyl;

U is —$(CH_2)_n$—;

V is —$(CH_2)_n$—;

R[10] is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 R[15], $C_3$–$C_6$ alkenyl substituted with 0–1 R[15], $C_3$–$C_7$ cycloalkyl substituted with 0–1 R[15], $C_4$–$C_{11}$ cycloalkylalkyl substituted with 0–1 R[15], aryl substituted with 0–1 R[15] or 0–2 R[11], or aryl($C_1$–$C_6$ alkyl)- substituted with 0–1 R[15] or 0–2 R[11];

R[10a] is selected from: $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 R[15], $C_3$–$C_6$ alkenyl substituted with 0–1 R[15], $C_3$–$C_7$ cycloalkyl substituted with 0–1 R[15], $C_4$–$C_{11}$ cycloalkylalkyl substituted with 0–1 R[15], aryl substituted with 0–1 R[15] or 0–2 R[11], or aryl($C_1$–$C_6$ alkyl)- substituted with 0–1 R[15] or 0–2 R[11];

$R^{11}$ is selected from H, $C_1$–$C_4$ alkyl, $C_1$–$C_4$ alkoxy, aryl, aryl($C_1$–$C_6$ alkyl)-, ($C_1$–$C_4$ alkoxy)carbonyl, ($C_1$–$C_4$ alkyl)carbonyl, $C_1$–$C_4$ alkylsulfonyl, or $C_1$–$C_4$ alkylaminosulfonyl;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —C(=O)$R^{19}$;

$R^{16}$ is selected from:
—N($R^{20}$)—C(=O)—O—$R^{17}$,
—N($R^{20}$)—C(=O)—$R^{17}$, or
—N($R^{20}$)$SO_2$—$R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, arylaryl($C_1$–$C_6$ alkyl)-, heteroarylaryl($C_1$–$C_6$ alkyl)-, arylheteroaryl($C_1$–$C_6$ alkyl)-, heteroarylheteroaryl($C_1$–$C_6$ alkyl)-, heteroaryl, or aryl, wherein said aryl or heteroaryl groups are optionally substituted with 0–3 substituents independently selected from the group consisting of: $C_1$–$C_4$ alkyl, $C_1$–$C_4$ alkoxy, aryl, halo, cyano, amino, $CF_3$, and $NO_2$;

$R^{19}$ is —O—$(CH_2)_k$$N^+$($R^{22}$)($R^{23}$)($R^{24}$)$Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from: H, $C_1$–$C_6$ alkyl, $C_4$–$C_{11}$ cycloalkylalkyl, aryl, aryl($C_1$–$C_6$ alkyl), heteroaryl, heteroaryl($C_1$–$C_6$ alkyl) wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is H or $CH_3$;

k is 2–4; and n is 0–1.

[17] Further preferred compounds of the invention as described above are compounds of the Formula Id and pharmaceutically acceptable salt forms thereof wherein:

Q" is selected from:

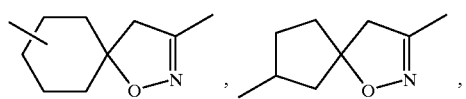

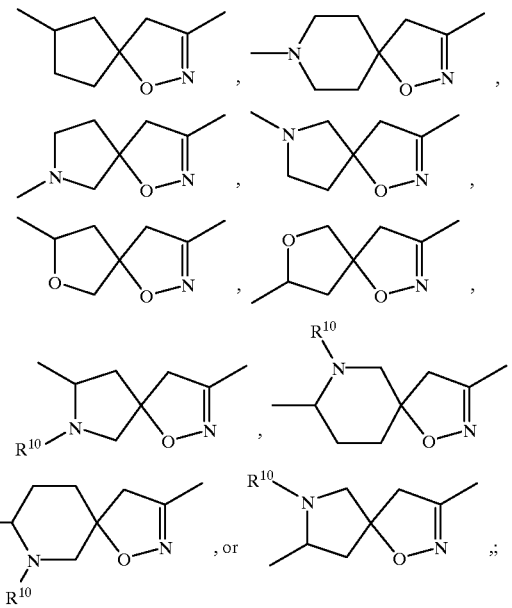

$R^1$ is selected from:

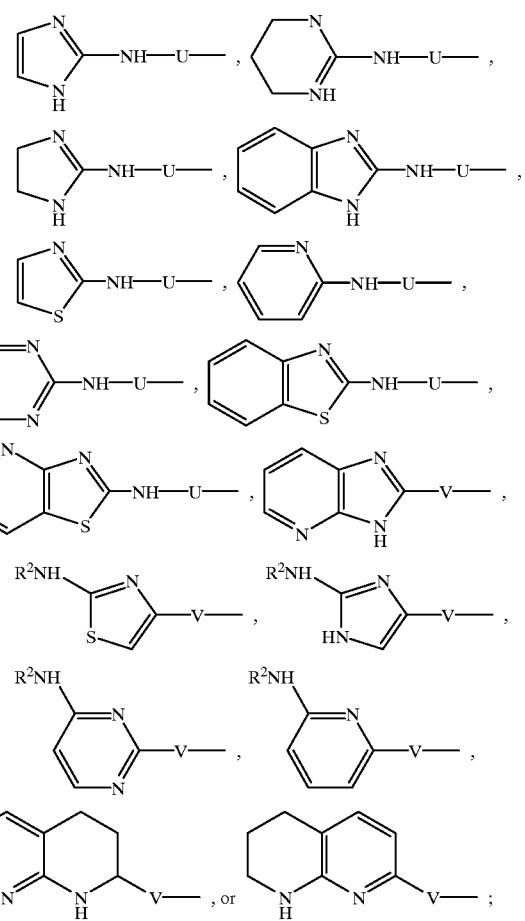

Y is —C(=O)$R^{19}$;

$R^{19}$ is —O—$(CH_2)_k$$N^+$($R^{22}$)($R^{23}$)($R^{24}$)$Z^-$;

51

Z⁻ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, methyl, ethyl, propyl, butyl, and $C_3$–$C_7$ cycloalkyl ($C_1$–$C_4$ alkyl)-;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{20}$ is H or $CH_3$;

k is 2; and n is 0–1.

[18] Specifically preferred compounds of the present invention are ammonium esters of compounds of the Formula Id, including enantiomeric forms, diasteriomeric forms or mixtures of enantiomeric or diasteriomeric forms thereof, and pharmaceutically acceptable salt forms thereof, wherein:

the ammonium ester is selected from:

(trimethylammonium)ethyl, (triethylammonium)ethyl, (diethylmethylammonium)ethyl,
(1-morpholinomethylammonium)ethyl,
(1-morpholinoethylammonium)ethyl,
(1-pyrrolidinomethylammonium)ethyl, and
(1-pyrrolidinoethylammoniumethyl ester; and the acid is selected from:

(S)-2-phenylsulfonylamino-3-[[[8-(2-pyridinylaminomethyl)-]-1-oxa-2-azaspiro-[4,5]-dec-2-en-3-yl]carbonylamino]propionic acid, (S)-2-benzyloxycarbonylamino-3-[[[8-(2-pyridinylaminomethyl)-]-1-oxa-2-azaspiro-[4,5]-dec-2-en-3-yl]carbonylamino]propionic acid, (S)-2-[(2,4,6-trimethylphenyl)sulfonyl]amino-3-[[[8-(2-pyridinylaminomethyl)-]-1-oxa-2-azaspiro-[4,5]-dec-2-en-3-yl]carbonylamino]propionic acid, (S)-2-[(3,5-dimethylisoxazol4-yl)sulfonyl]amino-3-[[[8-(2-pyridinylaminomethyl)-]-1-oxa-2-azaspiro-[4,5]-dec-2-en-3-yl]carbonylamino]propionic acid, (S)-2-phenylsulfonylamino-3-[[[8-[(6-aminopyridin-2-yl)methyl]-]-1-oxa-2,8-diazaspiro-[4,5]-dec-2-en-3-yl]carbonylamino]propionic acid, (S)-2-phenylsulfonylamino-3-[[[8-[(6-aminopyridin-2-yl)methyl]]-1-oxa-2,8-diazaspiro-[4,4]-non-2-en-3-yl]carbonylamino]propionic acid, (S)-2-phenylsulfonylamino-3-[[[8-(2-pyridinylaminomethyl)-]-1-oxa-2-azaspiro-[4,4]-non-2-en-3-yl]carbonylamino]propionic acid, (S)-2-phenylsulfonylamino-3-[[[8-[2-(4,5-dihydroimidazol-2-yl)aminomethyl]-]-1-oxa-2-azaspiro-[4,5]-dec-2-en-3-yl]carbonylamino]-propionic acid, (S)-2-[(2-methylphenyl)sulfonyl]amino-3-[[[8-(2-pyridinylaminomethyl)-]-1-oxa-2-azaspiro-[4,5]-dec-2-en-3-yl]carbonylamino]propionic acid, (S)-2-[(2-chloro-4-methylphenyl)sulfonyl]amino-3-[[[8-(2-pyridinylaminomethyl)-]-1-oxa-2-azaspiro-[4,5]-dec-2-en-3-yl]carbonylamino]propionic acid, (S)-2-[(4-biphenyl)sulfonyl]amino-3-[[[8-(2-pyridinylaminomethyl)-]-1-oxa-2-azaspiro-[4,5]-dec-2-en-3-yl]carbonylamino]propionic acid,

52

(S)-2-[(2-bromophenyl)sulfonyl]amino-3-[[[8-(2-pyridinylaminomethyl)-]-1-oxa-2-azaspiro-[4,5]-dec-2-en-3-yl]carbonylamino]propionic acid, (S)-2-[(2-naphthyl)sulfonyl]amino-3-[[[8-(2-pyridinylaminomethyl)-]-1-oxa-2-azaspiro-[4,5]-dec-2-en-3-yl]carbonylamino]propionic acid, (S)-2-[(1-naphthyl)sulfonyl]amino-3-[[[8-(2-pyridinylaminomethyl)-]-1-oxa-2-azaspiro-[4,5]-dec-2-en-3-yl]carbonylamino]propionic acid.

[19] A fourth embodiment of the present invention comprises compounds of Formula Ie:

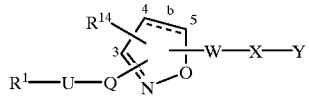

(Ie)

including enantiomeric or diastereomeric forms thereof, or mixtures of enantiomeric or diastereomeric forms thereof, or pharmaceutically acceptable salt forms thereof wherein:

b, the bond between carbon atoms numbered 4 and 5, is a carbon-carbon single or double bond;

$R^1$ is selected from:

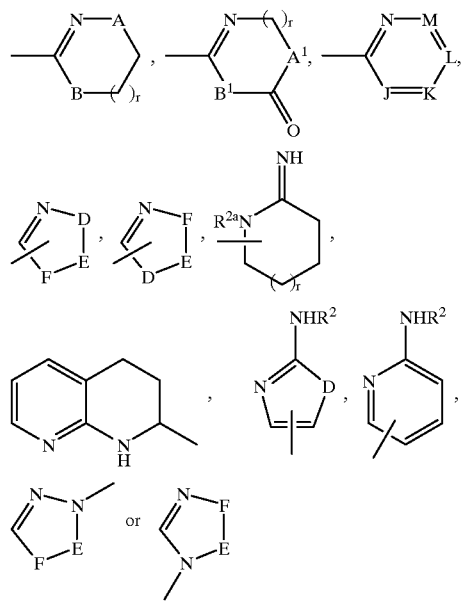

A and B are independently —$CH_2$—, —O—, —$N(R^2)$—, or —C(=O)—;

$A^1$ and $B^1$ are independently —$CH_2$— or —$N(R^3)$—;

D is —$N(R^{2a})$—, —O—, —S—, —C(=O)— or —$SO_2$—;

E—F is —$C(R^4)=C(R^5)$—, —$N=C(R^4)$—, —$C(R^4)=N$—, —$N=N$—, or —$C(R^4)_2C(R^5)_2$—;

J, K, L and M are independently selected from —$C(R^4)$— or —N—, provided that at least one of J, K, L and M is —$C(R^4)$—;

$R^2$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl $C_1$–$C_6$ alkyl, ($C_1$–$C_6$ alkyl)carbonyl, arylcarbonyl, $C_1$–$C_6$ alkylsulfonyl, arylsulfonyl, aryl($C_1$–$C_6$ alkyl)

sulfonyl, heteroarylsulfonyl, heteroaryl($C_1$–$C_6$ alkyl)sulfonyl, aryloxycarbonyl, aryl($C_1$–$C_6$ alkoxy)carbonyl, wherein said aryl groups are substituted with 0–2 substituents independently selected from the group consisting of $C_1$–$C_4$ alkyl, $C_1$–$C_4$ alkoxy, halo, $CF_3$, and nitro;

$R^{2a}$ is absent or $R^2$;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^{11}R^{20}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, $C_7$–$C_{11}$ arylalkyl, $C_2$–$C_7$ alkylcarbonyl, $C_7$–$C_{11}$ arylcarbonyl, $C_6$–$C_{10}$ aryl substituted with 0–2 substituents independently selected from the group consisting of $C_1$–$C_4$ alkyl, $C_1$–$C_4$ alkoxy, halo, $CF_3$, and nitro;

alternatively, $R^4$ and $R^5$ can be taken together with the carbon atoms to which they are attached to form a 5–7 membered carbocyclic or 5–7 membered heterocyclic aromatic or nonaromatic ring system, said carbocyclic or heterocyclic ring being optionally substituted with 0–2 substituents independently selected from the group consisting of $C_1$–$C_4$ alkyl, $C_1$–$C_4$ alkoxy, halo, $CF_3$, and nitro;

U is selected from:
—$(CH_2)_n$—,
—$(CH_2)_nO(CH_2)_m$—,
—$(CH_2)_nN(R^6)(CH_2)_m$—,
—$(CH_2)_nC(=O)(CH_2)_m$—,
—$(CH_2)_nS(O)_p(CH_2)_m$—,
—$(CH_2)_nNHNH(CH_2)_m$—,
—$N(R^6)C(=O)$—,
—$C(=O)N(R^6)$—, or
—$N(R^6)S(O)_p$—;

Q is selected from: —($C_1$–$C_4$ alkylene)-V—, —($C_2$–$C_4$ alkenylene)-V—, —($C_2$–$C_4$ alkynylene)-V—, -(phenyl)-V—, -(pyridyl)-V—, or -(pyridazinyl)-V—;

V is selected from:
—$(CH_2)_n$—,
—$(CH_2)_nO(CH_2)_m$—,
—$(CH_2)_nN(R^6)(CH_2)_m$—,
—$(CH_2)_nC(=O)(CH_2)_m$—,
—$(CH_2)_nS(O)_p(CH_2)_m$—,
—$(CH_2)_nNHNH(CH_2)_m$—,
—$N(R^6)C(=O)$—, or
—$C(=O)N(R^6)$—;

W is selected from:
—$(C(R^{12})_2)_qC(=O)N(R^{13})$—, —$C(=O)$—$N(R^{13})$—$(C(R^{12})_2)_q$—;

X is —$(CH_2)_q$—$CH(R^{28})$—$CH(R^{29})$—;

alternatively, W and X can be taken together to be

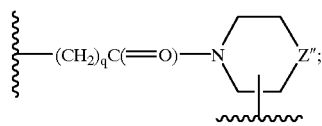

Y is —$COR^{19}$;

Z" is selected from —$CH(R^{29})$ or —$N(R^{36})$—;

$R^6$ is selected from H, $C_1$–$C_6$ alkyl, benzyl, or phenylethyl;

$R^7$ is selected from: H, $C_1$–$C_4$ alkyl, hydroxy, $C_1$–$C_4$ alkoxy, nitro, $C_1$–$C_4$ alkylcarbonyl, —$N(R^{11})R^{20}$, $CO_2R^{38a}$, $SO_2R^{11}$, $SO_2NR^{10}R^{11}$ or $OR^{10}$;

$R^{10}$ is selected from H, $C_1$–$C_{10}$ alkyl, or $C_7$–$C_{10}$ arylalkyl;

$R^{11}$ is selected from hydrogen, hydroxy, $C_1$–$C_8$ alkyl, $C_3$–$C_6$ alkenyl, $C_3$–$C_{11}$ cycloalkyl, $C_4$–$C_{11}$ cycloalkylmethyl, $C_1$–$C_6$ alkoxy, benzyloxy, $C_6$–$C_{10}$ aryl, heteroaryl, heteroarylalkyl, $C_7$–$C_{11}$ arylalkyl, adamantylmethyl, or $C_1$–$C_{10}$ alkyl substituted with 0–2 $R^{40}$;

alternatively, $R^{10}$ and $R^{11}$ when both are substituents on the same nitrogen atom (as in —$NR^{10}R^{11}$) can be taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl; said heterocycle being optionally substituted with 1–3 groups selected from: $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{12}$ is selected from H, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl ($C_1$–$C_6$ alkyl)-;

$R^{13}$ is selected from H, $C_3$–$C_7$ cycloalkylmethyl, aryl ($C_1$–$C_6$ alkyl)-, or $C_1$–$C_6$ alkyl substituted with 0–2 $R^{40}$;

$R^{14}$ is selected from: H, $CO_2R^{38a}$, $C(=O)R^{38a}$, $CONR^{38a}R^{37}$, —$SO_2R^{38a}$, —$SO_2NR^{38a}R^{37}$, $C_1$–$C_6$ alkyl substituted with 0–1 $R^{29}$, $C_3$–$C_6$ alkenyl substituted with 0–1 $R^{29}$, $C_3$–$C_7$ cycloalkyl substituted with 0–1 $R^{29}$, $C_4$–$C_{11}$ cycloalkylalkyl substituted with 0–1 $R^{29}$, aryl substituted with 0–1 $R^{29}$ or 0–2 $R^7$, or aryl($C_1$–$C_6$ alkyl)- substituted with 0–1 $R^{29}$ or 0–2 $R^7$;

$R^{19}$ is —$O$—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from: H, $C_1$–$C_9$ alkyl, $C_4$–$C_1$1 cycloalkylalkyl, aryl, aryl($C_1$–$C_6$ alkyl), heteroaryl, heteroaryl($C_1$–$C_6$ alkyl) wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, triphenylmethyl, methoxyphenyldiphenylmethyl, trimethylsilylethoxymethyoxy, $C_1$–$C_4$ alkoxycarbonyl, $C_1$–$C_6$ alkylcarbonyl, $C_1$–$C_6$ alkylsulfonyl, aryl($C_1$–$C_4$ alkyl)sulfonyl, arylsulfonyl, aryl, heteroarylcarbonyl, or heteroarylalkylcarbonyl, wherein said aryl groups are substituted with 0–3 substituents selected from the group consisting of: $C_1$–$C_4$ alkyl, $C_1$–$C_4$ alkoxy, halo, $CF_3$, and $NO_2$;

$R^{26}$ is selected from: H, $C_1$–$C_4$ alkyl, hydroxy, $C_1$–$C_4$ alkoxy, nitro, $C_1$–$C_6$ alkylcarbonyl, —N($R^{11}$)$R^{20}$, cyano, halo, $CF_3$, —S(O)$_p$$R^{10}$, $CO_2R^{38a}$, $CONR^{37}R^{38a}$, —$COR^{38a}$, $OR^{10}$, or aryl optionally substituted with 0–3 groups selected from halogen, $C_1$–$C_6$ alkoxy, $C_1$–$C_6$ alkyl, $CF_3$, S(O)$_m$Me, or —NMe$_2$;

$R^{28}$ is selected from: H, $R^{26}$, $C_1$–$C_{10}$ alkyl, substituted with 0–1 $R^{26}$, $C_2$–$C_{10}$ alkenyl, substituted with 0–1 $R^{26}$, $C_2$–$C_{10}$ alkynyl, substituted with 0–1 $R^{26}$, $C_3$–$C_8$ cycloalkyl, substituted with 0–1 $R^{26}$, aryl, substituted with 0–1 $R^{26}$ or, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl or morpholinyl, said heterocycle optionally substituted with 0–2 $R^7$;

$R^{29}$ is selected from: H or —N($R^{36}$)$R^{37}$;

$R^{36}$ is selected from:
—C(=O)—O—$R^{38a}$,
—C(=O)—$R^{38b}$,
—C(=O)N($R^{38b}$)$_2$,
—C(=O)NHSO$_2$$R^{38a}$,
—C(=O)NHC(=O)$R^{38b}$,
—C(=O)NHC(=O)O$R^{38a}$,
—C(=O)NHSO$_2$NH$R^{38b}$,
—C(=S)—NH—$R^{38b}$,
—SO$_2$—O—$R^{38a}$,
—SO$_2$—$R^{38a}$,
—SO$_2$—N($R^{38b}$)$_2$,
—SO$_2$—NHC(=O)O$R^{38b}$;

$R^{37}$ is selected from H or $C_1$–$C_4$ alkyl;

$R^{38a}$ is selected from: $C_1$–$C_8$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl),heteroaryl, or aryl, wherein said aryl or heteroaryl groups are optionally substituted with 0–2 $R^{39}$;

$R^{38b}$ is selected from $R^{38a}$ or H;

$R^{39}$ is selected from H, halogen, $CF_3$, $CO_2$H, CN, $NO_2$, $NR^{11}R^{20}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl($C_1$–$C_6$ alkyl)-, $C_1$–$C_6$ alkoxy, $OCF_3$, or $C_1$–$C_4$ alkoxycarbonyl, aryl, —O— aryl, —SO$_2$-aryl, heteroaryl, or —SO$_2$-heteroaryl, wherein said aryl and heteroaryl groups may be substituted with 0–4 groups selected from hydrogen, halogen, $CF_3$, $C_1$–$C_3$ alkyl, or $C_1$–$C_3$ alkoxy;

$R^{40}$ is selected from H, $C_1$–$C_6$ alkyl, $C_3$–$C_7$ cycloalkyl, $C_4$–$C_{10}$ cycloalkylalkyl, ($C_1$–$C_4$ alkyl)carbonyl, aryl, or aryl($C_1$–$C_6$ alkyl)-;

k is 2, 3, 4, 5, or 6;
m is 0, 1, or 2;
n is 0, 1, 2, 3, or 4;
p is 0, 1, or 2;
q is 0 or 1; and
r is 0, 1, or 2;

with the following provisos:
(1) when b is a double bond, V and U are not —(CH$_2$)—; and
(2) n, m and q are chosen such that the number of atoms connecting $R^1$ and Y is in the range of 8–14; and
(3) when Q is -(phenyl)-V—, then either: U is not a direct bond (i.e., U is not —(CH$_2$)$_n$— where n=0) or V is not a direct bond (i.e., V is not —(CH$_2$)$_n$— where n=0).

[20] Preferred compounds of the invention as described above are compounds of the Formula Ie:

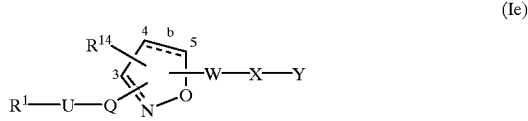

(Ie)

including enantiomeric or diastereomeric forms thereof, or mixtures of enantiomeric or diastereomeric forms thereof, or pharmaceutically acceptable salt forms thereof wherein:

b, the bond between carbon atoms numbered 4 and 5, is a carbon-carbon single or double bond;

$R^1$ is selected from:

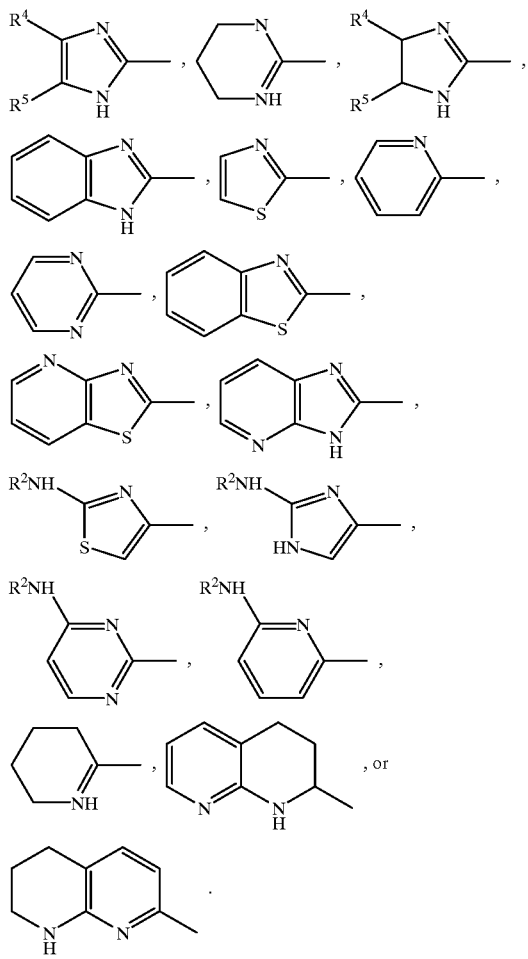

U is selected from:
—(CH$_2$)$_n$—,
—N($R^6$)(CH$_2$)$_m$—,
—N($R^6$)C(=O)—,
—C(=O)N($R^6$)—, or
—N($R^6$)S(O)$_p$—;

Q is selected from: —($C_1$–$C_4$ alkylene)-V—, —($C_2$–$C_4$ alkenylene)-V—, —($C_2$–$C_4$ alkynylene)-V—, -(phenyl)-V—, -(pyridyl)-V—, or -(pyridazinyl)-V—;

V is selected from:
—(CH$_2$)$_n$—,
—(CH$_2$)$_n$O(CH$_2$)$_m$—,

—$(CH_2)_nN(R^6)(CH_2)_m$—,
—$N(R^6)C(=O)$—, or
—$C(=O)N(R^6)$—;

W is selected from:
—$(CH_2)_qC(=O)N(R^{13})$—, or
—$C(=O)$—$N(R^{13})$—$(CH_2)_q$;

X is —$(CH_2)_q$—$CH(R^{28})$—$CH(R^{29})$—;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{20}$ is H or $CH_3$;

$R^{22}$, $R^{23}$ and $R^{24}$ are independently selected from: H, $C_1$–$C_6$ alkyl, $C_4$–$C_{11}$ cycloalkylalkyl, aryl, aryl($C_1$–$C_6$ alkyl), heteroaryl, heteroaryl($C_1$–$C_6$ alkyl) wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{26}$ is selected from: H, $C_1$–$C_4$ alkyl, hydroxy, $C_1$–$C_4$ alkoxy, nitro, $C_1$–$C_6$ alkylcarbonyl, —$N(R^{11})R^{20}$, cyano, halo, $CF_3$, —$S(O)_pR^{10}$, $CO_2R^{38a}$, $CONR^{37}R^{38a}$, $COR^{38a}$, $OR^{10}$, or aryl optionally substituted with 0–3 groups selected from halogen, $C_1$–$C_6$ alkoxy, $C_1$–$C_6$ alkyl, $CF_3$, $S(O)_mMe$, or —$NMe_2$;

$R^{28}$ is selected from: H, $CONR^{37}R^{38a}$, —$CO_2R^{38a}$, —$COR^{38a}$ $C_1$–$C_{10}$ alkyl, substituted with 0–1 $R^{26}$, $C_2$–$C_{10}$ alkenyl, substituted with 0–1 $R^{26}$, $C_2$–$C_{10}$ alkynyl, substituted with 0–1 $R^{26}$, $C_3$–$C_8$ cycloalkyl, substituted with 0–1 $R^{26}$, aryl, substituted with 0–1 $R^{26}$ or, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, 3H-indolyl, carbazolyl, pyrrolidinyl, piperidinyl, isoxazolinyl, isoxazolyl or morpholinyl, said heterocycle optionally substituted with 0–2 $R^7$;

$R^{36}$ is selected from:
—$C(=O)$—O—$R^{38a}$,
—$C(=O)$—$R^{38b}$,
—$SO_2$—$R^{38a}$ or,
—$SO_2$—$N(R^{38b})_2$; and k is 2–4;
m is 0–2;
n is 0–4;
p is 0–2;
q is 0–1; and
r is 0–2;
with the proviso that n, m, and q are chosen such that the number of atoms connecting $R^1$ and $COR^{19}$ is in the range of 8–14.

[21] Further preferred compounds of the invention as described above are compounds of the Formula IIg, IIh or IIi:

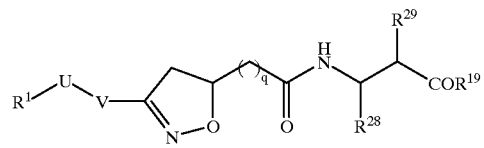

(IIg)

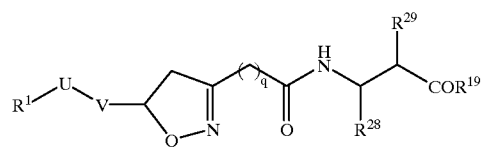

(IIh)

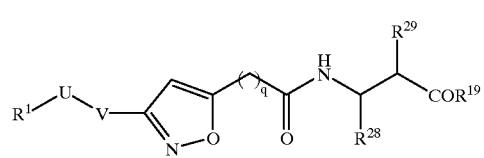

(IIi)

including enantiomeric or diasteriomeric forms thereof, or mixtures of enantiomeric or diasteriomeric forms thereof, or pharmaceutically acceptable salt forms thereof wherein:

$R^1$—U taken together are selected from:

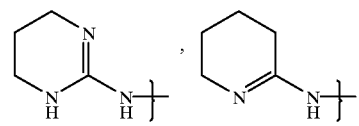

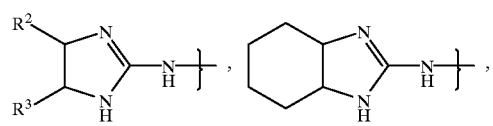

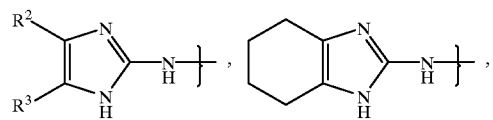

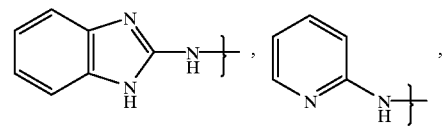

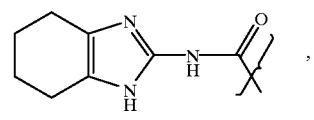

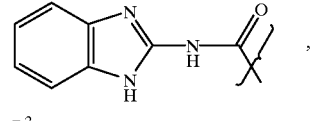

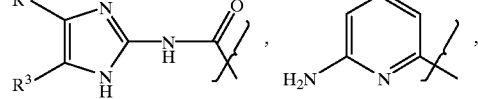

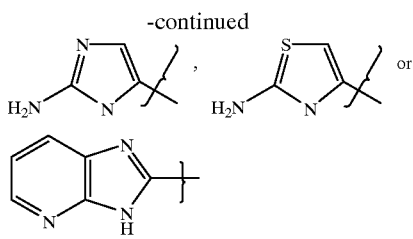

R² and R³ are independently selected from: H, $C_1$–$C_4$ alkoxy, halogen, $C_1$–$C_6$ alkyl, or $C_3$–$C_6$ alkenyl;

Q is selected from: —$(CH_2)_n$—, —($C_1$–$C_6$ alkylene)—V—, —($C_2$–$C_7$ alkenylene)—V—, or -(phenyl)-V—;

V is selected from: —$(CH_2)_n$—, —O—, —N($R^{12}$)—, —N($R^{10}$)C(=O)—, or —C(=O)N($R^{10}$)—;

$R^7$ is selected from: H, hydroxy, $C_1$–$C_4$ alkoxy, $C_1$–$C_4$ alkylcarbonyl, —$NR^{10}R^{11}$, $CO_2R^{18a}$, $SO_2NR^{10}R^{11}$, or $OR^{10}$;

$R^{10}$ is selected from H or $C_1$–$C_{10}$ alkyl;

$R^{11}$ is selected from hydrogen, hydroxy, $C_1$–$C_8$ alkyl, $C_3$–$C_6$ alkenyl, $C_3$–$C_{11}$ cycloalkyl, $C_4$–$C_{11}$ cycloalkylmethyl, $C_1$–$C_6$ alkoxy, benzyloxy, $C_6$–$C_{10}$ aryl, heteroaryl, heteroarylalkyl, $C_7$–$C_{11}$ arylalkyl, or adamantylmethyl;

$R^{13}$ is selected from: H, hydroxy, $C_1$–$C_{10}$ alkoxy, N($R^{10}$)$R^{11}$, —N($R^{16}$)$R^{17}$, $C_1$–$C_{10}$ alkyl substituted with 0–2 $R^7$, aryl substituted with 0–3 $R^7$, heteroaryl substituted with 0–2 $R^7$, or $C_1$–$C_6$ alkylcarbonyl;

$R^{19}$ is —O—$(CH_2)_k N^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{20}$ is H or $CH_3$;

$R^{22}$, $R^{23}$, and $R^{24}$ are independently selected from H, methyl, ethyl, propyl, butyl, and $C_3$–$C_7$ cycloalkyl ($C_1$–$C_4$ alkyl)-;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{28}$ is selected from: H, $CONR^{17}R^{18a}$, $C_1$–$C_{10}$ alkyl, $C_2$–$C_{10}$ alkenyl, $C_2$–$C_{10}$ alkynyl, $C_3$–$C_8$ cycloalkyl, pyridinyl, or aryl, wherein said aryl or pyridinyl groups are optionally substituted with 0–3 substituents selected from the group consisting of: $C_1$–$C_4$ alkyl, $C_1$–$C_4$ alkoxy, aryl, halo, cyano, $CF_3$, and $NO_2$.

$R^{29}$ is H or —$NHR^{36}$;

$R^{36}$ is selected from: —C(=O)—O—$R^{38a}$, —$SO_2$—$R^{38a}$ or, —$SO_2$ —$NHR^{38a}$;

$R^{38a}$ is selected from: $C_1$–$C_8$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl), heteroaryl, or aryl, wherein said aryl or heteroaryl groups are optionally substituted with 0–2 $R^{39}$;

$R^{39}$ is selected from: H, Br, F, Cl, $CF_3$, CN, $NO_2$, $NHR^{11}$, $C_1$–$C_4$ alkyl, aryl, aryl($C_1$–$C_4$ alkyl)-, $C_1$–$C_4$ alkoxy, $C_1$–$C_4$ alkoxycarbonyl, or —O—aryl, wherein said aryl groups are optionally substituted with 0–3 substituents selected from a group consisting of halogen, $CF_3$, $C_1$–$C_3$ alkyl, or $C_1$–$C_3$ alkoxy;

k is 2;
n is 0–4; and
q is 0–1;

with the proviso that n, and q are chosen such that the number of atoms connecting $R^1$ and $COR^{19}$ is in the range of 8–14.

[22] Specifically preferred compounds of the present invention are ammonium esters of compounds of the Formula Ie, including enantiomeric forms, diasteriomeric forms or mixtures of enantiomeric or diasteriomeric forms thereof, and pharmaceutically acceptable salt forms thereof, wherein:

the ammonium ester is selected from: (trimethylammonium)ethyl, (triethylammonium)ethyl, (diethylmethylammonium)ethyl, (1-morpholinomethylammonium)ethyl, (1-morpholinoethylammonium)ethyl, (1-pyrrolidinomethylammonium)ethyl, and (1-pyrrolidinoethylammoniummethyl ester; and the acid is selected from:

3-[3-[3-(imidazolin-2-ylamino)propyl]isoxazolin-5-ylmethylcarbonylamino]-2-(benzyloxycarbonylamino)-propionic acid, 3-[3-[3-(imidazolin-2-ylamino)propyl]isoxazolin-5-ylmethylcarbonylamino]-2-(n-butyloxycarbonylamino) propionic acid, 3-[3-[3-(imidazolin-2-ylamino)propyl]isoxazolin-5-ylmethylcarbonylamino]-2-(phenylsulfonylamino) propionic acid, 3-[3-[3-(imidazolin-2-ylamino)propyl]isoxazolin-5-ylmethylcarbonylamino]-2-(n-butylsulfonylamino)-propionic acid, 3-[3-[3-(tetrahydropyrimid-2-ylamino)propyl]-isoxazolin-5-ylmethylcarbonylamino]-2-(benzyloxycarbonylamino) propionic acid, 3-[3-[3-(tetrahydropyrimid-2-ylamino)propyl]-isoxazolin-5-ylmethylcarbonyl amino]-2-(n-butyloxycarbonylamino)propionic acid, 3-[3-[3-(tetrahydropyrimid-2-ylamino)propyl]-isoxazolin-5-ylmethylcarbonylamino]-2-(phenylsulfonylamino) propionic acid, 3-[3-[3-(tetrahydropyrimid-2-ylamino)propyl]-isoxazolin-5-ylmethylcarbonylamino]-2-(n-butylsulfonyl) aminopropionic acid, 3-[3-[4-(imidazolin-2-ylamino)butyl]isoxazolin-5-ylcarbonylamino]-2-(benzyloxycarbonylamino)-propionic acid, 3-[3-[4-(imidazolin-2-ylamino)butyl]isoxazolin-5-ylcarbonylamino]-2-(n-butyloxycarbonyl-amino) propionic acid, 3-[3-[4-(imidazolin-2-ylamino)butyl]isoxazolin-5-ylcarbonylamino]-2-(phenylsulfonylamino)-propionic acid, 3-[3-[4-(imidazolin-2-ylamino)butyl]isoxazolin-5-ylcarbonylamino]-2-(n-butylsulfonylamino)-propionic acid, 3-[3-[4-(tetrahydropyrimid-2-ylamino)butyl]-isoxazolin-5-ylcarbonylamino]-2-(benzyloxycarbonylamino)propionic acid, 3-[3-[4-(tetrahydropyrimid-2-ylamino)butyl]-isoxazolin-5-ylcarbonyl amino]-2-(n-butyloxycarbonylamino) propionic acid, 3-[3-[4-(tetrahydropyrimid-2-ylamino)butyl]-isoxazolin-5-ylcarbonylamino]-2-(phenylsulfonylamino)propionic acid, 3-[3-[4-(tetrahydropyrimid-2-ylamino)butyl]-isoxazolin-5-ylcarbonylamino]-2-(n-butylsulfonyl)aminopropionic acid, 3-[3-[3-(imidazolin-2-ylamino)propyl]isoxazolin-5-ylcarbonylamino]-2-(benzyloxycarbonylamino)propionic acid,
3-[3-[3-(imidazolin-2-ylamino)propyl]isoxazolin-5-ylcarbonylamino]-2-(phenylsulfonylamino)propionic acid,
3-[3-[3-(tetrahydropyrimid-2-ylamino)propyl]-isoxazolin-5-ylcarbonylamino]-2-(benzyloxycarbonylamino)propionic acid,
3-[3-[3-(tetrahydropyrimid-2-ylamino)propyl]-isoxazolin-5-ylcarbonylamino]-2-(phenylsulfonylamino)propionic acid,
3-[3-[3-(2-aminothiazol-4-yl)propyl]isoxazolin-5-ylcarbonylamino]-2-(phenylsulfonylamino)propionic acid,
3-[3-[3-(2-aminothiazol-4-yl)propyl]isoxazolin-5-ylcarbonylamino]-2-(benzyloxycarbonylamino)propionic acid,
3-[3-[4-(imidazolin-2-ylamino)butyl]isoxazolin-5-ylcarbonylamino]-2-((2,4,6-trimethylphenyl)sulfonylamino)propionic acid,
3-[3-[4-(tetrahydropyrimid-2-ylamino)butyl]-isoxazolin-5-ylcarbonylamino]-2-((2,4,6-trimethylphenyl)sulfonylamino)propionic acid,
3-[3-[4-(imidazol-2-ylamino)butyl]isoxazolin-5-ylcarbonylamino]-2-(benzyloxycarbonylamino)propionic acid,
3-[3-[4-(imidazol-2-ylamino)butyl]isoxazolin-5-ylcarbonylamino]-2-(phenylsulfonylamino)-propionic acid,
3-[3-[4-(imidazol-2-ylamino)butyl]isoxazolin-5-ylcarbonylamino]-2-((2,6-dichlorophenyl)-sulfonylamino)propionic acid,
3-[3-[4-(imidazol-2-ylamino)butyl]isoxazolin-5-ylcarbonylamino]-2-((2,4,6-trimethylphenyl)sulfonylamino)propionic acid,
3-[3-[4-(imidazol-2-ylamino)butyl]isoxazolin-5-ylcarbonylamino]-2-((4-biphenyl)sulfonyl-amino)propionic acid,
3-[3-[4-(imidazol-2-ylamino)butyl]isoxazolin-5-ylcarbonylamino]-2-(1-naphthylsulfonylamino)propionic acid,
3-[3-[3-(imidazol-2-ylamino)propyl]isoxazolin-5-ylmethylcarbonylamino]-2-benzyloxycarbonylamino)propionic acid,
3-[3-[3-(imidazol-2-ylamino)propyl]isoxazolin-5-ylmethylcarbonylamino]-2-(phenylsulfonylamino)propionic acid,
3-[3-[3-(imidazol-2-ylamino)propyl]isoxazolin-5-ylmethylcarbonylamino]-2-((2,6-dichlorophenyl)sulfonylamino)propionic acid,
3-[3-[3-(imidazol-2-ylamino)propyl]isoxazolin-5-ylmethylcarbonylamino]-2-((2,4,6-trimethylphenyl)sulfonylamino)-propionic acid,
3-[3-[3-(imidazol-2-ylamino)propyl]isoxazolin-5-ylmethylcarbonylamino]-2-((4-biphenyl)-sulfonylamino)propionic acid,
3-[3-[3-(imidazol-2-ylamino)propyl]isoxazolin-5-ylmethylcarbonylamino]-2-(1-naphthylsulfonylamino)propionic acid,
3-[3-[2-(imidazol-2-ylamino)ethyl]isoxazolin-5-ylcarbonylamino]-2-(benzyloxycarbonylamino)propionic acid,
3-[3-[2-(imidazol-2-ylamino)ethyl]isoxazolin-5-ylcarbonylamino]-2-(phenylsulfonylamino)-propionic acid,
3-[3-[2-(imidazol-2-ylamino)ethyl]isoxazolin-5-ylcarbonylamino]-2-((2,6-dichlorophenyl)-sulfonylamino)propionic acid,
3-[3-[2-(imidazol-2-ylamino)ethyl]isoxazolin-5-ylcarbonylamino]-2-((2,4,6-trimethylphenyl)sulfonylamino)propionic acid,
3-[3-[2-(imidazol-2-ylamino)ethyl]isoxazolin-5-ylcarbonylamino]-2-((4-biphenyl)sulfonyl-amino)propionic acid,
3-[3-[2-(imidazol-2-ylamino)ethyl]isoxazolin-5-ylcarbonylamino]-2-(1-naphthylsulfonylamino)propionic acid,
3-[3-[3-(imidazol-2-ylaminocarbonyl)propyl]isoxazolin-5-ylcarbonylamino]-2-((2,4,6-trimethylphenyl)sulfonylamino)-propionic acid,
3-[3-[3-(2-aminoimidazol-4-yl)propyl]isoxazolin-5-ylcarbonylamino]-2-((2,4,6-trimethylphenyl)sulfonylamino)propionic acid,
3-[3-[2-(2-aminoimidazol-4-yl)ethyl]isoxazolin-5-ylmethylcarbonylamino]-2-((2,4,6-trimethylphenyl)sulfonylamino)-propionic acid,
3-[3-[4-(benzimidazol-2-ylamino)butyl]isoxazolin-5-ylcarbonylamino]-2-((2,4,6-trimethylphenyl)sulfonylamino)propionic acid,
3-[3-[3-(benzimidazol-2-ylamino)propyl]isoxazolin-5-ylmethylcarbonylamino]-2-((2,4,6-trimethylphenyl)sulfonylamino)propionic acid,
3-[3-[3-(benzimidazol-2-ylaminocarbonyl)propyl]isoxazolin-5-ylcarbonylamino]-2-((2,4,6,trimethylphenyl)sulfonylamino)-propionic acid,
3-[3-[4-(4-methylimidazol-2-ylamino)butyl]-isoxazolin-5-ylcarbonylamino]-2-((2,4,6-trimethylphenyl)sulfonylamino)-propionic acid,
3-[3-[3-(4-methylimidazol-2-ylamino)propyl]-isoxazolin-5-ylmethylcarbonylamino]-2-((2,4,6-trimethylphenyl)sulfonylamino)propionic acid,
3-[3-[4-(4,5-dimethylimidazol-2-ylamino)butyl]-isoxazolin-5-ylcarbonylamino]-2-((2,4,6,trimethylphenyl)sulfonylamino)-propionic acid,
3-[3-[3-(4,5-dimethylimidazol-2-ylamino)propyl]-isoxazolin-5-ylmethylcarbonylamino]-2-((2,4,6,trimethylphenyl)sulfonylamino)-propionic acid,
3-[3-[3-(4,5-dimethylimidazol-2-ylaminocarbonyl)propyl]-isoxazolin-5-ylcarbonylamino]-2-((2,4,6,trimethylphenyl)sulfonylamino)-propionic acid,
3-[3-[4-(4,5,6,7-tetrahydrobenzimidazol-2-ylamino)butyl]isoxazolin-5-ylcarbonylamino]-2-((2,4,6,trimethylphenyl)sulfonylamino)-propionic acid,
3-[3-[3-(4,5,6,7-tetrahydrobenzimidazol-2-ylamino)propyl]isoxazolin-5-ylmethylcarbonylamino]-2-((2,4,6,trimethylphenyl)sulfonyl-amino)propionic acid,
3-[3-[4-(pyridin-2-ylamino)butyl]isoxazolin-5-ylcarbonylamino]-2-((2,4,6-trimethylphenyl)sulfonylamino)propionic acid,
3-[3-[3-(pyridin-2-ylamino)propyl]isoxazolin-5-ylcarbonylamino]-2-((2,4,6-trimethylphenyl)sulfonylamino)propionic acid,
3-[3-[3-(2-pyridin-6-yl)propyl]isoxazolin-5-ylcarbonylamino]-2-((2,4,6-trimethylphenyl)sulfonylamino)propionic acid,
3-[3-[2-(2-aminopyridin-6-yl)ethyl]isoxazolin-5-ylmethylcarbonylamino]-2-((2,4,6-trimethylphenyl)sulfonylamino)-propionic acid,
3-[3-[3-(7-azabenzimidazol-2-yl)propyl]isoxazolin-5-ylcarbonylamino]-2-((2,4,6-trimethylphenyl)sulfonylamino)-propionic acid,
3-[5-[3-(imidazolin-2-ylamino)propyl]isoxazolin-3-ylmethylcarbonylamino]-2-(benzyloxycarbonylamino)propionic acid,
3-[5-[3-(imidazolin-2-ylamino)propyl]isoxazolin-3-ylmethylcarbonylamino]-2-(n-butyloxycarbonylamino)propionic acid, 3-[5-[3-(imidazolin-2-ylamino)propyl]isoxazolin-3-ylmethylcarbonylamino]-2-(phenylsulfonylamino) propionic acid,
3-[5-[3-(imidazolin-2-ylamino)propyl]isoxazolin-3-ylmethylcarbonylamino]-2-(2,4,6-trimethylphenylsulfonylamino)propionic acid,
3-[5-[3-(imidazolin-2-ylamino)propyl]isoxazolin-3-ylmethylcarbonylamino]-2-(n-butylsulfonylamino)-propionic acid,
3-[5-[3-(tetrahydropyrimid-2-ylamino)propyl]-isoxazolin-3-ylmethylcarbonylamino]-2-(benzyloxycarbonylamino) propionic acid,
3-[5-[3-(tetrahydropyrimid-2-ylamino)propyl]-isoxazolin-3-ylmethylcarbonylamino]-2-(n-butyloxycarbonylamino) propionic acid,
3-[5-[3-(tetrahydropyrimid-2-ylamino)propyl]-isoxazolin-3-ylmethylcarbonylamino]-2-(phenylsulfonylamino) propionic acid,
3-[5-[3-(tetrahydropyrimid-2-ylamino)propyl]-isoxazolin-3-ylmethylcarbonylamino]-2-(2,4,6-trimethylphenylsulfonylamino)propionic acid,
3-[5-[3-(tetrahydropyrimid-2-ylamino)propyl]-isoxazolin-3-ylmethylcarbonylamino]-2-(n-butylsulfonyl) aminopropionic acid,
3-[5-[4-(imidazolin-2-ylamino)butyl]isoxazolin-3-ylcarbonylamino]-2-(benzyloxycarbonylamino)-propionic acid,
3-[5-[4-(imidazolin-2-ylamino)butyl]isoxazolin-3-ylcarbonylamino]-2-(n-butyloxycarbonyl-amino) propionic acid,
3-[5-[4-(imidazolin-2-ylamino)butyl]isoxazolin-3-ylcarbonylamino]-2-(phenylsulfonylamino)propionic acid,
3-[5-[4-(imidazolin-2-ylamino)butyl]isoxazolin-3-ylcarbonylamino]-2-(n-butylsulfonylamino)propionic acid,
3-[5-[4-(tetrahydropyrimid-2-ylamino)butyl]-isoxazolin-3-ylcarbonylamino]-2-(benzyloxycarbonylamino)propionic acid,
3-[5-[4-(tetrahydropyrimid-2-ylamino)butyl]-isoxazolin-3-ylcarbonylamino]-2-(n-butyloxycarbonylamino) propionic acid,
3-[5-[4-(tetrahydropyrimid-2-ylamino)butyl]-isoxazolin-3-ylcarbonylamino]-2-(phenylsulfonylamino)propionic acid,
3-[5-[4-(tetrahydropyrimid-2-ylamino)butyl]-isoxazolin-3-ylcarbonylamino]-2-(n-butylsulfonyl)aminopropionic acid,
3-[5-[3-(imidazol-2-ylamino)propyl]isoxazolin-3-ylcarbonylamino]-2-(benzyloxycarbonylamino)-propionic acid,
3-[5-[3-(imidazolin-2-ylamino)propyl]isoxazolin-3-ylcarbonylamino]-2-(n-propyloxycarbonyl-amino) propionic acid,
3-[5-[3-(imidazolin-2-ylamino)propyl]isoxazolin-3-ylcarbonylamino]-2-(phenylsulfonylamino)propionic acid,
3-[5-[3-(imidazolin-2-ylamino)propyl]isoxazolin-3-ylcarbonylamino]-2-(n-propylsulfonylamino)propionic acid,
3-[5-[3-(tetrahydropyrimid-2-ylamino)propyl]-isoxazolin-3-ylcarbonylamino]-2-(benzyloxycarbonylamino) propionic acid,
3-[5-[3-(tetrahydropyrimid-2-ylamino)propyl]-isoxazolin-3-ylmethylcarbonylamino]-2-(n-propyloxycarbonylamino)propionic acid,
3-[5-[3-(tetrahydropyrimid-2-ylamino)propyl]-isoxazolin-3-ylcarbonylamino]-2-(phenylsulfonylamino)propionic acid,
3-[5-[3-(tetrahydropyrimid-2-ylamino)propyl]-isoxazolin-3-ylcarbonylamino]-2-(n-propylsulfonyl)aminopropionic acid,
3-[5-[2-(imidazolin-2-ylamino)ethyl]isoxazolin-3-ylcarbonylamino]-2-(phenylsulfonylamino)-propionic acid,
3-[5-[4-(pyridin-2-ylamino)butyl]isoxazolin-3-ylcarbonylamino]-2-(phenylsulfonylamino)-propionic acid,
3-[5-[4-(pyridin-2-ylamino)butyl]isoxazolin-3-ylcarbonylamino]-2-(2,6-dichlorophenyl-sulfonylamino) propionic acid,
3-[5-[4-(pyridin-2-ylamino)butyl]isoxazolin-3-ylcarbonylamino]-2-(2,4,6-trimethylphenyl-sulfonylamino)propionic acid,
3-[5-[4-(pyridin-2-ylamino)butyl]isoxazolin-3-ylcarbonylamino]-2-(4-biphenylsulfonylamino)propionic acid,
3-[5-[4-(pyridin-2-ylamino)butyl]isoxazolin-3-ylcarbonylamino]-2-(1-naphthylsulfonyl-amino) propionic acid,
3-[5-[3-(2-aminopyridin-6-yl)propyl]isoxazolin-3-ylcarbonylamino]-2-(2,4,6-trimethylphenylsulfonylamino)propionic acid,
3-[5-[4-(imidazol-2-ylamino)butyl]isoxazolin-3-ylcarbonylamino]-2-(phenylsulfonylamino)-propionic acid,
3-[5-[4-(imidazol-2-ylamino)butyl]isoxazolin-3-ylcarbonylamino]-2-(2,6-dichlorophenyl-sulfonylamino) propionic acid,
3-[5-[4-(imidazol-2-ylamino)butyl]isoxazolin-3-ylcarbonylamino]-2-(2,4,6-trimethylphenyl-sulfonylamino)propionic acid,
3-[5-[4-(imidazol-2-ylamino)butyl]isoxazolin-3-ylcarbonylamino]-2-(4-biphenylsulfonyl-amino) propionic acid,
3-[5-[4-(imidazol-2-ylamino)butyl]isoxazolin-3-ylcarbonylamino]-2-(1-naphthylsulfonyl-amino) propionic acid,
3-[5-[3-(2-aminoimidazol-4-yl)propyl]isoxazolin-3-ylcarbonylamino]-2-(phenylsulfonylamino)-propionic acid,
3-[5-[3-(2-aminoimidazol-4-yl)propyl]isoxazolin-3-ylcarbonylamino]-2-(2,6-dichlorophenyl-sulfonylamino) propionic acid,
3-[5-[3-(2-aminoimidazol-4-yl)propyl]isoxazolin-3-ylcarbonylamino]-2-(2,4,6-trimethylphenylsulfonylamino)propionic acid,
3-[5-[3-(2-aminoimidazol-4-yl)propyl]isoxazolin-3-ylcarbonylamino]-2-(4-biphenylsulfonylamino)propionic acid,
3-[5-[3-(2-aminoimidazol-4-yl)propyl]isoxazolin-3-ylcarbonylamino]-2-(1-naphthylsulfonylamino)propionic acid,
3-[5-[2-(imidazol-2-ylamino)ethyl]isoxazolin-3-ylcarbonylamino]-2-(phenylsulfonylamino)-propionic acid,
3-[5-[2-(imidazol-2-ylamino)ethyl]isoxazolin-3-ylcarbonylamino]-2-(2,6-dichlorophenyl-sulfonylamino) propionic acid,
3-[5-[2-(imidazol-2-ylamino)ethyl]isoxazolin-3-ylcarbonylamino]-2-(2,4,6-trimethylphenyl-sulfonylamino)propionic acid,
3-[5-[2-(imidazol-2-ylamino)ethyl]isoxazolin-3-ylcarbonylamino]-2-(4-biphenylsulfonyl-amino) propionic acid,
3-[5-[2-(imidazol-2-ylamino)ethyl]isoxazolin-3-ylcarbonylamino]-2-(1-naphthylsulfonyl-amino) propionic acid, 3-[5-[3-(imidazol-2-ylaminocarbonyl)propyl]isoxazolin-3-ylcarbonylamino]-2-(2,4,6-trimethylphenylsulfonylamino)propionic acid, 3-[5-[3-(benzimidazol-2-ylaminocarbonyl)propyl]isoxazolin-3-ylcarbonylamino]-2-(2,4,6-trimethylphenylsulfonylamino)propionic acid, 3-[5-[4-(benzimidazol-2-ylamino)butyl]isoxazolin-3-ylcarbonylamino]-2-(phenylsulfonylamino)propionic acid, 3-[5-[4-(benzimidazol-2-ylamino)butyl]isoxazolin-3-ylcarbonylamino]-2-(2,6-dichlorophenylsulfonylamino)propionic acid, 3-[5-[4-(benzimidazol-2-ylamino)butyl]isoxazolin-3-ylcarbonylamino]-2-(2,4,6-trimethylphenylsulfonylamino)propionic acid, 3-[5-[4-(benzimidazol-2-ylamino)butyl]isoxazolin-3-ylcarbonylamino]-2-(4-biphenylsulfonylamino)propionic acid, 3-[5-[4-(benzimidazol-2-ylamino)butyl]isoxazolin-3-ylcarbonylamino]-2-(1-naphthylsulfonylamino)propionic acid, 3-[5-[4-(4-methylimidazol-2-ylamino)butyl]-isoxazolin-3-ylcarbonylamino]-2-(phenylsulfonylamino)propionic acid, 3-[5-[4-(4-methylimidazol-2-ylamino)butyl]-isoxazolin-3-ylcarbonylamino]-2-(2,6-dichlorophenylsulfonylamino)propionic acid, 3-[5-[4-(4-methylimidazol-2-ylamino)butyl]-isoxazolin-3-ylcarbonylamino]-2-(2,4,6-trimethylphenylsulfonylamino)propionic acid, 3-[5-[4-(4-methylimidazol-2-ylamino)butyl]-isoxazolin-3-ylcarbonylamino]-2-(4-biphenylsulfonylamino)propionic acid, 3-[5-[4-(4-methylimidazol-2-ylamino)butyl]-isoxazolin-3-ylcarbonylamino]-2-(1-naphthylsulfonylamino)propionic acid, 3-[5-[4-(4,5-dimethylimidazol-2-ylamino)butyl]-isoxazolin-3-ylcarbonylamino]-2-(phenylsulfonylamino)propionic acid, 3-[5-[4-(4,5-dimethylimidazol-2-ylamino)butyl]-isoxazolin-3-ylcarbonylamino]-2-(2,6-dichlorophenylsulfonylamino)propionic acid, 3-[5-[4-(4,5-dimethylimidazol-2-ylamino)butyl]-isoxazolin-3-ylcarbonylamino]-2-(2,4,6-trimethylphenylsulfonylamino)propionic acid, 3-[5-[4-(4,5-dimethylimidazol-2-ylamino)butyl]-isoxazolin-3-ylcarbonylamino]-2-(4-biphenylsulfonylamino)propionic acid, 3-[5-[4-(4,5-dimethylimidazol-2-ylamino)butyl]-isoxazolin-3-ylcarbonylamino]-2-(1-naphthylsulfonylamino)propionic acid, 3-[5-[4-(4,5,6,7-tetrahydrobenzimidazol-2-ylamino)butyl]-isoxazolin-3-ylcarbonylamino]-2-(phenylsulfonylamino)propionic acid, 3-[5-[4-(4,5,6,7-tetrahydrobenzimidazol-2-ylamino)butyl]-isoxazolin-3-ylcarbonylamino]-2-(2,6-dichlorophenylsulfonylamino)propionic acid, 3-[5-[4-(4,5,6,7-tetrahydrobenzimidazol-2-ylamino)butyl]-isoxazolin-3-yl-carbonylamino]-2-(2,4,6-trimethylphenyl-sulfonylamino)propionic acid, 3-[5-[4-(4,5,6,7-tetrahydrobenzimidazol-2-ylamino)butyl]isoxazolin-3-ylcarbonylamino]-2-(4-biphenylsulfonylamino)propionic acid, 3-[5-[4-(-,5,6,7-tetrahydrobenzimidazol-2-ylamino)butyl]-isoxazolin-3-ylcarbonylamino]-2-(1-naphthylsulfonylamino)propionic acid, 3-[5-[3-(7-azabenzimidazol-2-yl)propyl]isoxazolin-3-ylcarbonylamino]-2-(2,4,6-trimethylphenylsulfonylamino)propionic acid, 3-[5-[4-(imidazol-2-ylamino)butyl]isoxazolin-3-ylcarbonylamino]-2-[(2,6-dimethyl-4-phenyl)phenylsulfonylamino]propionic acid, 3-[5-[4-(4-methylimidazol-2-ylamino)butyl]isoxazolin-3-ylcarbonylamino]-2-[(2,6-dimethyl-4-phenyl)phenylsulfonylamino]propionic acid, 3-[5-[4-(4,5-dimethylimidazol-2-ylamino)butyl]isoxazolin-3-ylcarbonylamino]-2-[(2,6-dimethyl-4-phenyl)phenylsulfonylamino]propionic acid, 3-[5-[4-(4,5,6,7-tetrahydrobenzimidazol-2-ylamino)butyl]isoxazolin-3-ylcarbonylamino]-2-[(2,6-dimethyl-4-phenyl)phenylsulfonylamino]propionic acid, 3-[5-[4-(imidazol-2-ylamino)butyl]isoxazolin-3-ylcarbonylamino]-2-[(2,6-dichloro-4-phenyl)phenylsulfonylamino]propionic acid, 3-[5-[4-(4-methylimidazol-2-ylamino)butyl]isoxazolin-3-ylcarbonylamino]-2-[(2,6-dichloro-4-phenyl)phenylsulfonylamino]propionic acid, 3-[5-[4-(4,5-dimethylimidazol-2-ylamino)butyl]isoxazolin-3-ylcarbonylamino]-2-[(2,6-dichloro-4-phenyl)phenylsulfonylamino]propionic acid, 3-[5-[4-(4,5,6,7-tetrahydrobenzimidazol-2-ylamino)butyl]isoxazolin-3-ylcarbonylamino]-2-[(2,6-dichloro-4-phenyl)phenylsulfonylamino]propionic acid, 3-[5-[4-(imidazol-2-ylamino)butyl]isoxazolin-3-ylcarbonylamino]-3-(phenylsulfonylmethyl)propionic acid, 3-[5-[4-(imidazol-2-ylamino)butyl]isoxazolin-3-ylcarbonylamino]-3-(1-adamantylmethyl-aminocarbonyl)propionic acid, 3-[5-[4-(imidazol-2-ylamino)butyl]isoxazolin-3-ylcarbonylamino]-3-(3-pyridinyl)propionic acid, 3-[3-[3-(imidazolin-2-ylamino)propyloxy]isoxazol-5-ylcarbonylamino]-2-(benzyloxycarbonylamino)-propionic acid, 3-[3-[3-(imidazolin-2-ylamino)propyloxy]isoxazol-5-ylcarbonylamino]-2-(n-butyloxycarbonyl-amino)propionic acid, 3-[3-[3-(imidazolin-2-ylamino)propyloxy]isoxazol-5-ylcarbonylamino]-2-(phenylsulfonylamino)propionic acid, 3-[3-[3-(imidazolin-2-ylamino)propyloxy]isoxazol-5-ylcarbonylamino]-2-(n-butylsulfonylamino)-propionic acid, 3-[3-[3-(tetrahydropyrimid-2-ylamino)propyloxy]-isoxazol-5-ylcarbonylamino]-2-(benzyloxycarbonylamino)propionic acid, 3-[3-[3-(tetrahydropyrimid-2-ylamino)propyloxy]-isoxazol-5-ylcarbonylamino]-2-(n-butyloxycarbonylamino)propionic acid, 3-[3-[3-(tetrahydropyrimid-2-ylamino)propyloxy]-isoxazol-5-ylcarbonylamino]-2-(phenylsulfonylamino)propionic acid, 3-[3-[3-(tetrahydropyrimid-2-ylamino)propyloxy]-isoxazol-5-ylcarbonylamino]-2-(n-butylsulfonyl)aminopropionic acid, 3-[3-[2-(imidazolin-2-ylamino)ethyloxy]isoxazol-5-ylcarbonylamino]-2-(benzyloxycarbonylamino)-propionic acid, 3-[3-[3-(imidazolin-2-ylamino)ethyloxy]isoxazol-5-ylcarbonylamino]-2-(n-butyloxycarbonyl-amino)propionic acid, 3-[3-[3-(imidazolin-2-ylamino)ethyloxy]isoxazol-5-ylcarbonylamino]-2-(phenylsulfonylamino)propionic acid, 3-[3-[3-(imidazolin-2-ylamino)ethyloxy]isoxazol-5-ylcarbonylamino]-2-(n-butylsulfonylamino)propionic acid, 3-[3-[3-(tetrahydropyrimid-2-ylamino)ethyloxy]-isoxazol-5-ylcarbonylamino]-2-(benzyloxycarbonylamino) propionic acid, 3-[3-[3-(tetrahydropyrimid-2-ylamino)ethyloxy]-isoxazol-5-ylcarbonylamino]-2-(n-butyloxycarbonylamino) propionic acid, 3-[3-[3-(tetrahydropyrimid-2-ylamino)ethyloxy]-isoxazol-5-ylcarbonylamino]-2-(phenylsulfonylamino)propionic acid, 3-[3-[3-(tetrahydropyrimid-2-ylamino)ethyloxy]-isoxazol-5-ylcarbonylamino]-2-(n-butylsulfonylamino)propionic acid, 3-[3-[3-(imidazol-2-ylamino)propyloxy]-isoxazol-5-ylcarbonylamino]-2-(phenylsulfonylamino)propionic acid, 3-[3-[3-(benzimidazol-2-ylamino)propyloxy]-isoxazol-5-ylcarbonylamino]-2-(phenylsulfonylamino)propionic acid, 3-[3-[3-(4-methylimidazol-2-ylamino)propyloxy]-isoxazol-5-ylcarbonylamino]-2-(phenylsulfonylamino)propionic acid, 3-[3-[3-(4,5-dimethylimidazol-2-ylamino)propyloxy]-isoxazol-5-ylcarbonylamino]-2-(phenylsulfonylamino) propionic acid, 3-[3-[3-(4,5,6,7-tetrahydrobenzimidazol-2-ylamino) propyloxy]-isoxazol-5-ylcarbonylamino]-2-(phenylsulfonylamino)propionic acid, 3-[3-[3-(pyridin-2-ylamino)propyloxy]-isoxazol-5-ylcarbonylamino]-2-(phenylsulfonylamino)propionic acid, and 3-[3-[3-(imidazol-2-ylaminocarbonyl)ethoxy]-isoxazol-5-ylcarbonylamino]-2-(phenylsulfonylamino)propionic acid.

In the present invention it has been discovered that the compounds of Formula Ia, Ib, Ic, Id or Ie above are useful as inhibitors of cell-matrix and cell-cell adhesion processes. The present invention includes novel compounds of Formula Ia, Ib, Ic, Id or Ie and methods for using such compounds for the prevention or treatment of diseases resulting from abnormal cell adhesion to the extracellular matrix which comprises administering to a host in need of such treatment a therapeutically effective amount of such compound of Formula Ia, Ib, Ic, Id or Ie.

In the present invention it has also been discovered that the compounds of Formula Ia, Ib, Ic, Id or Ie above are useful as inhibitors of $\alpha_v\beta_3$. The compounds of the present invention inhibit the binding of vitronectin to $\alpha_v\beta_3$ and inhibit cell adhesion.

The present invention also provides pharmaceutical compositions comprising a compound of Formula Ia, Ib, Ic, Id or Ie and a pharmaceutically acceptable carrier.

The present invention provides improved methods for the delivery of integrin antagonists, especially by transdermal iontophoresis. The methods and compositions of the invention are not limited to the delivery of integrin antagonists by any one particular iontophoretic device. Generally, the iontophoretic drug delivery device used in the present invention comprises a power source for generation of an electrical current and two electrode compartments that when adhering to the skin of a subject will pass a generated electrical current through the skin. In the presence of the electrical current the passage through the skin of the integrin antagonist, which is contained in one of the electrode compartments, is enhanced. As is appreciated by one of skill in the art of iontophoresis drug delivery, the rate of transdermal delivery of the integrin antagonist in accordance with the present invention can be controlled by selection of the patch design, including the selection of the contents of the electrode compartments, the surface area of the patch, and by the strength of the generated electrical current.

Iontophoretic devices useful in the present invention are described, for example, in the following U.S. Patents, the disclosures of which are incorporated herein by reference: U.S. Pat. Nos. 3,991,755; 4,141,359; 4,250,878; 4,395,545; 4,744,787; 4,747,819; 4,927,408; 5,080,646; 5,084,006; 5,125,894; 5,135,477; 5,135,480; 5,147,296; 5,147,297; 5,158,537; 5,162,042; 5,162,043; 5,167,616; 5,169,382; 5,169,383; 5,415,628; 5,203,768; 5,207,752; 5,221,254; 5,232,438; 5,234,992; 5,240,995; 5,246,417; 5,288,389; 5,298,017; 5,310,404; 5,312,326; 5,314,502; 5,320,598; 5,322,502; 5,326,341; 5,344,394; 5,374,242; 5,380,271; 5,385,543; 5,387,189; 5,395,310; 5,403,275; 5,405,317; 5,415,628; 5,423,739; 5,443,442; 5,445,606; 5,445,609; 5,464,387; 5,466,217; 4,950,229; 5,246,418; 5,256,137; 5,284,471; 5,302,172; 5,306,235; 5,310,403; 5,320,597; 5,458,569; 5,498,235; 4,557,723; 4,713,050; 4,865,582; 4,752,285; 5,087,242; 5,236,412; 5,281,287.

In general, at least two electrodes are used in the iontophoretic device. Both of these electrodes are disposed so as to be in intimate electrical contact with some portion of the skin of the body. One electrode, called the active or donor electrode, is the electrode from which the ionic integrin inhibitor drug precursor or drug is delivered into the body by iontophoresis. The other electrode, called the counter or return or indifferent electrode, serves to close the electrical circuit through the body. In conjunction with the patient's skin contacted by the electrodes, the circuit is completed by connection of the electrodes to a source of electrical energy, for example, a battery. If the integrin inhibitor to be delivered into the body is positively charged (i.e., a cation), then the anode will be the active electrode and the cathode will serve to complete the circuit. If the integrin inhibitor to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

The iontophoresis device includes a drug or agent reservoir or source of the integrin inhibitor drug (which is preferably an ionized or ionizable form of the drug or a precursor of such drug) to be iontophoretically delivered or introduced into the body. Such drug reservoir is electrically connected to the anode or the cathode of the iontophoresis device to provide a fixed or renewable source of one or more desired integrin inhibitors.

A variety of iontophoresis patch designs may be suitably used in the present invention. For example, iontophoretic delivery devices have been developed in which the donor and counter electrode assemblies have a "multi-laminate" construction. In these devices, the donor and counter electrode assemblies are each formed by multiple layers of usually polymeric matrices. For example, U.S. Pat. No. 4,731,049 discloses a donor electrode assembly having a hydrophilic polymer based electrolyte reservoir and drug reservoir layers, a skin-contacting hydrogel layer, and optionally one or more semipermeable membrane layers. U.S. Pat. No. 4,474,570 discloses an iontophoresis device wherein the electrode assemblies include a conductive resin film electrode layer, a hydrophilic gel reservoir layer, and aluminum foil conductor layer and an insulating backing layer.

The drug and electrolyte reservoir layers of the iontophoretic delivery device may be, for example, formed of hydrophilic polymers, as described, for example, in U.S. Pat. Nos. 4,474,570, 4,383,529, 4,764,164. Hydrophilic polymers may be desired since water is the preferred solvent for ionizing many drug salts, and hydrophilic polymer components of the drug reservoir in the donor electrode and the electrolyte reservoir in the counter electrode can be hydrated in situ while attached to the body by absorbing water from the skin through transepidermal water loss or sweat or from a mucosal membrane by absorbing saliva in the case of oral mucosal membranes. Once hydrated, the device begins to deliver ionized agent to the body. This enables the drug reservoir to be manufactured in a dry state, giving the device a longer shelf life. Hydrogels have been particularly favored for use as the drug reservoir matrix and electrolyte reservoir matrix in iontophoretic delivery devices, in part due to their high equilibrium water content and their ability to quickly absorb water. In addition, hydrogels tend to have good biocompatibility with the skin and with mucosal membranes.

In the present invention it has been discovered that prodrugs of integrin inhibitors, in particular inhibitors of $\alpha_v\beta_3$ integrins, are preferably delivered using an electrically powered iontophoretic delivery device. The present invention includes methods for the treatment of diseases mediated by such integrin, such as cancer metastasis, diabetic retinopathy, neovascular glaucoma, thrombosis, restenosis, osteoporosis, or macular degeneration which comprises administering to a host in need of such treatment a therapeutically effective amount of an integrin inhibitor prodrug by iontophoresis.

The present invention also provides pharmaceutical compositions suitable for iontophoretic delivery comprising an integrin inhibitor prodrug and a pharmaceutically acceptable carrier.

The compounds of Formula Ia, Ib, Ic, Id or Ie of the present invention are useful for the treatment (including prevention) of angiogenic disorders, comprising administering to a mammal in need of such treatment a therapeutically effective amount of a compound of Formula Ia, Ib, Ic, Id or Ie described above. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion.

The compounds of Formula Ia, Ib, Ic, Id or Ie of the present invention are also useful for the treatment (including prevention) of thromboembolic disorders, comprising administering to a mammal in need of such treatment a therapeutically effective amount of a compound of Formula Ia, Ib, Ic, Id or Ie described above. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolisms, kidney embolisms, pulmonary embolisms, or such disorders associated with diabetes.

The compounds of Formula Ia, Ib, Ic, Id or Ie of the present invention may also be useful for the treatment or prevention of other diseases which involve cell adhesion processes, including, but not limited to, inflammation, bone degradation, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds of Formula Ia, Ib, Ic, Id or Ie of the present invention may also be useful for wound healing.

The compounds of the present invention may be used for other ex vivo applications to prevent cellular adhesion in biological samples.

The compounds of the present invention can also be administered in combination with one or more additional therapeutic agents selected from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula Ia, Ib, Ic, Id or Ie of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic or other disorders.

By "therapeutically effective amount" is meant an amount of a compound of Formula Ia, Ib, Ic, Id or Ie that when administered alone or in combination with an additional therapeutic agent to a cell or mammal is effective to prevent or ameliorate the disease condition or the progression of the disease.

By "administered in combination" or "combination therapy" it is meant that the compound of Formula Ia, Ib, Ic, Id or Ie and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin sodium crystalline clathrate and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Other suitable anti-platelet agents include ticlopidine, including pharmaceutically acceptable salts or prodrugs thereof. Ticlopidine is also a preferred compound since it is known to be gentle on the gastrointestinal tract in use. Still other suitable platelet inhibitory agents include thromboxane-$A_2$-receptor antagonists and thromboxane-$A_2$-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication No. 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase, retivase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. The term urokinase, as used herein, is intended to denote both dual and single chain urokinase, the latter also being referred to herein as prourokinase.

The compounds of the present invention are also useful as standard or reference compounds, for example as a quality standard or control, in tests or assays involving the binding of vitronectin or fibrinogen to $\alpha_v\beta_3$. Such compounds may be provided in a commercial kit, for example, for use in pharmaceutical research involving $\alpha_v\beta_3$. The compounds of the present invention may also be used in diagnostic assays involving $\alpha_v\beta_3$.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0–3 $R^4$, then said group may optionally be substituted with up to three $R^4$ and $R^4$ at each occurrence is selected independently from the defined list of possible $R^4$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula Ia, Ib, Ic, Id or Ie, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula Ia, Ib, Ic, Id or Ie via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_0$–$C_{10}$ alkyl" denotes alkyl having 0 to 10 carbon atoms; $C_0$ denotes a direct bond between the groups linked by the $C_0$ group; also by way of example, "$C_1$ to $C_4$" denotes methyl, ethyl, n-propyl, isopropyl, n-butyl, 2-methylpropyl, 1-methylpropyl, 1,1-dimethyl ethyl); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. The term "cycloalkylalkyl" represents a cycloalkyl group attached through an alkyl bridge; for example cyclopropylmethyl, cyclopropylethyl, cyclobutylmethyl, cyclopentylmethyl, cyclohexylmethyl, and so forth.

"Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula Ia, Ib, Ic, Id or Ie. Such "alkylene", "alkenylene", "phenylene", and the like, may alternatively and equivalently be denoted herein as "-(alkyl)-", "-(alkyenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocyclic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

As used herein, "pharmaceutically acceptable salts" refer to derivatives of the disclosed compounds wherein the parent compound of Formula Ia, Ib, Ic, Id or Ie is modified by making acid or base salts of the compound of Formula Ia, Ib, Ic, Id or Ie. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula Ia, Ib, Ic, Id or Ie in vivo when such prodrug is administered to a mammalian subject. Prodrugs of the compounds of Formula Ia, Ib, Ic, Id or Ie are prepared by modifying functional groups present in the compounds in such a way that the modifications are cleaved, either in routine manipulation or in vivo, to the parent compounds. Prodrugs include compounds of Formula Ia, Ib, Ic, Id or Ie wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula Ia, Ib, Ic, Id or Ie, and the like. Examples of representative carboxyl and amino prodrugs are included under the definition of $R^2$, $R^3$, and Y.

As used herein, the term "pharmaceutically acceptable anion" is intended to include anions formed, for example, from non-toxic inorganic or organic acids. For example, such conventional non-toxic salts include, but are not limited to, halide, bisulfate, sulfate, hydrogenphosphate, phosphate, toluenesulfonate, methanesulfonate, ethanesulfonate, acetate, trifluoroacetate, citrate, oxalate, succinate, malonate and so forth.

The pharmaceutically acceptable salts of the compounds of Formula Ia, Ib, Ic, Id or Ie include the conventional non-toxic salts or the quaternary ammonium salts of the compounds of Formula Ia, Ib, Ic, Id or Ie formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanesulfonic, ethanedisulfonic, oxalic, isethionic, and the like.

The pharmaceutically acceptable salts of the present invention can be synthesized from the compounds of Formula Ia, Ib, Ic, Id or Ie which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula Ia, Ib, Ic, Id or Ie may be prepared by reacting the acid with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, methanol, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Iontophoretic Devices

An iontophoretic device useful in the present invention may, by way of example and not limitation, include the following component and materials. Additionally, iontophoretic devices useful in the present invention are disclosed in U.S. patent application U.S. Ser. No. 08/877829 filed Jun. 18, 1997; the disclosure of which is hereby incorporated herein by reference in its entirety.

A. Current Distributing Member/Active Electrode

The iontophoretic electrode of the invention includes a current distributing member which conveys electrical current into the iontophoretic reservoirs for the delivery of an ionized substance. The current distributing member is constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes without being eroded or depleted due to the distribution of current, and conducts current through the generating hydronium or hydroxyl ions by, respectively, either reduction or oxidation of water. Inert conductive materials typically include, for example, stainless steel, platinum, gold, and carbon or graphite.

Alternatively, the current distributing member may be constructed from a sacrificial conductive material. A material may be considered sacrificial if, when employed as an electrode in an iontophoretic device of the invention, material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate eletrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context. Nonetheless, the term sacrificial encompasses such materials and is intended to include materials that undergo physical and/or chemical changes during iontophoresis.

The current distributing member may take any form known in the art, such as the form of a plate, foil layer, screen, wire, or dispersion of conductive particles embedded in a conductive matrix.

B. The Electrolyte Reservoir

In the iontophoretic devices of the invention, an electrolyte reservoir is arranged in electrical communication with a current distributing member. Typically, electrical communication requires that electrons from the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface is preferably low.

The electrolyte reservoir comprises at least one electrolyte, i.e., an ionic or ionizable component which can act to conduct current toward or away from the current distributing member. Typically, the electrolyte comprises one or more mobile ions, the selection of which is dependent upon the desired application. Examples of suitable electrolytes include aqueous solutions of salts. A preferred electrolyte is an aqueous solution of NaCl, having a concentration of less than 1 mole/liter (<1 mM), more preferably at about physiological concentration. Other electrolytes include salts of physiological ions including, but not limited to, potassium, chloride, and phosphate. The salt and its concentration may be selected as desired for particular applications.

Other chemical species may be selected by the skilled artisan for inclusion in the electrolyte reservoir. Such other reservoir species include, without limitation, chelation agents (e.g., citrate ions, EDTA) surfactants (e.g., non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulosic resins, clays), and the like.

Alternatively, the electrolyte may comprise a material which is itself relatively immobile in the absence of an electric field, but which acts to deliver mobile ions in the presence of an electric field. In the latter case, the electrolyte may more properly be termed an "ion source." Examples of ion sources according to the invention include polyelectrolytes, ion exchange membranes and resins, non-ionic buffers which become ionic upon pH change, and other known ion sources.

Alternatively, the electrolyte reservoir may contain counterions that form a soluble salt with an electrochemically generated ion. For example, in an apparatus employing a silver anodal current distributing member, a suitable counterion might be acetate or nitrate. Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

C. Agent Reservoir

The reservoir structure of the iontophoretic apparatus of the invention further includes an agent reservoir. The agent reservoir must be capable of ionic communication with an epithelial surface and is in electrical communication with the anode or cathode of the iontophoresis device.

The construction of the ionized substance reservoir must be consistent with the requirements for ionic communication with the epithelial surface and electrical communication with current distribution member. Accordingly, the structure of the ionized substance reservoir would vary, depending upon the desired application. The ionized substance reservoir may include a liquid, semi-liquid, semi-solid, or solid material. With a flowable material, the ionized substance reservoir preferably further comprises means for at least substantially inhibiting the flow of the contents out of the reservoir preferably further comprises means for at least substantially inhibiting the flow of the contents out of the reservoir. In such situations, the flow of the contents is desirably minimized when the device is in storage. For example, a membrane may be deployed to surround the contents of the ionized substance reservoir. In certain situations the flow of the contents of the reservoir may be minimized while in storage, but increased in use. For example, a surrounding membrane may increase in porosity, permeability, or conductivity upon the application of an electric field across the membrane. Examples of such membranes are disclosed in U.S. Pat. Nos. 5,080,546; 5,169,382; and 5,232,438, the disclosures of which are incorporated by reference herein.

In preferred embodiments, the ionized substance reservoir is constructed to retain its physical integrity and to inherently resist migration and loss of the ionized substance. Such embodiments include those in which the ionized substance reservoir includes a solid or semi-solid material such as a gel or other polymeric material. In an especially preferred embodiment, the ionized substance reservoir includes a polymeric film in which the substance to be iontophoretically delivered is dispersed. The mobility of the substance to be delivered is substantially increased by the application of the electric field, permitting effective delivery across the target epithelial surface. Such a film need not contain any significant amount of hydrating material. In preferred embodiments, a cross-linked hydrogel in the electrolyte reservoir, because it inherently contains significant amounts of water, can server as a water reservoir during iontophoresis.

It may be desirable to provide the solution of active ingredient with a buffer. The ion of the buffer of like charge to the drug ion should have low ionic mobility. The limiting ionic mobility of this ion is preferably no greater than $1 \times 10^{-4}$ cm$^2$/volt-sec.

Additionally, it may be desirable to control the flux profile of the drug being delivered by iontophoresis by adding to or having present in the reservoir containing the drug, ions which would compete with the drug ions for current (competing ions). To achieve various flux profiles for the drug being iontophoretically delivered, one may apply constant current but vary the concentration of the competing ions.

D. Ionizable Substance (Drug) for Iontophoretic Delivery

The ionizable drug can be delivered from either the anode, the cathode, or both simultaneously. For example, if the compound to be driven into the body is positively charged, then the positive electrode (anode) will be the active electrode and the negative electrode (cathode) will serve to complete the electrochemical circuit. Alternatively, if the ionic substance to be delivered is negatively charged, then the negative electrode (cathode) will be the active electrode and the positive electrode (anode) will be the indifferent electrode.

It is believed that this invention has utility in connection with the delivery of active ingredients within the broad class of cell adhesion molecules as well as chemical modifications of cell adhesion molecules.

E. Protective Backing

The iontophoretic apparatus of the invention may also include a suitable backing film positioned on top of the electrolyte reservoir. The backing film provides protection against contamination and damage to the current distributing member, if present, and the electrolyte reservoir of the apparatus.

F. Release Liner

The iontophoretic apparatus of the invention optionally includes a release liner which may be fixed to the underside of the ionized substance reservoir by an adhesive. The release liner protects the surface of the ionized substance reservoir which contact the epithelial surface from contamination and damage when the device is not in use. When the device is ready for use, the release liner may be peeled off to expose the epithelial contacting surface of the ionized substance reservoir for application of the device to a patient.

G. Indifferent Electrode

Iontophoretic devices require at least two electrodes to provide a potential to drive drug ions into the skin of a patient. Both electrodes are disposed to be in intimate electrical contact with the skin thereby completing the electrochemical circuit formed by the anode pad and cathode pad of the iontophoretic device. The electrode pads may be further defined as an active electrode from which an ionic drug is delivered into the body. An indifferent or ground electrode serves to complete the electrochemical circuit.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. The compounds of Formula Ia, Ib, and Ic can be synthesized by methods disclosed in U.S. patent application U.S. Ser. No. 08/770538 filed Dec. 20, 1996 or published in WO 97/23480 on Jul. 3, 1997. The compounds of Formula Id can be synthesized by methods disclosed in U.S. patent application U.S. Ser. No. 08/816580 filed Mar. 13, 1997 or published in WO 97/33887 on Sep. 18, 1997. The compounds of Formula Ie can be synthesized by methods disclosed in U.S. patent application U.S. Ser. No. 08/647132 filed May 9, 1996 or published in WO 96/37492 on Nov. 28, 1996. Preferred methods include, but are not limited to, those described below. All references cited herein are hereby incorporated by reference in their entirety.

In general, prodrug esters to the $\alpha_v\beta_3$ antagonists can be prepared (Scheme A1) by coupling the ammonium ester of diaminopropionic acid to the acid portion of the indazole, spiroisoxazoline or isoxazoline cores in the presence of coupling reagents such as dicyclohexylcarbodiimide, BOP regent etc. well know to one skilled in the art of organic synthesis.

Scheme A1

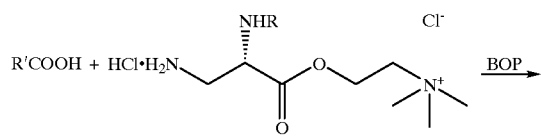

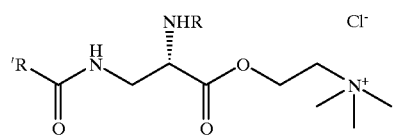

-continued

The synthesis of choline ester prodrug of $\alpha_v\beta_3$ antagonists in the indazole series is exemplified by the following example shown in Scheme A2. The diaminopropionic acid derivative 1 was purchased from Bachem and treated with 2,4,6-trimethylbenzenesulfonylchloride in the presence of diisopropylethylamine to provide intermediate 2 which was saponified with lithium hydroxide. The intermediate 3 was then coupled with N,N-dimethylaminoethanolamine in the presence of coupling reagent BOP (benzotriazole-1-yloxytris(dimethylamnio)phosphonium hexafluorophosphate) to provide intermediate 4 which on treatment with methyl iodide provided the trimethylammonium derivative 5. The intermediate 5 on deprotection with hydrogen chloride in dioxane provided intermediate 6. The coupling of intermediate 6 with the indazole derivative 7 provided the final prodrug product of Example 1. The indazole derivative 7 was synthesized as reported previously (Jadhav, P. K.; et al. WO 97/23480 published Jul. 3, 1997).

Scheme A2

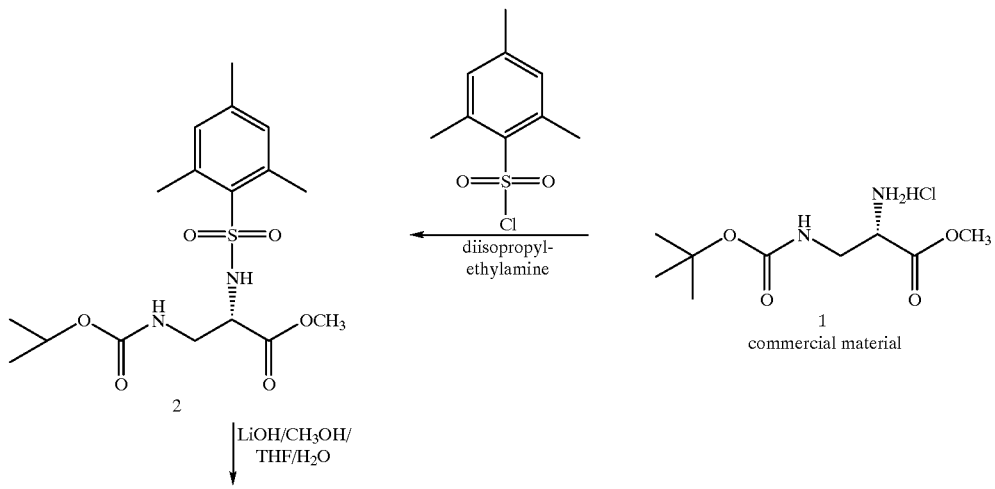

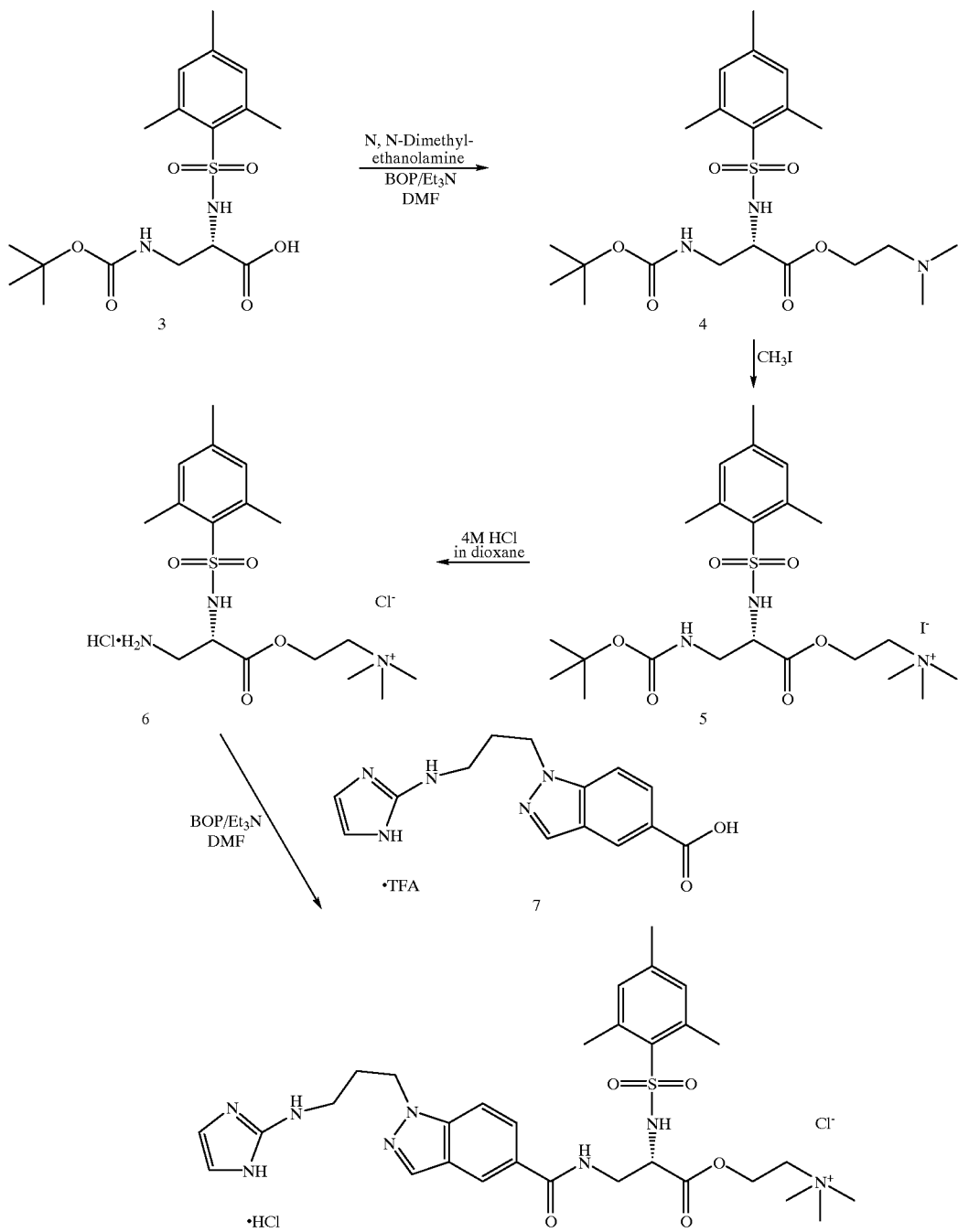

Similarly, a 4-(2-hydroxyethyl)morpholine derived prodrug was synthesized as shown in Scheme A3. The intermediate 3 as obtained earlier (Scheme A2) was coupled with 4-(2-hydroxyethyl)morpholine in the presence of BOP reagent to provide intermediate 8 which on treatment with methyl iodide provided quartarnary ammonium derivative 9.

The intermediate 9 was deprotected with hydrogen chloride in dioxane to provide 10 which was coupled to the indazole derivative 7 to provide ammonium prodrug ester of Example 2.

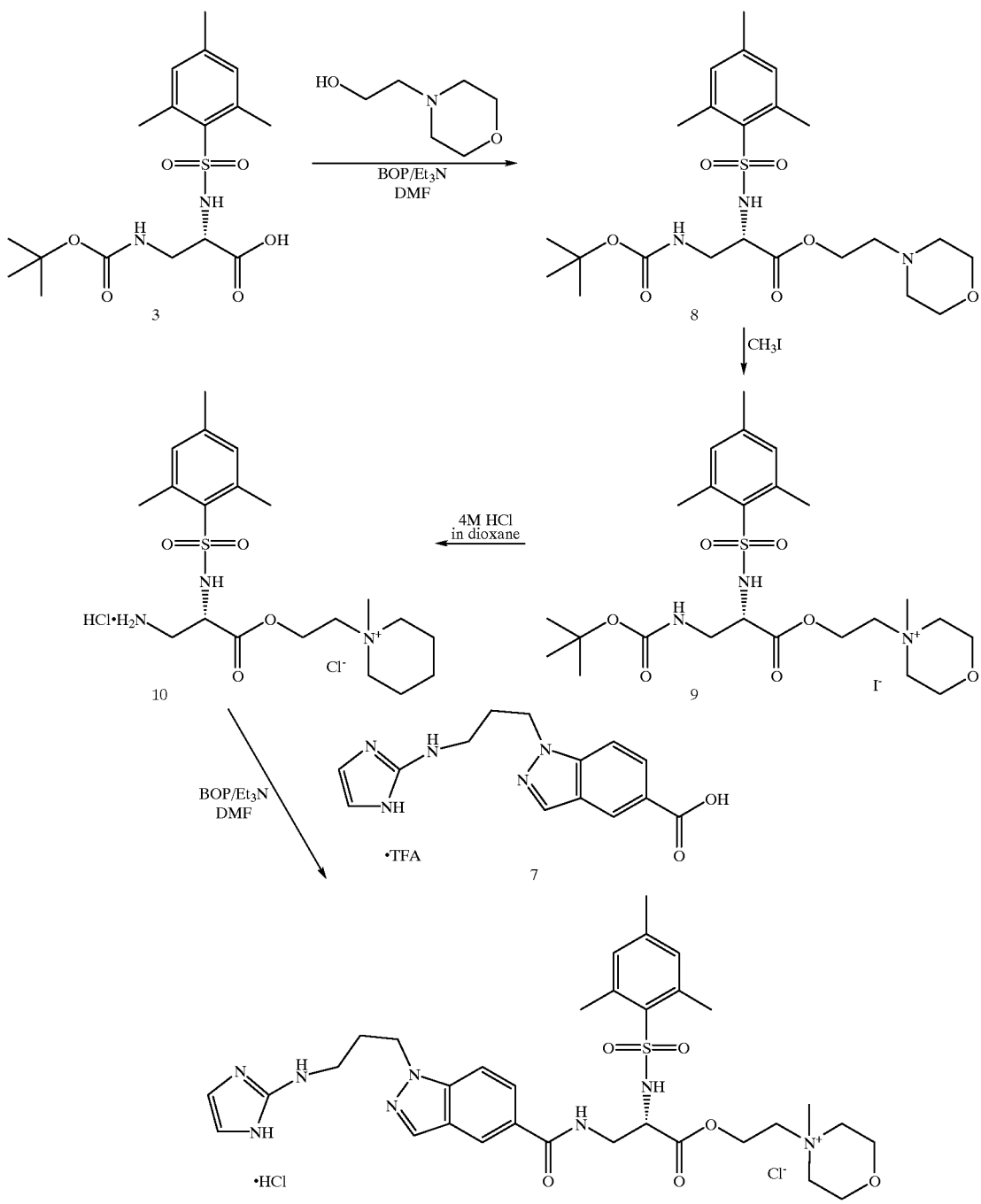

Scheme A3

EXAMPLE 1

Trimethylammoniumethyl 3-[1-[3-imidazol-2-ylamino)propyl]-indazol-5-ylcarbonyl-amino-2(S)-(2,4,6-trimethylbenzenesulfonylamino)-propionate bishydrochloride A Methyl 3-(tert-butyloxycarbonylamino)-2-(S)-(2,4,6-trimethylbenzenesulfonylamino)-propionate H-DAP(Boc) OMe.HCl (Bachem) 7.64 g (30 mmol) and diisopropylethylamine 7.76 g (60 mmol) were dissolved in 100 ml dichloromethane and treated dropwise with (2,4,6-trimethyl)benzenesulfonyl chloride 6.56 g (30 mmol) in 25 ml dichloromethane. The mixture was stirred at room temperature for 18 hours. TLC in 1:3 EtOAc:Hexane indicated product Rf=0.3. The mixture was diluted with dichloromethane and washed with water. The organic layer was separated, dried (MgSO$_4$), filtered, concentrated and the residue purified by flash chromatography; 325 g silica gel column using 1:3 EtOAc:Hexane followed by 1:2 to elute 10.96 g of 2 as a white solid (91.2% yield). $^1$H NMR (300 MHz, CDCl$_3$): 1.42 (s, 9H); 2.29 (s, 3H); 2.63 (s, 6H); 3.46

(m, 2H); 3.57 (s, 3H); 3.86–3.92 (m, 1H); 4.89 (m, 1H); 5.68 (bd, 1H); 6.94 (s, 2H).

B Methyl 3-(tert-butyloxycarbonylamino)-2-(S)-(2, 4,6-trimethylbenzenesulfonylamino)-propionic acid The intermediate obtained from example 1 part A, 10.9 g (27.2 mmol) was dissolved in 99 ml of 1:1:1 MeOH:THF:$H_2O$ and treated with lithium hydroxide 5.04 g (120 mmol) and stirred at room temperature for 18 hours. TLC indicated disappearance of the starting material. The mixture was neutralised with 1N HCl (120 mmol) and extracted with ethyl acetate (2×100 ml). The organic extracts were combined, dried ($MgSO_4$), filtered, concentrated to afford 10.5 g of 2 as a white solid (quant. yield). $^1$H NMR (300 MHz, DMSO-$d_6$): 1.29 (s, 9H); 2.20 (s, 3H); 2.51 (s, 6H); 3.02–3.15 (m, 2H); 3.71–3.73 (m, 1H); 6.72 (t, 1H, J=5.5 Hz); 6.95 (s, 2H); 7.81 (d, J=8.8 Hz); 12.5 (bs, 1H).

C Dimethylaminoethyl 3-(tert-butyloxycarbonylamino)-2-(S)-(2,4,6-trimethylbenzenesulfonylamino)-proionate N,N-Dimethylaminoethanol 5.8 g (65 mmol), triethylamine 11.13 g (110 mmol), and the product of example 1 part B, 20 g (52 mmol) were dissolved in 80 ml dimethylformamide and treated with benzotriazol-1-yloxytris (dimethylamino)phosphonium hexafluorophosphate 28.7 g (65 mmol). The mixture was stirred at room temperature for 18 hours. TLC in 1:8 MeOH:$CHCl_3$ indicated product Rf=0.5. The mixture was diluted with EtOAc and washed with $H_2O$, $NaHCO_3$ (2×50 ml), brine, and water. The organic layer was separated, dried ($MgSO_4$), filtered and concentrated to afford 25 g of 3 as an oil. $^1$H NMR (300 MHz, $CDCl_3$): 1.41 (s, 9H); 2.28 (s, 3H); 2.34 (s, 6H); 2.64 (s, 6H), 3.41–3.57 (m, 2H); 3.97 (m, 1H); 4.07–4.11 (m, 1H); 4.33–4.40 (m, 1H); 6.93 (s, 2H). HRMS calcd for $C_{21}H_{36}N_3O_6S$ [M+H]$^+$ 458.232482, found 458.233361.

D Trimethylammoniumethyl 3-(tert-butyloxycarbonylamino)-2-(S)-(2,4,6-trimethylbenzenesulfonylamino)-propionate The product of example 1 part C, 5 g (11 mmol) was dissolved in 35 ml acetone and treated with iodomethane 7 g (50 mmol). The mixture was stoppered and protected from light and stirred at room temperature for 18 hours. An off-white precipitate formed was filtered and washed with $Et_2O$ (2×25 ml). The solid was dried to afford 4.6 g of 4 as an off-white solid (74% yield). $^1$H NMR (300 MHz, DMSO-$d_6$): 1.29 (s, 9H); 2.22 (s, 3H); 2.50 (s, 6H); 3.08 (s, 9H); 3.13–3.19 (m, 2H); 3.50–3.55 (m, 2H); 3.75–3.78 (m, 1H); 4.13–4.17 (m, 2H); 6.90 (t, 1H, J=12.2 Hz); 7.00 (s, 2H); 8.17 (d, 1H, J=9.1 Hz). HRMS calcd for $C_{22}H_{38}N_3O_6S$ [M]$^+$ 472.248133, found 472.250689.

E Trimethylammoniumethyl 3-(amino)-2-(S)-(2,4,6-trimethylbenzenesulfonylamino)-propionate chloride iodide The product of example 1 part D, 4.6 g (7.7 mmol) was treated with 20 ml of 4.0M HCl in dioxane. The off-white solid became an orange/brown gummy solid with an almost colorless supernatent. The mixture was stirred at room temperature for 18 hours. An NMR of the gummy solid showed absence of a t-butyl group at 1.29 ppm. The mixture was stripped and pumped under high vacuum. The resulting orange solid was pulverized with a mortar and pestle and pumped further to afford 3.3 g of product as an orange solid (96.3% yield). $^1$H NMR (300 MHz, DMSO-$d_6$): 2.24 (s, 3H); 2.53 (s, 6H); 2.90–3.04 (m, 2H); 3.05 (s, 9H); 3.55–3.62 (m, 2H); 4.18–4.23 (m, 3H); 7.03 (s, 2H); 8.28 (bs, 3H); 8.49 (d, 1H, J=9.6 Hz). HRMS calcd for $C_{17}H_{30}N_3O_4S$ [M]$^+$ 372.195704, found 372.196900.

Trimethylammoniumethyl 3-[1-[3-imidazol-2-ylamino)propyl]-indazol-5-ylcarbonyl-amino-2(S)-(2,4,6-trimethylbenzenesulfonylamino)-propionate bishydrochloride The product of example 1 part E, 445 mg (1 mmol), and the indazole intermediate 399 mg (1 mmol), (as previously prepared see Jadhav, P. K.; Petraitis, J. J.; Batt, D. G. WO 9723480 published Jul. 3, 1997), and 4-methylmorpholine 505 mg (5 mmol) were dissolved in 10 ml dimethylformamide and treated with benzotriazol-1-yloxytris (dimethylamino)phosphonium hexafluorophosphate 663 mg (1.5 mmol). The mixture was stirred at room temperature for 18 hours. The solvent was removed under high vacuum and the residue purified by preparative HPLC. Rainin HPLC Dynamax C18 prep column 41.4×250 mm 100% A to 100% B over 25 minutes A=98% water, 2% Acetonitrile, and 0.05% TFA B=80% Acetonitrile, 20% water, and 0.05% TFA Retention time of TFA salt of 8=15.3 minutes The TFA salt was collected and stripped. The residue which contained an impurity from the benzotriazol-1 yloxytris(dimethylamino) phosphonium hexafluorophosphate was then prepped again to give 280 mg of the bis-HCl salt 8 as a yellow solid (39.3% yield). 100% A to 100% B over 25 minutes A=98% water, 2% Acetonitrile, and 26 mmol of Hcl B=80% Acetonitrile, 20% water, and 26 mmol of Hcl Retention time of 8=13.6 minutes $^1$H NMR (300 MHz, $D_2O$): 1.33 (s, 3H); 2.07–2.11 (m, 2H); 2.26 (s, 6H); 2.94–2.98 (m, 2H); 3.05 (s, 9H); 3.17–3.25 (m, 1H); 3.6–3.69 (m, 3H); 4.24–4.29 (m, 1H); 4.42 (t, 2H, J=6.2 Hz); 4.48–4.50 (m, 2H); 6.33 (s, 2H); 6.37 (s, 2H); 7.32 (s, 2H); 7.72 (s, 1H); 8.07 (s, 1H). HRMS calcd for $C_{31}H_{43}N_8O_5S$ [M]$^+$ 639.307714, found 639.310483. Anal. calcd. for $C_{31}H_{42}N_8O_5SCl.2.2HCl$: C, 49.29; H, 6.03; N, 14.08; S, 4.24; Cl, 15.02; found: C, 49.52; H, 6.02; N, 14.83; S, 3.88, Cl, 15.07.

EXAMPLE 2

Methylmorpholinoammoniumethyl 3-[1-[3-imidazol-2-ylamino)propyl]-indazol-5-ylcarbonyl-amino-2(S)-(2,4,6-trimethylbenzenesulfonylamino)-propionate bishydrochloride A Morpholinoethyl 3-(tert-butyloxycarbonylamino)-2-(S)-(2,4,6-trimethylbenzenesulfonylamino)-propionate 4-(2-Hydroxyethyl)morpholine 1.53 g (11.6 mmol), 4-pyrrolidinopyridine 1.15 g (7.76 mmol), and the product of example 1 part B, 3 g (7.76 mmol) were dissolved in 15 ml dimethylformamide and treated with dicyclohexylcarbodiimide 2.63 g (13 mmol). The mixture was stirred at room temperature for 18 hours. A white precipitate formed progressively with time. TLC in 1:8 MeOH:$CHCl_3$ indicated product Rf=0.7. The mixture was diluted with EtOAc and the solid filtered off. The supernatant liquid was washed with water(2×100 ml). The aqueous layers were back-extracted with EtOAc. The organic extracts were combined and washed with brine. The organic layer was separated, dried ($MgSO_4$), filtered and concentrated to afford 3.08 g of product as a white solid (79.4%). $^1$H NMR (300 MHz, DMSO-$d_6$): 1.29 (s, 9H); 2.21 (s, 3H); 2.25–2.29 (m, 6H); 2.49 (s, 6H), 3.03–3.21 (m, 2H); 3.49 (t, 4H, J=4.4 Hz);

3.73–3.81 (m, 3H); 6.82 (t, 1H, J=5.9 Hz); 6.96 (s, 2H); 8.07–8.1 (m, 1H). HRMS calcd for $C_{23}H_{38}N_3O_7S$ [M+H]$^+$ 500.243048, found 500.243560.

B Methylmorpholinoammoniumethyl 3-(tert-butyloxycarbonylamino)-2-(S)-(2,4,6-trimethylbenzenesulfonylamino)-propionate The product of example 2 part A, 3 g (6.0 mmol) was dissolved in 20 ml acetone and treated with iodomethane 7 g (30 mmol). The mixture was stoppered and protected from light and stirred at room temperature for 18 hours. The mixture was stripped and pumped under high vacuum to afford 3.715 g of product as an off-white solid (96.5% yield). $^1$H NMR (300 MHz, DMSO-d$_6$): 1.29 (s, 9H); 2.22 (s, 3H); 2.50 (s, 6H); 3.08–3.22 (m, 2H); 3.17 (s, 3H); 3.45 (bs, 4H); 3.70–3.8 (m, 3H); 3.89 (m, 4H); 4.18–4.25 (m, 2H); 6.88 (t, 1H, J=5.5 Hz); 7.00 (s, 2H) ; 8.17 (d, 1H, J=9.1 Hz). HRMS calcd for $C_{24}H_{40}N_3O_7S$ [M]$^+$ 514.260035, found 514.258878.

C Methylmorpholinoammoniumethyl 3-(amino)-2-(S)-(2,4,6-trimethylbenzenesulfonylamino)-propionate The product of example 2 part B, 2.56 g (4 mmol) was treated with 40 ml of 1.0M HCl in dioxane. The off-white solid became an orange/brown gummy solid with an almost colorless supernatent. The mixture was stirred at room temperature for 18 hours. An NMR of the gummy solid showed the reaction was not complete. The solid was treated with 15 ml of 4.0M HCl in dioxane and stirred at room temperature for 18 hours. NMR of the gummy solid indicated absence of a t-butyl group at 1.29 ppm. The mixture was stripped and pumped under high vacuum. The resulting orange solid was pulverized with a mortar and pestle and pumped further to afford 2.01 g of product as an orange solid (quantitative yield). $^1$H NMR (300 MHz, DMSO-d$_6$): 2.23 (s, 3H); 2.53 (s, 6H); 2.9–3.1 (m, 2H); 3.16 (s, 3H); 3.44 (bs, 4H); 3.75–3.76 (m, 2H); 3.87–3.89 (m, 4H); 4.19–4.29 (m, 3H); 7.03 (s, 2H); 8.39 (bs, 3H); 8.56 (d, 1H, J=9.9 Hz). HRMS calcd for $C_{19}H_{32}N_3O_5S$ [M]$^+$ 414.206268, found 414.206714.

Methylmorpholinoammoniumethyl 3-[1-[3-imidazol-2-ylamino)propyl]-indazol-5-ylcarbonyl-amino-2(S)-(2,4,6-trimethylbenzenesulfonylamino)-propionate bishydrochloride The product of example 2 part C, 1.23 g (2.5 mmol), and the indazole intermediate (as prepared previously Jadhav, P. K.; Petraitis, J. J.; Batt, D. G. WO 9723480 published Jul. 3, 1997) 1.0 g (2.5 mmol), and 4-methylmorpholine 1.26 g (12.5 mmol) were dissolved in 10 ml dimethylformamide and treated with benzotriazol-1-yloxytris(dimethylamino) phosphonium hexafluorophosphate 1.22 g (2.75 mmol). The mixture was stirred at room temperature for 18 hours. The solvent was removed under high vacuum and the residue purified by preparative HPLC. Rainin HPLC Dynamax C18 prep column 41.4×250 mm 100% A to 100% B over 25 minutes A=98% water, 2% Acetonitrile, and 0.05% TFA B=80% Acetonitrile, 20% water, and 0.05% TFA. The TFA salt was collected and stripped. The residue which contained an impurity from the benzotriazol-1-yloxytris (dimethylamino)phosphonium hexafluorophosphate was then prepped again to give 447 mg of the bis-HCl salt 12 as a yellow solid (23.7% yield). 100% A to 100% B over 25 minutes A=98% water, 2% Acetonitrile, and 26 mmol of Hcl B=80% Acetonitrile, 20% water, and 26 mmol of Hcl $^1$H NMR (300 MHz, D$_2$O): 1.27 (s, 3H); 2.01–2.05 (m, 2H); 2.20 (s, 6H); 2.92 (t, 2H, J=6.2 Hz); 3.13 (s, 3H); 3.19 (dd, 1H, $J_{AB}$=14.1 Hz, $J_{BX}$=10.8 Hz); 3.35–3.48 (m, 4H); 3.61 (dd, 1H, $J_{AB}$=13.9 Hz, $J_{AX}$=3.7 Hz); 3.73–3.75 (m, 2H); 3.87–3.88 (m, 4H); 4.22 (dd, 1H, $J_{AX}$=3.7 Hz, $J_{BX}$=10.8 Hz); 4.34 (t, 2H, J=6.2 Hz); 4.52 (d, 2H, J=4.8 Hz); 6.23 (s, 2H); 6.36 (s, 2H); 7.25 (s, 2H); 7.65 (s, 1H); 7.99 (s, 1H). HRMS calcd for $C_{33}H_{45}N_8O_6S$ [M]$^+$ 681.318279, found 681.319369. Anal. calcd. for $C_{33}H_{44}N_8O_6S$Cl.2HCl: C, 50.16; H, 6.00; N, 14.18; S, 4.06; Cl, 13.46; found: C, 50.11; H, 5.80; N, 13.86; S, 3.75; Cl, 13.59.

Additional Synthesis of Indazole Cores

Compounds of Formula Ia, Ib, or Ic wherein $X^1$, $X^2$, $X^3$ and $X^4$ are all carbon and W is C(=O)NH can be prepared from appropriately substituted 4-, 5-, 6-, or 7-alkoxycarbonyl indazoles, IIIa, wherein R is an alkyl group such as methyl, ethyl or tert-butyl.

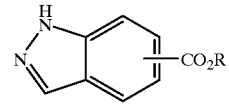

(IIIa)

The requisite indazoles can be conveniently prepared from the commercially available nitrotoluic acids according to the example shown in Scheme 1. Conversion of the acid 1a to a suitable ester, such as the ethyl ester 1b, may be carried out by one of many methods well-known to one skilled in the art of organic synthesis, for example treatment with a suitable base, such as sodium bicarbonate, in a suitable solvent, such as N,N-dimethylformamide, followed by treatment with an alkyl halide, such as iodoethane. Reduction of the nitro group of 1b can be effected in a number of ways known to one skilled in the art of organic synthesis, including treatment with tin(II) chloride in ethanol. The resulting aniline derivative can be converted to the desired substituted indazole IIIa according to the method of Bartsch and Yang (*J. Heterocycl. Chem.* 1984, 21(4): 1063–1064). A variation of the conversion of the aniline 1c to the indazole IIIa proceeds through an N-acylated intermediate 1d, followed by cyclization and deacetylation, according to the method reported by Rüchardt and Hassmann (Liebigs *Ann. Chem.* 1980, 908–927).

The order of the esterification and reduction steps may be reversed, such that the nitrotoluic acid is first converted to an aminotoluic acid, which is then esterified. In some cases other intermediates related to those shown in Scheme 1 are commercially available or may be prepared using methods described in the literature of organic chemistry; in these cases transformations similar to those shown in Scheme 1 may be used to prepare the desired compounds IIIa. For example, commercially available methyl 3-amino-4-methylbenzoate may be directly transformed into 6-methoxycarbonylindazole.

Scheme 1

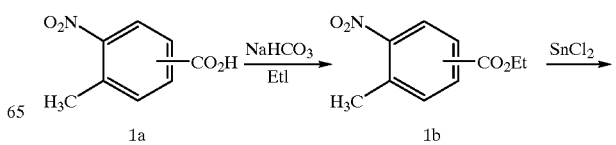

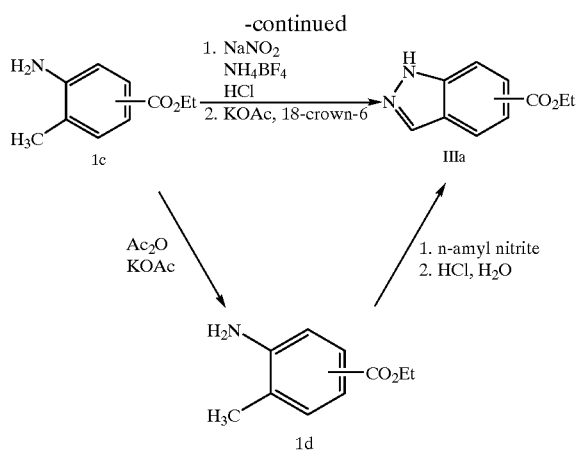

Compounds of Formula Ia or Ib wherein one or more of $X^1$, $X^2$, $X^3$ or $X^4$ are nitrogen may be prepared from the corresponding alkoxycarbonylindazoles IIIb in which the appropriate carbon atom or atoms have been replaced by nitrogen. These may in turn be prepared by substitution of the appropriately substituted heterocycle for the nitrotoluic acids, nitrotoluic acid esters, or aminotoluic acid esters in Scheme 1 above. The starting heterocycles could be obtained by following the procedures and methods in references outlined below, along with implementation of standard functional group transformations well known to one skilled in the art.

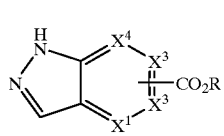

Functionalized pyrazines could be prepared according to procedures outlined in *The Chemistry of Heterocyclic Compounds: The Pyrazines,* Vol. 41 (Arnold Weissberger and Edward C. Taylor, Eds.), John Wiley and Sons (New York: 1982). Preparation of appropriately functionalized pyridazines could be achieved using the methods described in *The Chemistry of Heterocyclic Compounds: Condensed Pyridazines Including Cinnolines and Phthalazines,* Vol. 27 (Arnold Weissberger and Edward C. Taylor, Eds.), John Wiley and Sons (New York: 1973) and *The Chemistry of Heterocyclic Compounds: Pyridazines,* Vol. 28 (Arnold Weissberger and Edward C. Taylor, Eds.), John Wiley and Sons (New York: 1973). For the synthesis of functionalized pyrimidines one could follow procedures in *The Chemistry of Heterocyclic Compounds: The Pyrimidines,* (Arnold Weissberger, Consulting Ed.) John Wiley and Sons (New York: 1962), *The Chemistry of Heterocyclic Compounds: The Pyrimidines,* Supplement I, (Arnold Weissberger and Edward C. Taylor, Consulting Eds.) John Wiley and Sons (New York: 1970), and *The Chemistry of Heterocyclic Compounds: The Pyrimidines,* Supplement II, Vol. 16 (Arnold Weissberger and Edward C. Taylor, Consulting Eds.) John Wiley and Sons (New York: 1985). Functionalized pyridines which can serve as starting materials in Scheme 1 could be made by the methods described in *The Chemistry of Heterocyclic Compounds: Pyridine and Its Derivatives,* Part Four, (Arnold Weissberger, Consulting Ed.) John Wiley and Sons (New York: 1964), *The Chemistry of Heterocyclic Compounds: Pyridine and Its Derivatives,* Supplement Part Two, (Arnold Weissberger and Edward C. Taylor, Consulting Eds.) John Wiley and Sons (New York: 1974), *The Chemistry of Heterocyclic Compounds: Pyridine and Its Derivatives,* Supplement Part Three, Vol. 14 (Arnold Weissberger and Edward C. Taylor, Consulting Eds.) John Wiley and Sons (New York: 1974), *The Chemistry of Heterocyclic Compounds: Pyridine and Its Derivatives,* Supplement Part Four, Vol. 14 (Arnold Weissberger and Edward C. Taylor, Consulting Eds.) John Wiley and Sons (New York: 1975), and *The Chemistry of Heterocyclic Compounds: Pyridine and Its Derivatives,* Part Five, Vol. 14 (Arnold Weissberger and Edward C. Taylor, Consulting Eds.) John Wiley and Sons (New York: 1984). One example of the preparation of an appropriately substituted pyridine starting material is the preparation of 2-methyl-3-aminopyridine-5-carboxylic acid half-sulfate salt, as described by Argoudelis and Kummerow (*J. Org. Chem.* 1961, 26: 3420–3422).

Compounds of Formula Ia wherein $R^{10}$ is not hydrogen may be prepared from appropriately substituted alkoxycarbonylindazoles. Some such substituted alkoxycarbonylindazoles may be prepared using the method outlined in Scheme 1. For example, methyl 4-amino-3-ethylbenzoate may be prepared as described by Witte and Boekelheide (*J. Org. Chem.* 1972, 37 (18): 2849–2853). This compound may be converted to the diazonium fluoroborate and cyclized to 3-methyl-5-methoxycarbonylindazole using the method outlined in Scheme 1. This compound may be used as a starting material for preparation of the corresponding compounds of Formula Ia wherein $R^{10}$ is methyl.

Other substituted alkoxycarbonylindazoles may be prepared from unsubstituted alkoxycarbonylindazoles using the methods outlined in Scheme 2. For example, an ethoxycarbonylindazole may be brominated by treatment with bromine in a suitable solvent, such as acetic acid, to provide the corresponding 3-bromo-ethoxycarbonyl-indazole IIIc. This compound may be coupled with a suitable reagent, alternatively followed by additional synthetic manipulations, to provide the desired 3-substituted-ethoxycarbonylindazole. For example, coupling with phenylboronic acid in the presence of tetrakis-(triphenylphosphine)palladium and triethylamine in N,N-dimethylformamide, using the method of Miyaura, Suginome and Suzuki (*Tetrahedron* 1983, 39: 3271) provides the corresponding 3-phenyl-ethoxycarbonylindazole IIId. Similar methods, starting from compounds of Formula IIIb, may be used to prepare the corresponding compounds wherein one or more of the ring carbons (corresponding to those designated $X^1$, $X^2$, $X^3$ and $X^4$ in Formula Ia) are replaced by nitrogen.

Scheme 2

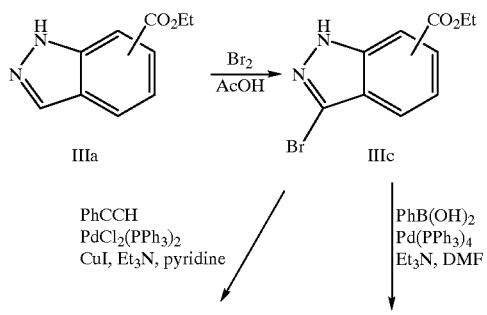

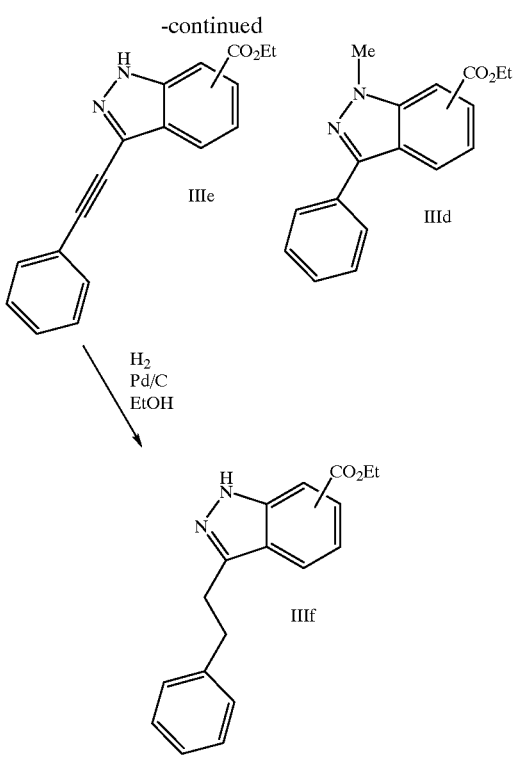

As another example, also shown in Scheme 2, coupling of IIIc with phenylacetylene in the presence of bis-(triphenylphosphine)palladium(II) chloride, copper(I) chloride, and triethylamine in pyridine according to the method of Melissaris and Litt (*J. Org. Chem.* 1992, 57: 6998–6999) provides the corresponding 3-(2-phenylethynyl)ethoxycarbonylindazole IIIe, which may be reduced using hydrogen in the presence of palladium on charcoal to provide the corresponding 3-(2-phenyl-ethyl)ethoxycarbonylindazole IIIf. Similar methods, starting from compounds of Formula IIIb, may be used to prepare the corresponding compounds wherein one or more of the ring carbons (corresponding to those designated $X^1$, $X^2$, $X^3$ and $X^4$ in Formula Ia) are replaced by nitrogen.

Compounds IIIc, IIId, IIIe and IIIf may be used in the preparation of compounds of Formula Ia in which $R^{10}$ is phenyl, 2-phenylethynyl, or 2-phenylethyl, respectively. Alternatively, further manipulations of the substituent may be accomplished at a later stage in the synthesis of the compound of Formula Ia. For example, the 2-phenylethynyl indazoles IIIe may be used in a synthetic sequence during the course of which the acetylene will be reduced, providing ultimately compounds of Formula Ia in which $R^{10}$ is 2-phenylethyl.

Other appropriately substituted alkoxycarbonylindazoles, for use in the preparation of compounds of Formula Ia wherein $R^{10}$ is not hydrogen, may be prepared using other methods known in the art of organic synthesis, such as those outlined in *The Chemistry of Heterocyclic Compounds: Pyrazoles, Pyrazolines, Pyrazolidines, Indazoles and Condensed Rings*, Vol. 22 (Arnold Weissberger, Ed.), John Wiley and Sons (New York: 1967), Chapter 10.

Hereinafter, unless otherwise specified, phrases such as "indazoles III" and "indazoles of Formula III" are meant to include simple indazoles IIIa, mono- or diazaindazoles IIIb, and substituted indazoles such as but not restricted to IIIc, IIId, IIIe and IIIf. Substituted mono- and diazaindazoles such as but not restricted to mono- and diaza analogs of IIIc, IIId, IIIe and IIIf are also included.

Compounds of Formula Ia may be prepared from indazoles III as outlined in Scheme 3. Alkylation of the indazoles of Formula III with a suitably functionalized alkyl halide can be effected in a variety of ways known to one skilled in the art. For example, using a method similar to that described by Granger et al. (*Chim. Ther.* 1970, 5: 24), an indazole of Formula III is treated with a suitable base, such as potassium bis(trimethylsilyl)amide, followed by addition of the alkyl halide, for example, 3-bromopropylphthalimide. Alternately, the alkylation can be carried out utilizing Mitsunobu conditions (Mitsunobu, *Synthesis*, 1981, 1–28) by addition of the corresponding alcohol, 3-hydroxypropylphthalimide, to a mixture of diethyl azodicarboxylate and triphenylphosphine in a suitable solvent, usually dry tetrahydrofuran, followed by addition of the indazole III. Separation, if necessary, of the mixture of 1- and 2-substituted isomers by chromatography provides the desired 1-alkylated product 3a. Removal of the phthalimide may be achieved by treatment with anhydrous hydrazine to give the primary amine 3b.

Scheme 3

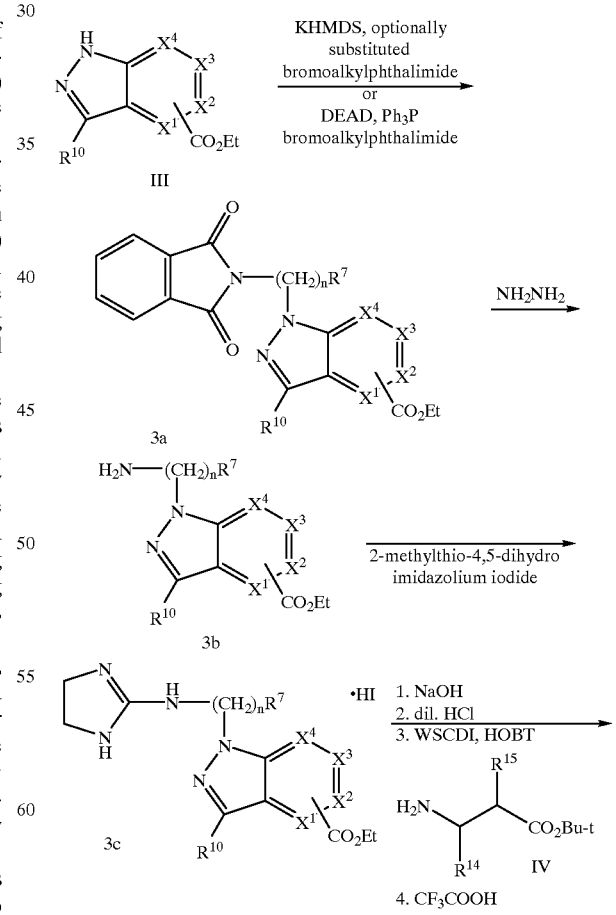

-continued

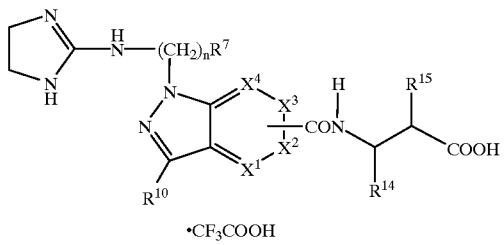

•CF₃COOH

-continued

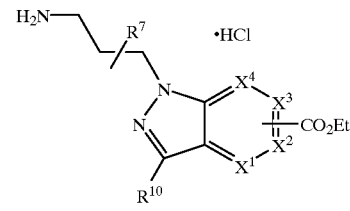

3b

As further shown in Scheme 3, 2-imidazolinylaminoalkylindazoles may be prepared by treatment of the amine 3b with a suitable reagent such as 2-methylthio-4,5-dihydroimidazolium iodide. Hydrolysis of the ester, using conventional methods known to one skilled in the art of organic synthesis, may be followed by coupling of the resulting acid to an appropriately substituted α- or β-amino ester such as a compound of Formula IV, to provide an intermediate which, after deprotection, affords compounds of Formula Ia wherein $R^1$ is 2-imidazolinylaminoalkyl. The coupling may be carried out using any of the many methods for the formation of amide bonds known to one skilled in the art of organic synthesis. Those methods include, but are not limited to, use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides (WSCDI)) method, active ester (p-nitrophenyl ester, N-hydroxysuccinic imido ester) method, or by the use of one of many other known coupling reagent such as BOP-Cl. Some of these methods (especially the carbodiimide method) can be enhanced by the addition of 1-hydroxybenzotriazole to the reaction mixture.

An alternative method for preparing amines 3b wherein n=3 is outlined in Scheme 4. Alkylation of the indazole III may be achieved by treatment with an optionally substituted acrylonitrile in the presence of a catalytic amount of a base such as sodium ethoxide or sodium bis(trimethylsilyl)amide, in a suitable solvent such as ethanol, to provide the intermediate nitrile 4a. This may be converted to the amine 3b by reduction using any of a number of methods known to one skilled in the art of organic synthesis, such as by treatment with hydrogen in the presence of a catalyst such as palladium on charcoal. An acid such as aqueous hydrochloric acid may be added to the reaction mixture to minimize side reactions during the reduction.

Appropriately substituted racemic β-amino acids IV (used in Scheme 3) may be purchased commercially or, as is shown in Scheme 5, Method 1, prepared from the appropiate aldehyde, malonic acid and ammonium acetate according to the procedure of Johnson and Livak (*J. Am. Chem. Soc.,* 1936, 58, 299). Racemic β-substituted-β-amino esters may be prepared through the reaction of dialkylcuprates or alkyllithiums with 4-benzoyloxy-2-azetidinone followed by treatment with anhydrous ethanol (Scheme 5, Method 2) or by reductive amination of β-keto esters as is described in WO93/16038 (also see Rico et al., *J. Org. Chem.,* 1993, 58, 7948–51). Enantiomerically pure β-substituted-β-amino acids can be obtained through the optical resolution of the racemic mixture or can be prepared using numerous methods, including: Arndt-Eistert homologation of the corresponding α-amino acids as shown in Scheme 5, Method 3 (see Meier and Zeller, *Angew. Chem. Int. Ed. Engl.,* 1975 14, 32; Rodriguez et al., *Tetrahedron Lett.,* 1990, (31), 5153; Greenlee, *J. Med. Chem.* 1985, 28, 434 and references cited within); and through an enantioselective hydrogenation of a dehydroamino acid as is shown in Scheme 5, Method 4 (see *Asymmetric Synthesis,* Vol. 5, (Morrison, ed.) Academic Press, New York: 1985). A comprehensive treatise on the preparation of β-amino acid derivatives may be found in patent application WO 93/07867, the disclosure of which is hereby incorporated by reference.

Scheme 5

Method 1

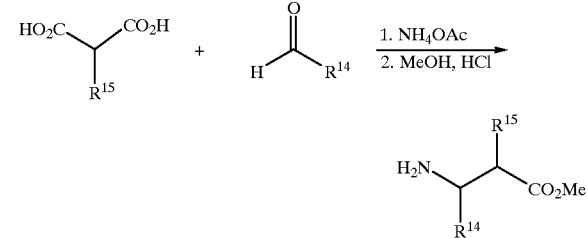

Method 2

Method 3

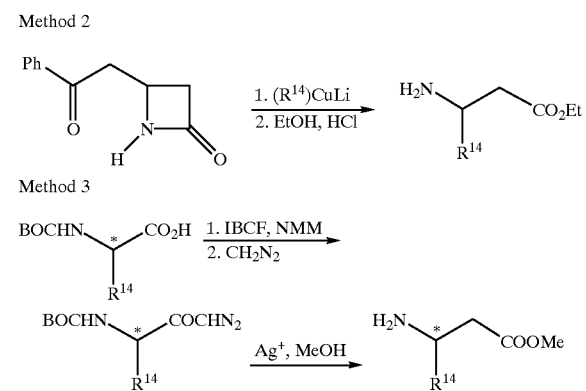

Scheme 4

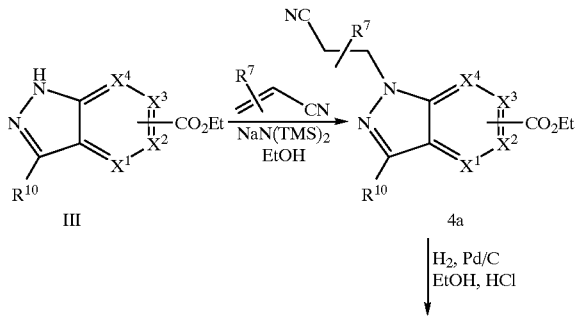

Method 4

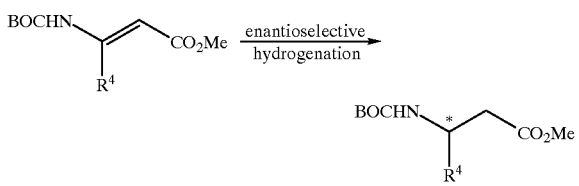

The synthesis of $N^2$-substituted diaminopropionic acid derivatives IV can be carried out via Hoffmann rearrangement of a wide variety of asparagine derivatives as described, for example, by Waki et al. (*Synthesis* 1981, 266–267) or by Moore et al. (*J. Med. Chem.* 1976, 19(6), 766–772). An example is shown in Scheme 6, Method 1. They may also be prepared by manipulations, which will be familiar to one skilled in the art of organic synthesis, of the commercially available 3-amino-2-benzyloxycarbonylaminopropionic acid. An example is shown in Scheme 6, Method 2.

Scheme 6

Method 1

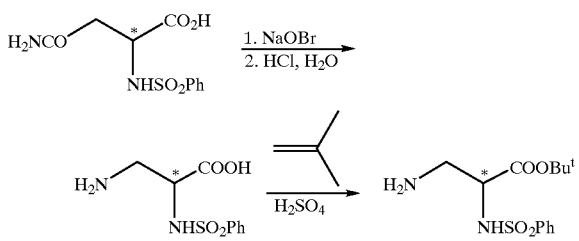

Method 2

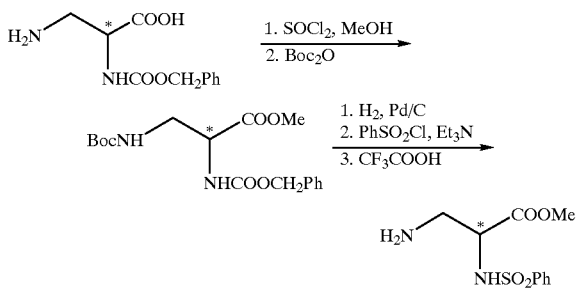

Compounds of Formula Ia above wherein $R^1$ is 2-pyridinylaminoalkyl may be prepared by the method outlined in Scheme 7. Treatment of the intermediate aminoalkylindazole 3b from Scheme 3 (or the corresponding salt from Scheme 4) with 2-chloropyridine N-oxide hydrochloride, using a modification of the method described by Misra, et al. (*Bioorg. and Med. Chem. Letters,* 1994, 4, 2165–2170), and subsequent reduction of the resulting N-oxide derivative 7a provides a 2-pyridinylaminoalkyl intermediate 7b. This reduction may be performed using a number of methods known to one skilled in the art of organic synthesis, such as that using ammonium formate in the presence of 10% palladium on charcoal in refluxing ethanol, as described by Balicki (*Synthesis,* 1989, 645–646), or by reduction with hydrogen in the presence of a catalyst such as palladium on charcoal or Raney nickel, or by treatment with triph- enylphosphine. The resulting 2-aminopyridine moiety of 7b may be optionally protected, for example by treatment with di-t-butyldicarbonate in dry tetrahydrofuran in the presence of a suitable base, such as triethylamine or N,N-dimethylaminopyridine, using the method of Iwanowicz (*Synth. Commun.,* 1993, 23(10), 1443–1445), to provide intermediate 7c. Ester hydrolysis, coupling and deprotection as outlined in Scheme 3 can then provide the desired compounds of Formula Ia.

Scheme 7

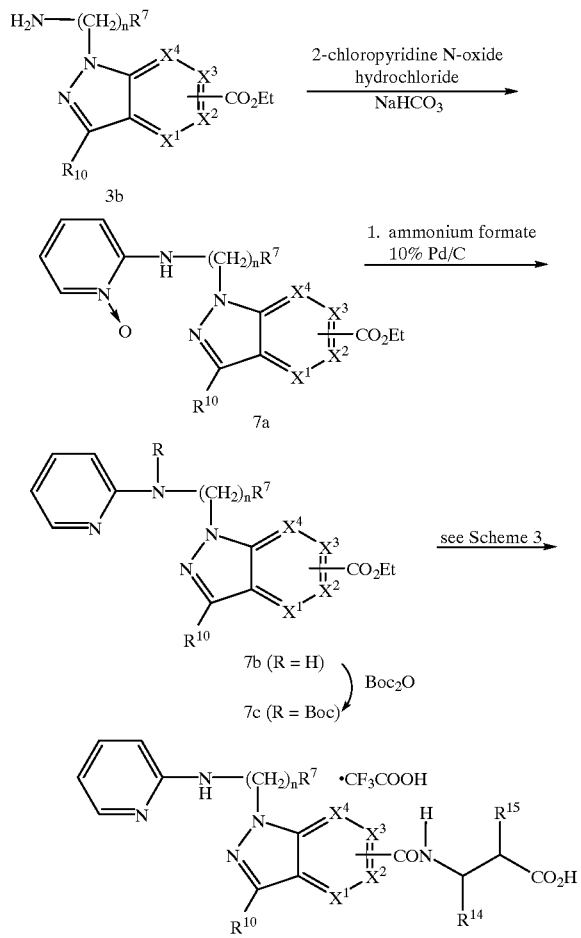

An alternative route to 1-(heteroarylaminoalkyl) indazoles of Formula Ia is outlined in Scheme 8. A suitable indazole III can be alkylated with an alkyl halide bearing a protected aldehyde, such as a 1,3-dioxolane, using conditions described above (see Scheme 3) to provide 8a. Deprotection to the aldehyde 8b, for example by treatment with aqueous acid, may be followed by reductive amination with a heteroarylamine such as 2-aminopyridine or a suitably protected 2-aminoimidazole, such as 1-triphenylmethyl-2-aminoimidazole, in the presence of a reducing agent such as sodium triacetoxyborohydride or sodium cyanoborohydride, to provide the 1-(heteroarylaminoalkyl)indazole 8c. The intermediates 8c can then be elaborated to the corresponding compounds of Formula Ia, for example as described in Scheme 3.

Scheme 8

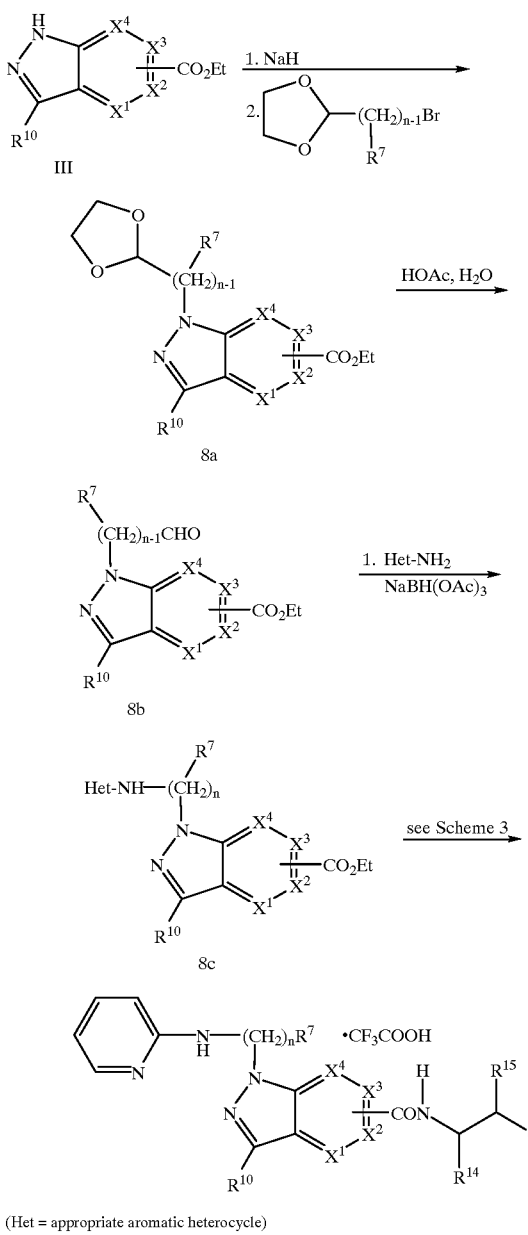

(Het = appropriate aromatic heterocycle)

Scheme 9

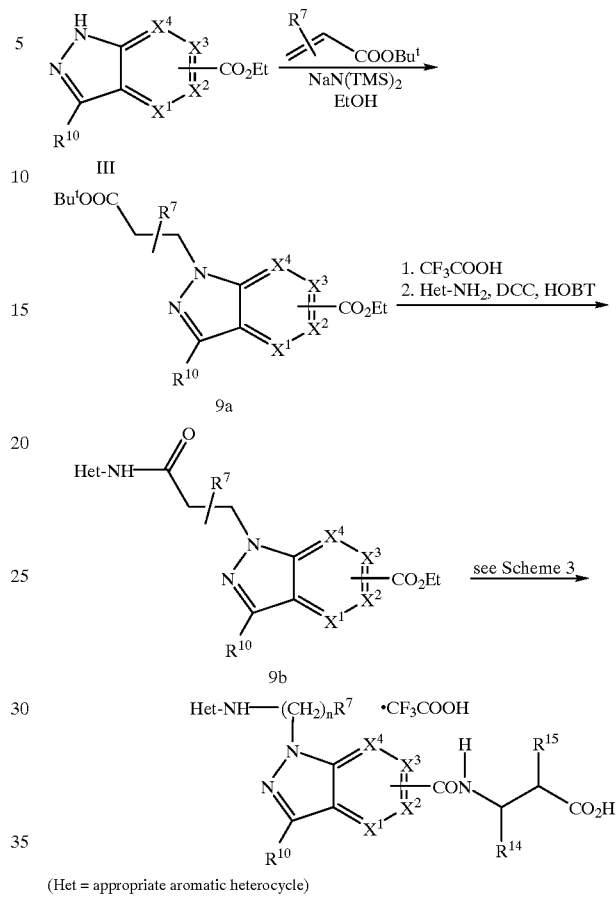

(Het = appropriate aromatic heterocycle)

A route to 1-(heteroarylaminocarbonylethyl) indazoles of Formula Ia is outlined in Scheme 9. A suitable indazole III can be alkylated by treatment with an acrylic acid ester such as tert-butyl acrylate, using a method such as that described in Scheme 4. Removal of the ester of 9a may be followed by conversion to a heteroaryl amide by treatment with a heteroaryl amine using any of a number of methods well known to one skilled in the art of organic synthesis. The resulting 1-(heteroarylaminocarbonylethyl)indazole 9b can then be elaborated to the corresponding compounds of Formula Ia, for example as described in Scheme 3.

Compounds of Formula Ib may be prepared according to the method outlined in Scheme 10. Thus, the appropriate indazole III may be alkylated by treatment with a suitable base, for example sodium hydride, followed by addition of a suitable alkylating agent such as an alkyl halide $R^9$—Br or $R^9$—I. Bromination of the intermediate 10a using, for example, bromine in acetic acid, provides the corresponding 3-bromo derivative 10b. (The order of these two synthetic steps may also be reversed. That is, the indazole III may be brominated, and resulting bromoindazole may be alkylated, to provide similar products 10b.) Coupling of 10b with, for example, 3,3-diethoxy-1-propyne, under conditions similar to those described by Sakamoto et al. (*Synthesis* 1992, 746–748) provides a functionalized alkynyl derivative 10c. Reduction of the acetylenic bond of 10c using, for example, hydrogen in the presence of a catalyst such as palladium on charcoal, followed by hydrolysis of the acetal with aqueous acid provides an aldehyde intermediate 10d which, using methods analogous to those outlined in Scheme 8, may be elaborated to an intermediate 10e containing a heteroarylaminoalkyl substituent at the 3-position. This intermediate may then in turn be elaborated to the desired compounds of Formula Ib, for example using methods described in Scheme 3.

Scheme 10

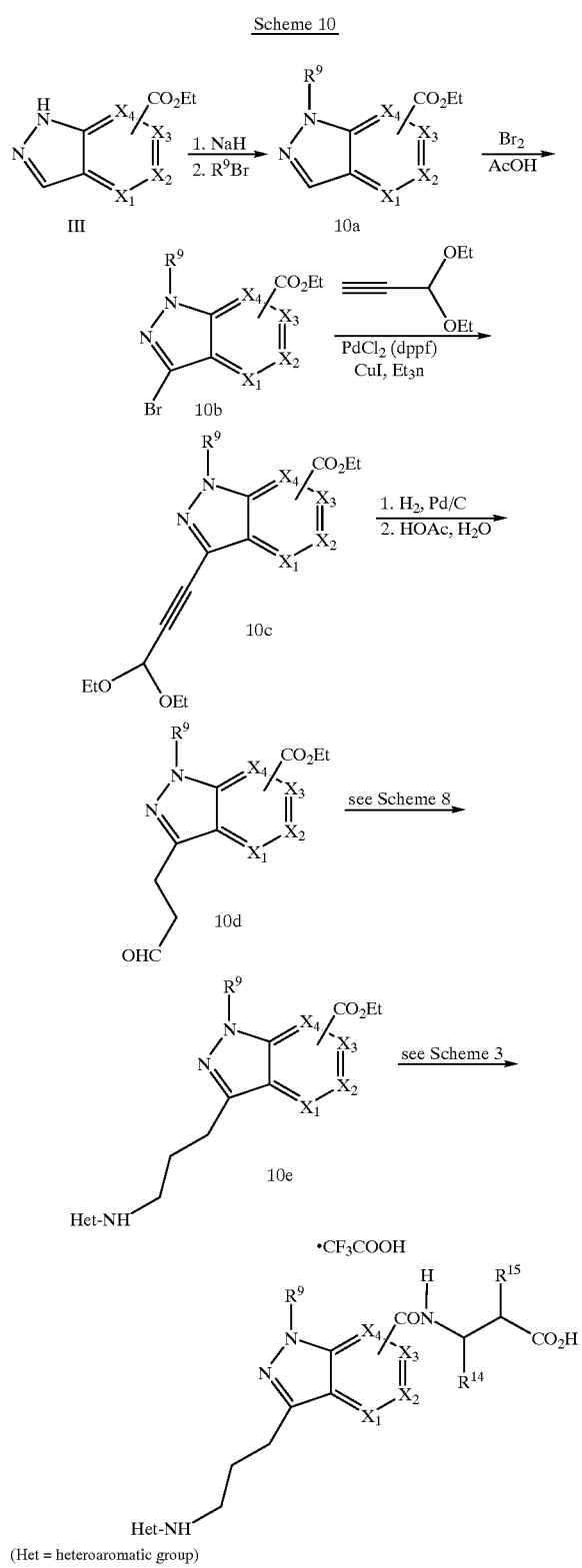

(Het = heteroaromatic group)

Compounds of Formula Ib may alternatively be prepared from the intermediate 10b according to the method described in Scheme 11. Thus, coupling of 10b under conditions similar to those described by Murakami et al. (*Heterocycles,* 1990, 31(8), 1505–11) can provide a 3-allyl derivative 11a. Hydroboration as described by Brown and Subba Rao (*J. Am. Chem. Soc.* 81, 6428–6433) can provide the alcohol 11b, which may be subjected to the Mitsunobu reaction (vide supra) with phthalimide followed by deprotection to provide an amine intermediate 11c which, analogously to the method shown in Schemes 10 and 3, can be elaborated to the desired compounds of Formula Ib. Alternatively, the intermediate 11b may be prepared by reduction of the aldehyde 10d shown in Scheme 10. Other methods can be used for the conversion of intermediates 10d and 11b to the primary amine 11c which are known to those skilled in the art of organic synthesis.

Scheme 11

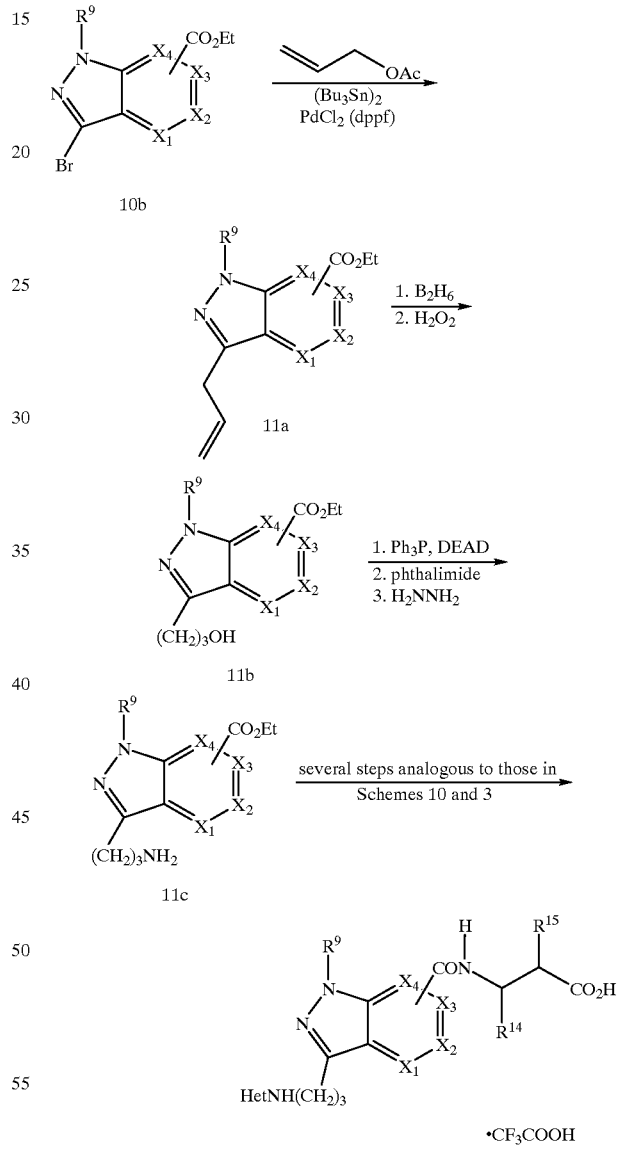

(Het = heterocyclic group)

Compounds of Formula Ic may be prepared according to methods outlined in Scheme 12. Treatment of the appropriate indazole starting material 12a with zinc bromide and vinylmagnesium bromide followed by dichloro[1,1'-bis (diphenylphosphino) ferrocene]palladium (II), using a procedure similar to that described by Brown, et al. (U.S. Pat. No. 4,898,863), can provide the desired 3-vinyl derivative 12b. Treatment of this compound with ozone (F. J. Brown, et al. Ibid.), can provide an aldehyde 12c. Oxidation using silver(I) oxide, as described by Campaigne and LeSuer (*Organic Syntheses,* 1963, Coll. Vol. 4, 919), can provide the desired carboxylic acid 12d. Esterification and deprotection of the ether oxygen of 12e using boron tribromide, by a method analogous to that detailed by Manson and Musgrave (*J. Chem. Soc.* 1011 (1963)), can provide the hydroxy intermediate 12f. Mitsunobu coupling, (vide supra), followed by further transformations of 12g similar to those shown in Scheme 3, can provide compounds of Formula Ic.

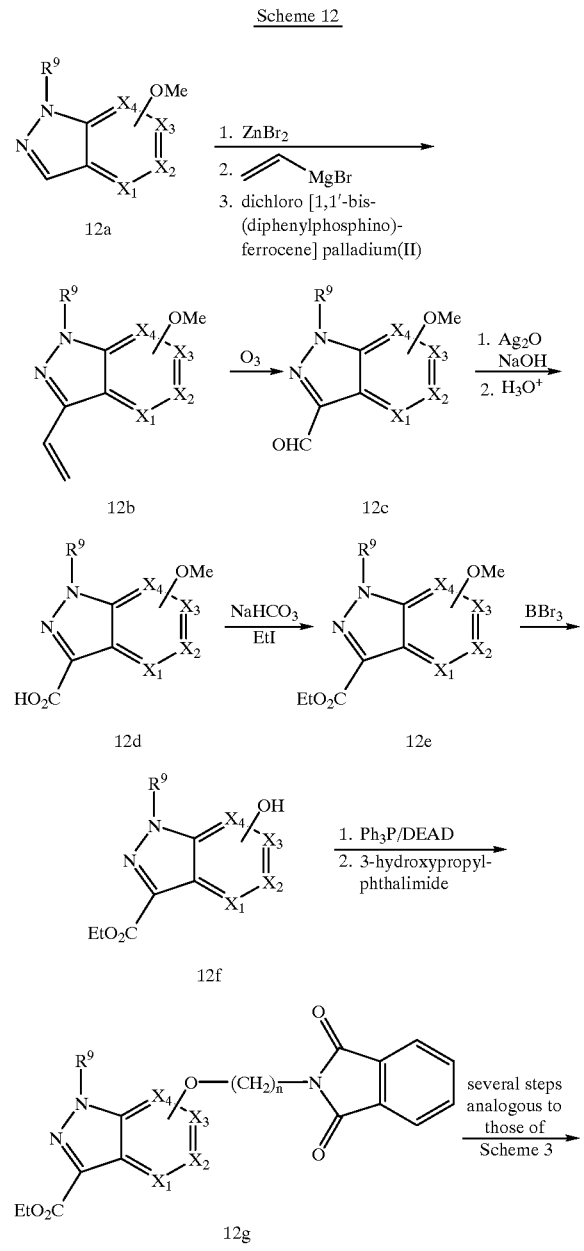

-continued

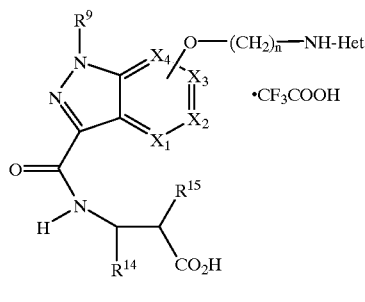

(Het = heteroaryl)

Additional alcohols useful for the preparation of compounds of Formula Ia, Ib and Ic through the Mitsunobu reaction described in the above schemes may be prepared as described in Scheme 13.

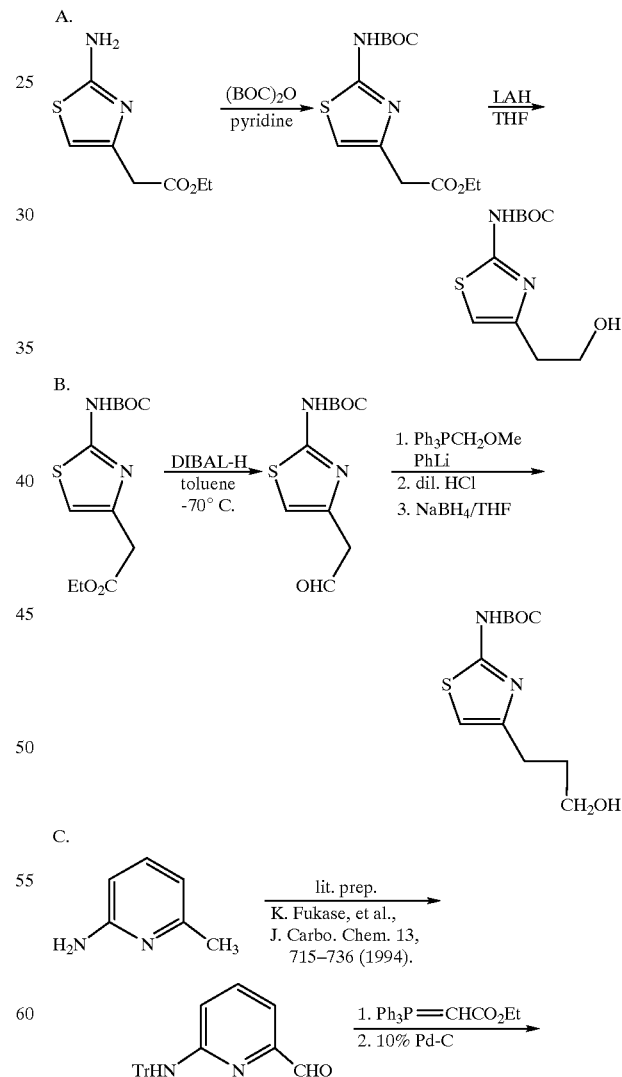

-continued

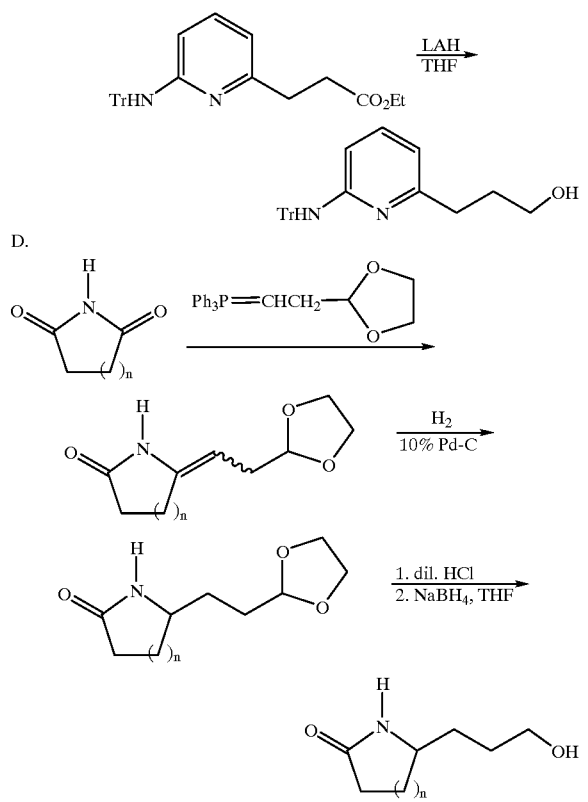

D.

E.

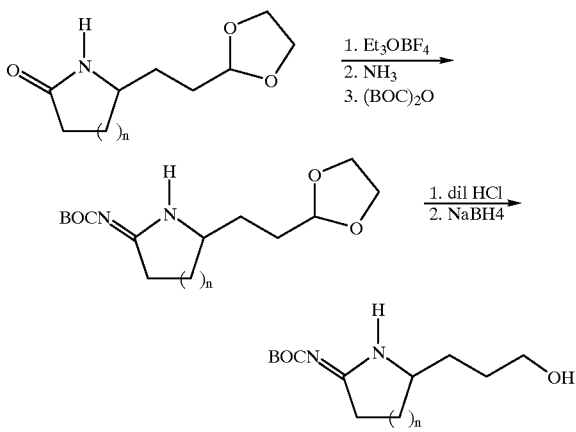

Various compounds of Formula Ia, Ib or Ic may be prepared from a common derivative of the corresponding compounds of Formula Ia, Ib or Ic by functional group manipulations familiar to one skilled in the art of organic synthesis. As one example, preparation of compounds of Formula Ia having different sulfonamide substituents at $R^{16}$ may be achieved as outlined in Scheme 14. Thus, the compound of Formula Ia having a benzyloxycarbonylamino group at $R^{16}$ (14a) may be hydrogenolyzed using, for example, hydrogen in the presence of a catalyst such as palladium on charcoal to provide the primary amine derivative 14b. This may be reacted with a sulfonylating agent such as $R^{17}SO_2Cl$ in the presence of an amine such as triethylamine to provide, after deprotection of the ester, the desired compound of Formula Ia. In place of the sulfonyl chloride, use of a carboxylic acid, acid chloride or acid anhydride can provide the corresponding amide derivative, use of a chloroformate can provide the corresponding carbamate derivative, use of a sulfamoyl chloride can provide the corresponding sulfamide derivative, and use of an isocyanate can provide the corresponding urea derivative.

Scheme 14

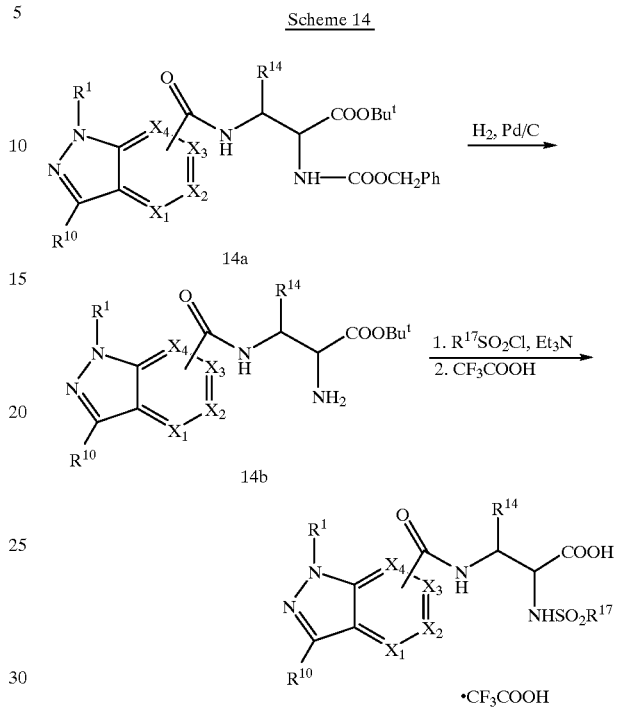

As another example, compounds of Formula Ia with different variations in $R^1$ may be prepared from a common precursor as outlined in Scheme 15. Thus, the amine intermediate 3b may be reacted, for example, with benzyl chloroformate to provide the benzyl carbamate. Hydrolysis of the ester, for example with lithium hydroxide, can provide the acid intermediate 15a. Using methods described earlier, 15a may be reacted with, for example, a suitable beta-amino ester, followed by removal of the benzyl carbamate, for example by hydrogenolysis, to provide the amine intermediate 15b. Using, for example, steps analogous to those shown in Schemes 3 or 7, the amine may be converted to an aminoheterocyclic group. After deprotection of the ester, the desired compound of Formula Ia may be obtained.

Scheme 15

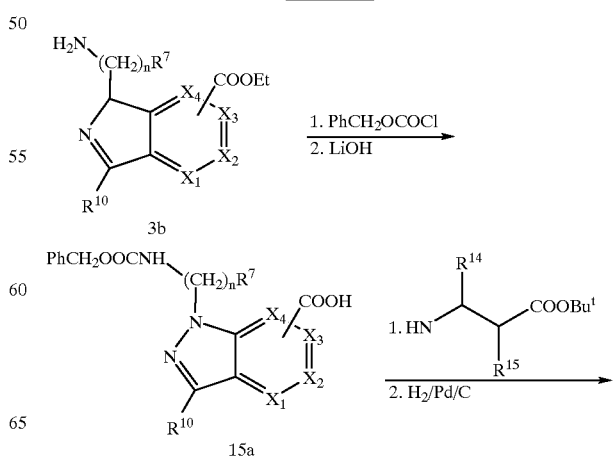

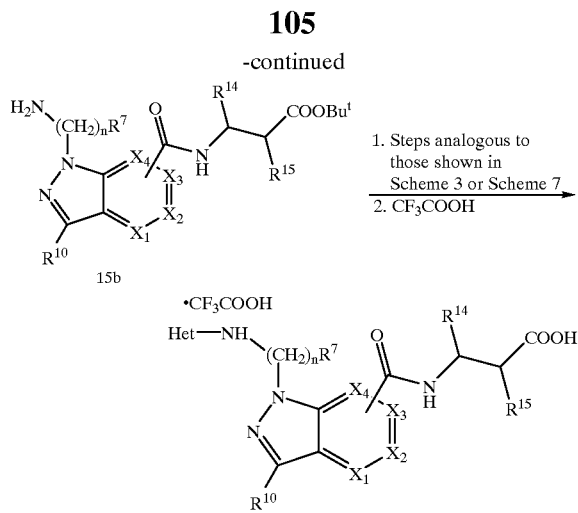

The example outlined in Scheme 15 will also serve to demonstrate that the order in which the different substituents are elaborated to give the compounds of Formula Ia, Ib and Ic may be varied from that in the examples shown in Schemes 1 through 14. This example will also serve to demonstrate the use of protecting groups to temporarily protect a functional group in the course of a synthetic sequence when that functional group is not compatible with one or more of the synthetic transformations that are to be accomplished. Such use of protecting groups, while not always explicitly shown in Schemes 1 through 15, is well known to one skilled in the art of organic synthesis. Many examples of protecting groups may be found, for example, in Greene, "Protective Groups in Organic Syntheses", Wiley (New York), 1981.

The detailed processes for preparing the compounds of Formula Ia, Ib or Ic are illustrated by the following Examples. It is, however, understood that this invention is not limited to the specific details of these examples. Reactions were run under an atmosphere of nitrogen unless otherwise indicated. Solvent removal from reaction mixtures, extracts, and the like was performed under vacuum on a rotary evaporator. Flash chromatography refers to the medium-pressure column chromatography method described by Still et al. (*J. Org. Chem.* 1978, 43(14), 2923–2925). Melting points (mp) are uncorrected. Proton nuclear magnetic resonance spectra (NMR) were measured in chloroform-d (CDCl$_3$), dimethyl sulfoxide-d$_6$ (DMSO-d$_6$) or methanol-d$_4$ (MeOH-d$_4$) and the peaks are reported in parts per million downfield from tetramethylsilane (δ). The coupling patterns are reported as follows: s, singlet; d, doublet; t, triplet; q, quartet; m, multiplet; b, broad. Mass spectra were measured using electrospray ionization (ESI), ammonia chemical ionization (NH$_3$—CI), fast-atom bombardment from a glycol matrix (FAB), or electron impact ionization (EI).

ADDITIONAL EXAMPLES

The following examples provide physical characterization of compounds useful in the present invention. A full synthetic disclosure of such compounds was published in WO 97/23480 on Jul. 3, 1997.

Example 1035b

3-[1-[3-(N-imidazol-2-ylamino)propyl]-indazol-5-ylcarbonyl-amino]-2(S)-(2,6-dimethyl-4-phenylbenzene-sulfonylamino)-propionic acid trifluoroacetate $^1$H NMR (MeOH-d$_4$) δ8.12 (s, 2H), 7.72 (dd, 1H), 7.54 (d, 1H), 6.76 (s, 2H), 6.73 (s, 2H), 4.53 (t, 2H), 4.16 (dd, 1H), 3.76 (dd, 1H), 3.49 (dd, 1H), 3.23 (t, 2H), 2.56 (s, 6H), 2.22 (m, 2H), 1.98 (s, 3H); High resolution mass spectrum (FAB) calculated (M+H$^+$) 554.2186, found 554.2196.

Example 1050e

3-[1-[3-(N-imidazol-2-ylamino)propyl]indazol-5-ylcarbonylamino]-2(S)-(2,6-dimethyl-4-phenylbenzene-sulfonylamino)propionic acid trifluoroacetate $^1$H NMR (MeOH-d$_4$) δ8.06 (s, 1H), 7.95 (s, 1H), 7.63 (d, 1H), 7.34 (d, 1H), 7.28 (m, 5H), 7.09 (s, 2H), 6.75 (s, 2H), 4.34 (t, 2H), 4.27 (dd, 2H), 3.77 (dd, 1H), 3.47 (dd, 1H), 3.17 (t, 2H), 2.66 (s, 6H), 2.12 (m, 2H); High resolution mass spectrum (FAB) calculated (M+H$^+$) 616.2342, found 616.2324.

Example 1081

3-[1-[3-(N-pyridin-2-ylamino)propyl]indazol-5-ylcarbonylamino]-2(S)-(benzyloxycarbonylamino) propionic acid trifluoroacetate $^1$H NMR (DMSO-d$_6$) δ8.57 (bm, 1H), 8.53 (bt, 1H), 8.26 (s, 1H), 8.21 (s, 1H), 7.82 (m, 3H), 7.69 (d, 1H), 7.59 (d, 1H), 7.28 (m, 5H), 6.93 (d, 1H), 6.78 (t, 1H), 4.99 (s, 2H), 4.52 (t, 2H), 4.23 (m, 1H), 3.60 (m, 2H), 3.24 (m, 2H), 2.15 (m, 2H); High resolution mass spectrum (FAB) calculated (M+H$^+$) 517.2199, found 517.2213.

Example 1094

3-[1-[3-(N-pyridin-2-ylamino)propyl]indazol-5-yl-carbonylamino]-2(S)-(isobutyloxycarbonylamino) propionic acid trifluoroacetate $^1$H NMR (DMSO-d$_6$) δ8.56 (m, 2H), 8.30 (s, 1H), 8.25 (s, 1H), 7.90–7.75 (m, 3H), 7.72 (d, 1H), 7.44 (d, 1H), 6.96 (d, 1H), 6.80 (t, 1H), 4.56 (t, 2H), 4.24 (m, 1H), 3.73 (d, 2H), 3.62 (m, 2H), 3.28 (m, 2H), 2.17 (m, 2H), 1.82 (m, 1H), 0.85 (d, 6H); High resolution mass spectrum (NH$_3$—CI) calculated (M+H$^+$) calculated 483.2348, found 483.2356.

Example 1099b

3-[1-[3-(N-pyridin-2-ylamino)propyl]indazol-5-yl-carbonylamino]-2-(S)-(E-[phenylethenyl] carbonylamino)-propionic acid trifluoroacetate $^1$H NMR (DMSO-d$_6$) δ8.64 (t, 1H), 8.47 (d, 1H), 8.31 (s, 1H), 8.04 (s, 1H), 7.90–7.80 (m, 3H), 7.73 (d, 1H), 7.58 (d, 1H), 7.50–7.35 (m, 6H), 6.98 (d, 1H), 6.82 (t, 1H), 6.74 (d, J=17 Hz, 1H), 4.63 (m, 1H), 4.55 (t, 2H), 3.75–3.55 (m, 2H), 3.27 (m, 2H), 2.18 (m, 2H); High resolution mass spectrum (FAB) calculated (M+H$^+$) 513.2250, found 513.2239.

Example 1108b

3-[1-[3-(N-pyridin-2-ylamino)propyl]indazol-5-yl-carbonylamino]-2(S)-(cyclohexylcarbonylamino) propionic acid trifluoroacetate $^1$H NMR (DMSO-d$_6$) δ8.54 (m, 1H), 8.28 (s, 1H), 8.25 (s, 1H), 8.02 (d, 1H), 7.9–7.7 (m, 4H), 6.90 (m, 1H), 6.77 (m, 1H), 4.55 (t, 2H), 4.44 (m, 1H), 3.61 (m, 2H), 3.26 (m, 2H), 2.16 (m, 3H), 2.0–1.0 (m, 10H); High resolution mass spectrum (NH$_3$—CI) calculated (M+H$^+$) 493.2563, found 493.2559.

Example 1110a

3-[1-[3-(N-pyridin-2-ylamino)propyl]indazol-5-ylcarbonylamino]-2(S)-(phenylaminocarbonylamino)-propionic acid trifluoroacetate $^1$H NMR (MeOH-d$_4$) δ8.24 (s, 1H), 8.09 (s, 1H), 7.85–7.70 (m, 2H), 7.68 (d, 1H), 7.55 (d, 1H), 7.29 (m, 2H), 7.17 (t, 2H), 6.91 (m, 2H), 6.79 (t, 1H), 4.66 (m, 1H), 4.54 (t, 2H), 3.88 (dd, 1H), 3.77 (dd, 1H), 3.27 (m, 2H), 2.28 (m, 2H); High resolution mass spectrum (FAB) calculated (M+H$^+$) 502.2203, found 502.2196.

Example 1129

3-[1-[3-(N-pyridin-2-ylamino)propyl]indazol-5-yl-carbonylamino]-2(S)-(1-naphthalene-sulfonylamino)-propionic acid trifluoroacetate $^1$H NMR (DMSO-d$_6$) δ8.60 (m, 3H), 8.39 (bt, 1H), 8.21 (s, 1H), 8.09 (d, 2H), 8.05 (s, 1H), 7.90 (t, 2H), 7.83 (t, 1H), 7.67 (m, 3H), 7.55 (m, 2H), 6.97 (d, 1H), 6.81 (t, 1H), 4.56 (t, 2H), 4.08 (q, 1H), 3.53 (m, 1H), 3.30 (m, 3H), 2.18 (m, 2H); High resolution mass spectrum (FAB) calculated (M+H$^+$) 573.1947, found 573.1928.

Example 1129a

3-[1-[3-(N-pyridin-2-ylamino)propyl]indazol-5-yl-carbonylamino]-2(S)-(4-phenylbenzenesulfonylamino)-propionic acid trifluoroacetate $^1$H NMR (MeOH-d$_4$) δ8.16 (s, 1H), 8.08 (s, 1H), 7.85 (d, 2H), 7.8–7.7 (m, 4H), 7.58 (d, 2H), 7.5–7.3 (m, 6H), 6.9–6.75 (m, 2H), 4.48 (t, 2H), 4.23 (m, 1H), 3.78 (dd, 1H), 3.50 (dd, 1H), 3.26 (m, 2H), 2.26 (m, 2H); High resolution mass spectrum (FAB) calculated (M+H$^+$) 599.2077, found 599.2062.

Example 1155

3-[1-[3-(N-pyridin-2-ylamino)propyl]indazol-5-yl-carbonylamino]-2(S)-(benzylaminosulfonylamino)propionic acid trifluoroacetate $^1$H NMR (DMSO-d$_6$) δ8.56 (m, 2H), 8.33 (s, 1H), 8.24 (s, 1H), 7.90–7.70 (m, 4H), 7.49 (d, 1H), 7.43 (t, 1H), 7.23 (m, 5H), 6.96 (d, 1H), 6.80 (t, 1H), 4.56 (t, 2H), 4.20–3.60 (m, 5H), 3.59 (m, 2H), 2.18 (t, 2H); High resolution mass spectrum (FAB) calculated (M+H$^+$) 552.2029, found 552.2042.

Example 1178b

3-[1-[3-(N-3,4,5,6-Tetrahydropyrimidin-2-ylamino)-propyl]indazol-5-ylcarbonylamino]-2(S)-(2,4,6-trimethylbenzenesulfonylamino)propionic acid trifluoroacetate $^1$H NMR (DMSO-d$_6$) δ8.46 (bt, 1H), 8.24 (s, 1H), 8.19 (s, 1H), 8.07 (d, 1H), 7.79 (d, 1H), 7.32 (bt, 1H), 6.84 (s, 2H), 4.47 (t, 2H), 4.02 (m, 1H), 3.6–3.4 (m, 2H), 3.21 (m, 4H), 3.03 (m, 2H), 2.52 (s, 6H), 2.07 (s, 3H), 2.05 (m, 2H), 1.78 (m, 2H); Mass spectrum (ESI) m/z 570.5 (100%, M+H$^+$).

Example 1198

3-[1-[3-(N-4,5-Dihydroimidazol-2-ylamino)propyl]indazol-5-ylcarbonylamino]-2(S)-(benzyloxycarbonylamino)-propionic acid trifluoroacetate $^1$H NMR (DMSO-d$_6$) δ8.57 (bt, 1H), 8.31 (s, 1H), 8.28 (m, 1H), 8.24 (s, 1H), 7.88 (d, 1H), 7.72 (d, 1H), 7.62 (m, 1H), 7.32 (m, 5H), 5.02 (s, 2H), 4.47 (t, 2H), 4.29 (m, 1H), 3.65 (m, 2H), 3.55 (s, 4H), 3.11 (q, 2H), 2.06 (m, 2H); High resolution mass spectrum (FAB) calculated (M+H$^+$) 508.2308, found 508.2323.

Example 1213

3-[1-[3-(N-4,5-Dihydroimidazol-2-ylamino)propyl]indazol-5-ylcarbonylamino]-2(S)-(benzenesulfonylamino)propionic acid trifluoroacetate $^1$H NMR (DMSO-d$_6$) δ8.56–7.08 (m, 15H), 4.54–2.01 (m, 13H); High resolution mass spectrum calculated (M+H$^+$) 514.1873, found 514.1879.

Example 1216b

3-[1-[3-(N-4,5-Dihydroimidazol-2-ylamino)propyl]indazol-5-ylcarbonylamino]-2(S)-(2,4,6-trimethylbenzenesulfonyl-amino)propionic acid trifluoroacetate $^1$H NMR (MeOH-d$_4$) δ8.16 (s, 2H), 7.79 (d, 1H), 7.59 (d, 1H), 6.76 (s, 2H), 4.52 (t, 2H), 4.16 (dd, 1H), 3.77 (dd, 1H), 3.59 (s, 4H), 3.47 (dd, 1H), 3.16 (m, 2H), 2.57 (s, 6H), 2.18 (m, 2H), 2.02 (s, 3H); High resolution mass spectrum (FAB) calculated (M+H$^+$) 556.2372, found 556.2342.

Example 1326b

3-[1-[1-(RS)-Methyl-3-(N-pyridin-2-ylamino) propyl]-indazol-5-ylcarbonylamino]-2(S)-(2,4,6-trimethylbenzenesulfonylamino)propionic acid trifluoroacetate $^1$H NMR (DMSO-d$_6$) δ8.43 (bt, 2H), 8.27 (s, 1H), 8.17 (s, 1H), 8.06 (d, 1H), 7.8–7.6 (m, 4H), 6.87 (d, 1H), 6.82 (d, 2H), 6.74 (t, 1H), 5.02 (m, 1H), 4.02 (q, 1H), 3.57 (m, 1H), 3.40 (m, 1H), 3.07 (m, 2H), 2.53 (s, 6H), 2.37 (m, 1H), 2.21 (m, 1H), 2.05 (s, 3H), 1.52 (d, 3H); High resolution mass spectrum (FAB) calculated (M+H$^+$) 579.2390, found 579.2405.

Example 1326f

3-[1-[3-(N-pyridin-2-ylamino)propyl]-3-phenylindazol-5-ylcarbonylamino]-2(S)-(2,4,6-trimethylbenzenesulfonylamino)propionic acid trifluoroacetate $^1$H NMR (DMSO-d$_6$) δ8.61 (bt, 1H), 8.38 (s, 1H), 8.08 (d, 1H), 8.01 (d, 2H), 7.88 (d, 1H), 7.82 (d, 1H), 7.75 (d, 1H), 7.71 (bm, 1H), 7.57 (t, 2H), 7.47 (t, 1H), 6.86 (bd, 1H), 6.72 (bt, 1H), 6.70 (s, 2H), 4.61 (t, 2H), 4.07 (m, 1H), 3.58 (m, 1H), 3.5–3.3 (m, 3H), 2.51 (s, 6H), 2.23 (m, 2H), 1.92 (s, 3H); High resolution mass spectrum (FAB) calculated (M+H$^+$) 641.2546, found 641.2569.

Example 1326g

3-[1-[3-(N-pyridin-2-ylamino)propyl]-3-(2-phenylethyl)-indazol-5-ylcarbonylamino]-2(S)-(2,4,6-trimethylbenzenesulfonylamino)propionic acid trifluoroacetate High resolution mass spectrum (FAB) calculated (M+H$^+$) 669.2859, found 669.2881.

Example 1327b

3-[1-[2-(N-Imidazol-2-ylaminocarbonyl)ethyl]indazol-5-ylcarbonylamino]-2(S)-(2,4,6-trimethylbenzenesulfonylamino)propionic acid trifluoroacetate $^1$H NMR (MeOH-d$_4$) δ8.11 (s, 1H), 8.09 (s, 1H), 7.77 (d, 1H), 7.68 (d, 1H), 7.10 (s, 2H), 6.73 (s, 2H), 4.81 (t, 2H), 4.14 (dd, 1H), 3.75 (dd, 1H), 3.47 (dd, 1H), 3.19 (t, 1H), 2.56 (s, 6H), 1.97 (s, 3H); high resolution mass spectrum (FAB) calculated (M+H$^+$) 568.1978, found 568.1972.

Example 2328

3-[1-[4-(N-4,5-Dihydroimidazol-2-ylamino)butyl]indazol-4-ylcarbonylamino]-2(S)-(benzyloxycarbonylamino)-propionic acid trifluoroacetate $^1$H NMR (DMSO-d$_6$) δ8.57 (m, 1H), 8.31 (s, 1H), 8.18 (bm, 1H), 7.86 (d, 1H), 7.63 (d, 1H), 7.50–7.35 (m, 3H), 7.30 (m, 5H), 5.00 (s, 2H), 4.43 (t, 2H), 4,28 (m, 1H), 3.75–3.40 (m, 6H), 3.07 (m, 2H), 1.78 (m, 2H), 1.38 (m, 2H); High resolution mass spectrum (FAB) calculated (M+H$^+$); 522.2465, found 522.2484.

Example 3093

3-[1-Methyl-3-[3-(N-imidazol-2-ylamino)propyl]indazol-6-ylcarbonylamino]-2(S)-(2,6-dimethylbenzenesulfonylamino)propionic acid trifluoroacetate $^1$H NMR (MeOH-d$_4$) δ7.90 (s, 1H), 7.76 (d, 1H), 7.47 (d, 1H), 7.09 (m, 1H), 7.01 (m, 2H), 6.81 (s, 2H), 4.16 (m, 1H), 4.04 (s, 3H), 3.78 (dd, 1H), 3.52 (dd, 1H), 3.34 (t, 2H), 3.09 (t, 2H), 2.62 (s, 6H), 2.14 (m, 2H); High resolution mass spectrum (FAB) calculated (M+H$^+$) 554.2186, found 554.2184.

Example 3142

3-[1-Methyl-3-[3-(N-pyridin-2-ylamino)propyl]indazol-6-ylcarbonylamino]-2(S)-(2,4,6-trimethylbenzenesulfonylamino)propionic acid trifluoroacetate $^1$H NMR (DMSO-d$_6$) δ8.52 (m, 2H), 8.08 (d, 1H), 7.95 (s, 1H), 7.90 (d, 1H), 7.82 (t, 1H), 7.77 (d, 1H), 7.46 (d, 1H), 6.97 (d, 1H), 6.79 (s+m, 3H), 4.05 (m, 1H), 4.01 (s, 3H), 3.59 (m, 2H), 3.39 (m, 2H), 3.03 (t, 2H), 2.52 (s, 6H), 2.07 (m, 2H), 2.00 (s, 3H); High resolution mass spectrum (FAB) calculated (M+H$^+$) 579.2390, found 579.2400.

Example 3339

3-[1-Benzyl-3-[3-(N-pyridin-2-ylamino)propyl]indazol-6-ylcarbonylamino]-2(S)-(2,4,6-trimethylbenzenesulfonylamino)propionic acid trifluoroacetate $^1$H NMR (DMSO-d$_6$) δ8.49 (t, 1H), 8.07 (d, 1H), 8.05 (s, 1H), 7.92 (d, 1H), 7.81 (d, 1H), 7.72 (m, 1H), 7.45 (d, 1H), 7.35–7.20 (m, 5H), 6.88 (d, 1H), 6.73 (s+m, 3H), 5.62 (s, 2H), 4.05 (m, 1H), 3.58 (m, 1H), 3.5–3.3 (m, 3H), 3.05 (t, 2H), 2.52 (s, 6H), 2.07 (m, 2H), 1.95 (s, 3H); High resolution mass spectrum (FAB) calculated (M+H$^+$) 655.2703, found 655.2701.

Scheme 16

Chemical Structures of the α$_v$β$_3$ Receptor Antagonist Zwitterion (SM256) and its Prodrugs (SM192 and SD209).

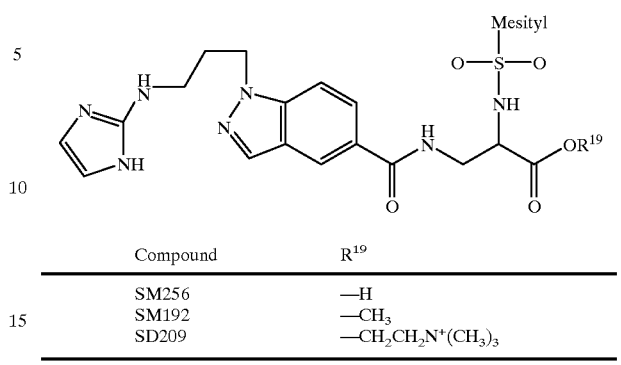

| Compound | R$^{19}$ |
|---|---|
| SM256 | —H |
| SM192 | —CH$_3$ |
| SD209 | —CH$_2$CH$_2$N$^+$(CH$_3$)$_3$ |

Example Ionto-1

To obtain a preliminary indication of the feasibility of transdermal iontophoretic delivery and the possible dependence on pH, the solution mobilities of the methyl and choline esters were evaluated using capillary electrophoresis. Free solution mobilities were determined using a capillary electrophoresis instrument equipped with a u.v. detector and a cationic amine capillary column of 57 cm total length, 50 cm length to detector, 370 μm o.d.,50 μm i.d. Buffers used were pH 4.5 acetate, pH 6.0 MES and pH 8.0 TRIS. All buffer concentrations were 50 mM. Elution was at 400 V/cm and 25° C., and detection was at 214 nm. Compounds SM192 and SD209 were examined. Structures are given in Scheme 16. For each compound, 2 mg/mL stock solutions were prepared and diluted 1:1 with the running buffer. Therefore, electrophoretic mobility of compound SD209 is about two-fold higher than that of compound SM192 at all pH values examined.

TABLE 1

Electrophoretic Mobility of Compounds SM192 and SD209 at Different pH Values
Electrophoretic Mobility (cm$^2$/v/sec) × 10$^{-4}$

| pH | SM192 | SD209 |
|---|---|---|
| 4.5 | 1.7 | 3.2 |
| 6.0 | 1.6 | 3.0 |
| 8.0 | 1.1 | 2.3 |

Example Ionto-2

In vitro permeation of prodrugs SM192 and SD209 was determined. The transdermal patch design used in these studies included a 2-compartment with ⅛" thick Porex® drug reservoir with a 2 cm$^2$ area of skin contact and a volume of 0.3 mL. The concentration of the drug solutions were ~100 mg/mL with the pH adjusted to ~4. The drug reservoir compartment was separated from the electrode compartment by a semipermeable membrane with a molecular cutoff of 100. The electrode compartment included a silver anion and a cation exchange media in a hydrogel matrix. The drug reservoir compartment was filled with dosing solution just before application to the skin.

The in vitro skin permeation of compound SM192 and SD209 was evaluated using a flow-through diffusion cell apparatus. A silver-silver chloride return cathode was located in the receiving compartment of the diffusion cells. Fresh excised dermatomed porcine skin, approximately 1 mm thick, was mounted onto the receiving compartment and the drug loaded patch was placed on top of the skin. Receiving solution was pH 7.4 buffered saline, and the flow through the receiving compartment was 0.25 mL/min. Iontophoresis current was applied using a constant current power supply. The flux vs. time profile with 24 hours of iontophoresis was determined. Concentrations of compound SM192 and SD209 were determined by HPLC. Steady-state flux values are listed in Table 2.

TABLE 2

Iontophoretic Flux for Compounds (2) and (3) through Pig Skin under Similar Conditions

| Compound | Flux ($\mu g/h/cm^2$) |
|---|---|
| SM192 | 2 |
| SD209 | 12 |

Example Ionto-3
Surface Tension Measurements

Surface activity behavior of the two prodrugs, SM192 and SD209 was examined using tensiometry. Stock solutions of each were prepared at a concentration of 0.06 M in water and dilutions were made using an aqueous solution of the corresponding salt counterion of the prodrug adjusted to a pH ~4. Surface tension measurements were run at 22° C. on a DuNouy tensiometer. Three measurements were run on each solution concentration. Data are provided in Table 3.

As can be seen from Table 3, SM192 showed a reduction in surface tension as a function of concentration and a distinct critical micelle concentration (CMC) of ~16 mM (~11 mg/mL) indicating formation of molecular aggregates at the concentration used in the in vitro skin iontophoretic experiment, but not in the electrophoresis experiment. The presence of a micellar phase will result in lower iontophoretic flux because the aggregates will have low permeability. SD209 on the other hand exhibited less reduction in surface tension as a function of concentration, and no critical micelle concentration was attained even at concentrations as high as 0.6 M.

TABLE 3

Surface Tension Measurements of Compounds SM192 and SD209 as a Function of Concentration

| | Surface Tension (dynes/cm) + SD | |
|---|---|---|
| Concentration (M) | Compound SM192 | Compound SD209 |
| 0.06 | 49.5 + 0.3 | 61.2 + 0.3 |
| 0.054 | 50.0 + 0.6 | 63.7 + 0.4 |
| 0.045 | 49.8 + 0.4 | 61.9 + 0.4 |
| 0.030 | 50.4 + 0.2 | 65.5 + 0.5 |
| 0.015 | 51.5 + 0.1 | 67.4 + 0.6 |
| 0.010 | 53.5 + 0.3 | 72.2 + 0.2 |
| 0.006 | 56.9 + 0.4 | |
| 0.003 | 61.7 + 0.2 | 72.4 + 0.06 |
| 0.0015 | 69.1 + 0.6 | 72.6 + 0.06 |
| 0.001 | 69.3 + 0.6 | |
| 0.0006 | 72.3 + 0.1 | |
| 0.0003 | 73.0 + 0.2 | |
| 0.00015 | 73.0 + 0.2 | |

Example Ionto-4
Partition Coefficient

The partition coefficient of SM192 and SD209 were estimated using an HPLC method, and data are listed in Table 4.

As can be seen from Table 4, SM192 has a higher log P value than SD209. This will result in less sequestering of SD209 by the skin tissue than that with SM192.

TABLE 4

Lipophilicity of SM192 and SD209 as Determined by HPLC Log P

| Compound | HPLC Log P |
|---|---|
| SM192 | 3.73 |
| SD209 | 0.95 |

Example Ionto-5

Data indicating conversion of the prodrug SD209 to the drug, SM256 once administered into circulation in vivo is represented in Table 5. The data in Table 5 id generated from intravenous administration of the prodrug, SD209, in pigs.

To show that SD209 converts in vivo to SM256, an i.v. study in two pigs was performed. SD209 was injected intravenously at a dose of 0.5 mg/kg and plasma was seperated after blood sampling at different intervals. Following solid phase extraction of the plasma, residues were chromatographed on a supelcosil ABZ HPLC column and detected by positive ion electrospray MS/MS using a Sciex API 300. This combination provides a specific assay for both SD209 and SM256. The linear range of the assay for SM256 was from 1 ng/ml to 2000 ng/ml. Plasma concentration data for both pigs are provided below

TABLE 5

Plasma concentrations of SD209 and SM256 in Yorkshire domestic swine following i.v. bolus administration (0.5 mg/kg) of SD209.

| | pig 1 plasma conc. (ng/ml) | | pig 2 plasma conc. (ng/ml) | |
|---|---|---|---|---|
| Time (hr) | SM256 | SD209 | SM256 | SD209 |
| 0.00 | 3.4 | <2 | 8.3 | <2 |
| 0.1 | 123.5 | 60 | 276.7 | 20 |
| 0.25 | 68.7 | 20 | 68.5 | 3 |
| 0.5 | — | — | 20.9 | <2 |
| 1.0 | 5.2 | BQL | 6.8 | BQL |
| 2.0 | — | — | 2.3 | BQL |
| 3.0 | 1.3 | BQL | 1.5 | BQL |
| 5.0 | 1.0 | BQL | 1.7 | BQL |
| 7.0 | 2.1 | BQL | BQL | BQL |
| 10.0 | BQL | BQL | BQL | BQL |
| 14.0 | BQL | BQL | BQL | BQL |
| 24.0 | BQL | BQL | BQL | BQL |

This data would indicate that SD209 is quantitatively converted to SM256 once it is in the circulation after iontophoretic delivery.

Utility

The compounds of Formula Ia, Ib, Ic, Id or Ie of the present invention possess activity, upon metabolism of the prodrug moiety, as antagonists of integrins such as, for example, the $\alpha_v\beta_3$ or vitronectin receptor, $\alpha_v\beta_5$ or $\alpha_5\beta_1$, and as such have utility in the treatment and diagnosis of cell adhesion, angiogenic disorders, inflammation, bone degradation, cancer metastases, diabetic retinopathy, thrombosis, restenosis, macular degeneration, and other conditions mediated by cell adhesion and/or cell migration and/or angiogenesis. The integrin antagonist activity of the compounds of the present invention is demonstrated using assays which measure the binding of a specific integrin to a native ligand, for example, using the ELISA assay described below for the binding of vitronectin to the $\alpha_v\beta_3$ receptor.

The compounds of the present invention possess selectivity for the $\alpha_v\beta_3$ receptor relative to the GPIIb/IIIa receptor as demonstrated by their reduced activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The compounds of Formula Ia, Ib, Ic, Id or Ie of the present invention may be useful for the treatment or prevention of other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The compounds of Formula Ia, Ib, Ic, Id or Ie have the ability to suppress/inhibit angiogenesis in vivo, for example, as demonstrated using animal models of ocular neovascularization.

The compounds provided by this invention are also useful as standards and reagents in determining the ability of a potential pharmaceutical to inhibit integrin-ligand binding. These may be provided in a commercial kit comprising a compound of this invention.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta)—Vitronectin ELISA, $\alpha_v\beta_3$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an $IC_{50}$ or $K_i$ value of less than about 10 $\mu$M for the inhibition of $\alpha_v\beta_3$-Vitronectin Binding Assay, with compounds preferably having $K_i$ values of less than about 0.1 $\mu$M. Tested compounds of the present invention are active in the $\alpha_v\beta_3$-Vitronectin Binding Assay.

Purified $\alpha_v\beta_3$ (Human Placenta)—Vitronectin ELISA

The $\alpha_v\beta_3$ receptor was isolated from human placental extracts prepared using octylglucoside. The extracts were passed over an affinity column composed of anti-$\alpha_v\beta_3$ monoclonal antibody (LM609) bound to Affigel. The column was subsequently washed extensively at pH 7 and pH 4.5 followed by elution at pH 3. The resulting sample was concentrated by wheat germ agglutinin chromatography to provide two bands by SDS gel electrophoresis which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel and according to effects of blocking antibodies for the $\alpha_v\beta_3$ or $\alpha_v\beta_5$ integrins in the ELISA.

A submaximal concentration of biotinylated vitronectin was selected based on a concentration response curve with fixed receptor concentration and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM $CaCl_2$, 1.0 mM $MgCl_2 \cdot 6H_2O$, 1.0 mM $MnCl_2 \cdot 4H_2O$) and coated (100 $\mu$L/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM $CaCl_2$, 1.0 mM $MgCl_2 \cdot 6H_2O$, 1.0 mM $MnCl_2 \cdot 4H_2O$). Receptor is then blocked (200 $\mu$L/well) with 3.5% BSA in B/B buffer for 2 hours at room temperature. After washing once with 1.0% BSA in B/B buffer, biotinylated vitronectin (100 $\mu$L) and either inhibitor (11 $\mu$L) or B/B buffer w/1.0% BSA (11 $\mu$L) is added to each well. The plates are incubated 2 hours at room temperature. The plates are washed twice with B/B buffer and incubated 1 hour at room temperature with anti-biotin alkaline phosphatase (100 $\mu$L/well) in B/B buffer containing 1.0% BSA. The plates are washed twice with B/B buffer and alkaline phosphatase substrate (100 $\mu$L) is added. Color is developed at room temperature. Color development is stopped by addition of 2N NaOH (25 $\mu$L/well) and absorbance is read at 405 nm. The $IC_{50}$ is the concentration of test substance needed to block 50% of the vitronectin binding to the receptor.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Test compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_v\beta_5$ and $\alpha_5\beta_1$ integrin interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 $\mu$L of PRP ($5 \times 10^8$ platelets/mL) were added to each micro test tube, and transmittance was set to 0%. 20 $\mu$L of ADP (10 $\mu$M) was added to each tube, and the aggregation profiles were plotted (% transmittance versus time). Test agent (20 $\mu$L) was added at different concentrations prior to the addition of the platelet agonist. Results are expressed as % inhibition of agonist-induced platelet aggregation.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., *J. Clin. Invest.* (1995) 95: 713–724).

In Vivo Angiogenesis Model

A quantitative method for assessing angiogenesis and antiangiogenic agents is described in Passaniti et al., *Laboratory Investigation* (1992) 67: 519–528

Pig Restenosis Model

A method for assessing restenosis and agents which inhibit restenosis is described in Schwartz et al., *J. Am. College of Cardiology* (1992) 19: 267–274.

Mouse Retinopathy Model

A method for assessing retinopathy and agents which inhibit retinopathy is described in Smith et al., *Invest. Ophthal. & Visual Science* (1994) 35: 101–111.

Dosage and Formulation

The compounds of this invention can be administered by any means that produces contact of the active agent with the agent's site of action, the $\alpha_v\beta_3$ integrin, in the body of a mammal. They can be administered by any conventional means available for use in conjunction with pharmaceuticals, either as individual therapeutic agents or in a combination of therapeutic agents, such as a antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered by injection, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The combination products of this invention, such as the novel $\alpha_v\beta_3$ antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the $\alpha_v\beta_3$ antagonist compounds of this invention and the anti-coagulant agent, anti-platelet agent, thrombin inhibitor, and/or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the $\alpha_v\beta_3$ antagonist compounds of this invention and the anti-coagulant agent, anti-platelet agent, thrombin inhibitor, and/or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of thrombus formation, the prevention of blood clots, and/or the treatment of thromboembolic disorders, which comprise a therapeutically effective amount of a compound according to the method of the present invention along with a therapeutically effective amount of an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compounds according to the method of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

What is claimed is:

1. A compound of Formula Ia:

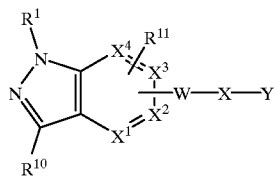

including stereoisomeric forms thereof, or mixtures of stereoisomeric forms thereof, or pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

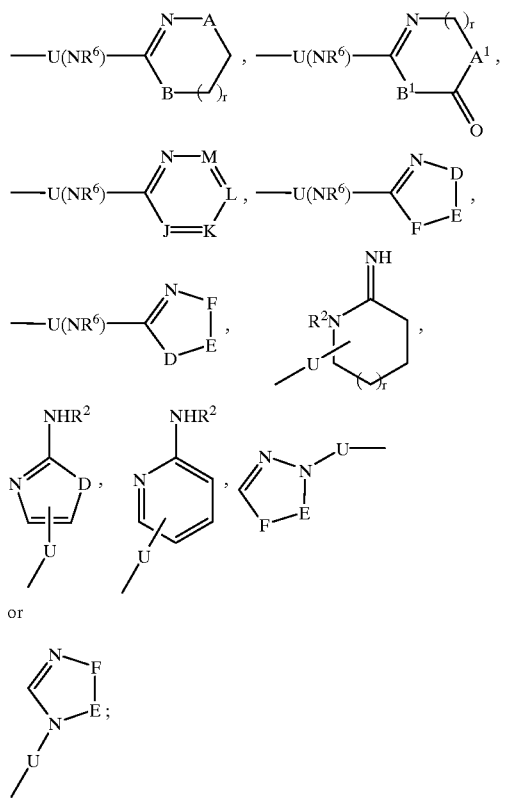

A and B are independently —$CH_2$—, —O—, —N($R^2$)—, or —C(=O)—;

$A^1$ and $B^1$ are independently —$CH_2$— or —N($R^3$)—;

D is —N($R^2$)—, —O—, —S—, —C(=O)— or —$SO_2$—;

E—F is —C($R^4$)=C($R^5$)—, —N=C($R^4$)—, —C($R^4$)=N—, or —C($R^4$)$_2$C($R^5$)$_2$—;

J, K, L and M are independently selected from —C($R^4$)—, —C($R^5$)— or —N—, provided that at least one of J, K, L and M is not —N—;

$R^2$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl—, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7=CR^8)(CH_2)_m$—,
—$(CH_2)_n(C\equiv C)(CH_2)_m$—,
—$(CH_2)_rQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—,
—$(CH_2)_n(C=O)N(R^6)(CH_2)_m$—
—$(CH_2)_nN(R^6)(C=O)(CH_2)_m$—, or
—$(CH_2)_nS(O)_p(CH_2)_m$—;
wherein one or more of the methylene groups in U is optionally substituted with $R^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^{10}$ is selected from: H, $N(R^6)_2$, halogen, $NO_2$, CN, $CF_3$, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_1$–$C_4$ alkoxy substituted with 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from:
—$(C(R^{12})_2)_qC(=O)N(R^{13})$—, or
—$C(=O)$—$N(R^{13})$—$(C(R^{12})_2)_q$—;

X is —C(R$^{12}$)(R$^{14}$)—C(R$^{12}$)(R$^{15}$)—;

R$^{12}$ is selected from H, halogen, C$_1$–C$_6$ alkyl, C$_2$–C$_6$ alkenyl, C$_2$–C$_6$ alkynyl, C$_3$–C$_7$ cycloalkyl, C$_4$–C$_{10}$ cycloalkylalkyl, (C$_1$–C$_4$ alkyl)carbonyl, aryl, or aryl (C$_1$–C$_6$ alkyl)-;

R$^{13}$ is selected from H, C$_1$–C$_6$ alkyl, C$_3$–C$_7$ cycloalkylmethyl, or aryl(C$_1$–C$_6$ alkyl)-;

R$^{14}$ is selected from: H, C$_1$–C$_6$ alkylthio(C$_1$–C$_6$ alkyl)-, aryl(C$_1$–C$_{10}$ alkylthioalkyl)-, aryl(C$_1$–C$_{10}$ alkoxyalkyl)-, C$_1$–C$_{10}$ alkyl, C$_1$–C$_{10}$ alkoxyalkyl, C$_1$–C$_6$ hydroxyalkyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl (C$_1$–C$_6$ alkyl)-, heteroaryl(C$_1$–C$_6$ alkyl)-, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be unsubstituted or substituted independently with 0–1 R$^{16}$ or 0–2 R$^{11}$;

R$^{15}$ is selected from: H, R$^{16}$, C$_1$–C$_{10}$ alkyl, C$_1$–C$_{10}$ alkoxyalkyl, C$_1$–C$_{10}$ alkylaminoalkyl, C$_1$–C$_{10}$ dialkylaminoalkyl, (C$_1$–C$_{10}$ alkyl)carbonyl, aryl (C$_0$–C$_6$ alkyl)carbonyl, C$_1$–C$_{10}$ alkenyl, C$_1$–C$_{10}$ alkynyl, C$_3$–C$_{10}$ cycloalkyl, C$_3$–C$_{10}$ cycloalkylalkyl, aryl(C$_1$–C$_6$ alkyl)-, heteroaryl(C$_1$–C$_6$ alkyl)-, aryl, heteroaryl, CO$_2$R$^{17}$, C(=O)R$^{17}$, CONR$^{17}$R$^{20}$, SO$_2$R$^{17}$, or SO$_2$NR$^{17}$R$^{20}$, provided that any of the above alkyl, cycloalkyl, aryl or heteroaryl groups may be unsubstituted or substituted independently with 0–2 R$^{11}$;

Y is —COR$^{19}$;

R$^{16}$ is selected from:
—N(R$^{20}$)—C(=O)—O—R$^{17}$,
—N(R$^{20}$)—C(=O)—R$^{17}$,
—N(R$^{20}$)—C(=O)—NH—R$^{17}$,
—N(R$^{20}$)SO$_2$—R$^{17}$, or
—N(R$^{20}$)SO$_2$—NR$^{20}$R$^{17}$;

R$^{17}$ is selected from: C$_1$–C$_{10}$ alkyl, C$_3$–C$_{11}$ cycloalkyl, aryl(C$_1$–C$_6$ alkyl)-, (C$_1$–C$_6$ alkyl)aryl, heteroaryl (C$_1$–C$_6$ alkyl)-, (C$_1$–C$_6$ alkyl)heteroaryl, biaryl(C$_1$–C$_6$ alkyl)-, heteroaryl, or aryl, wherein said aryl or heteroaryl groups are optionally substituted with 0–3 substituents selected from the group consisting of: C$_1$–C$_4$ alkyl, C$_1$–C$_4$ alkoxy, aryl, heteroaryl, halo, cyano, amino, CF$_3$, and NO$_2$;

R$^{19}$ is —O—(CH$_2$)$_k$N$^+$(R$^{22}$)(R$^{23}$)(R$^{24}$)Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{22}$, R$^{23}$ and R$^{24}$ are independently selected from: H, C$_1$–C$_9$ alkyl, C$_4$–C$_{11}$ cycloalkylalkyl, aryl, aryl(C$_1$–C$_6$ alkyl), heteroaryl, heteroaryl(C$_1$–C$_6$ alkyl) wherein said alkyl or aryl groups are substituted with 0–2 substituents selected from the group consisting of C$_1$–C$_4$ alkyl, C$_1$–C$_4$ alkoxy, OH, halo, CF$_3$, and nitro;

alternatively R$^{22}$ and R$^{23}$ can be taken together to form a 5–7 membered heterocyclic aromatic or non-aromatic ring system containing 1–3 heteroatoms selected from N, O and S and R$^{24}$ is defined as above or R$^{22}$, R$^{23}$, and R$^{24}$ can be taken together to form a heterobicyclic ring system containing 1–3 heteroatoms selected from N, O and S, wherein said heterocyclic or heterobicyclic ring being optionally substituted with 0–2 groups selected from C$_1$–C$_4$ alkyl, C$_1$–C$_4$ alkoxy, halo, cyano, amino, CF$_3$, and NO$_2$;

R$^{20}$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_1$–C$_6$ alkyl)-;

R$^{21}$ is selected from: COOH or NR$^6{}_2$;

k is 2, 3, 4, 5, or 6;
m is 0, 1, 2, 3, or 4;
n is 0, 1, 2, 3, or 4;
t is 0, 1, 2, 3, or 4;
p is 0, 1, or 2;
q is 0, 1, or 2; and
r is 0, 1, or 2;

with the following provisos:
(1) t, n, m and q are chosen such that the number of atoms connecting R$^1$ and Y is in the range of 10–14; and
(2) n and m are chosen such that the value of n plus m is greater than one unless U is —(CH$_2$)$_t$Q(CH$_2$)$_m$—.

2. A compound of claim 1 of the Formula Ia:

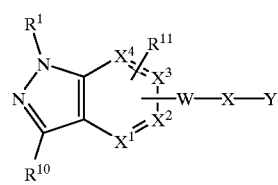

Ia including stereoisomeric forms thereof, or mixtures of stereoisomeric forms thereof, or pharmaceutically acceptable salt forms thereof, wherein:

X$^1$, X$^2$, X$^3$, and X$^4$ are independently selected from nitrogen or carbon provided that at least two of X$^1$, X$^2$, X$^3$ and X$^4$ are carbon;

R$^1$ is selected from:

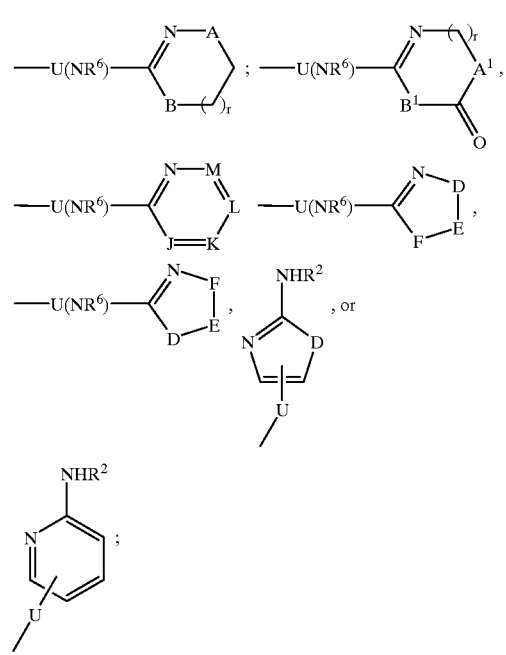

A and B are independently —CH$_2$—, —O—, —N(R$^2$)—, or —C(=O)—;
A$^1$ and B$^1$ are independently —CH$_2$— or —N(R$^3$)—;
D is —N(R$^2$)—, —O—, —S—, —C(=O)— or —SO$_2$—;
E—F is —C(R$^4$)=C(R$^5$)—, —N=C(R$^4$)—, —C(R$^4$)=N—, or —C(R$^4$)$_2$C(R$^5$)$_2$—;
J, K, L and M are independently selected from —C(R$^4$)—, —C(R$^5$)— or —N—, provided that at least one of J, K, L and M is not —N—;

R$^2$ is selected from: H, $C_1$–$C_6$ alkyl, ($C_1$–$C_6$ alkyl)carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylalkyl, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

R$^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

R$^4$ and R$^5$ are independently selected from: H, $C_1$–$C_4$ alkoxy, NR$^2$R$^3$, halogen, NO$_2$, CN, CF$_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, arylcarbonyl or alternatively, when substituents on adjacent atoms, R$^4$ and R$^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, CF$_3$, or NO$_2$;

U is selected from:
—(CH$_2$)$_n$—,
—(CH$_2$)$_n$(CR$^7$=CR$^8$)(CH$_2$)$_m$—,
—(CH$_2$)$_t$Q(CH$_2$)$_m$—,
—(CH$_2$)$_n$O(CH$_2$)$_m$—,
—(CH$_2$)$_n$N(R$^6$)(CH$_2$)$_m$—,
—(CH$_2$)$_n$C(=O)(CH$_2$)$_m$—, or
—(CH$_2$)$_n$S(O)$_p$(CH$_2$)$_m$—;
wherein one or more of the methylene groups in U is optionally substituted with R$^7$;

Q is selected from 1,2-phenylene, 1,3-phenylene, 2,3-pyridinylene, 3,4-pyridinylene, or 2,4-pyridinylene;

R$^6$ is selected from: H, $C_1$–$C_4$ alkyl, or benzyl;

R$^7$ and R$^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

R$^{10}$ is selected from: H, N(R$^6$)$_2$, halogen, NO$_2$, CN, CF$_3$, CO$_2$R$^{17}$, C(=O)R$^{17}$, CONR$^{17}$R$^{20}$, —SO$_2$R$^{17}$, —SO$_2$NR$^{17}$R$^{20}$, $C_1$–$C_6$ alkyl substituted with 0–1 R$^{15}$ or 0–1 R$^{21}$, $C_1$–$C_4$ alkoxy substituted with 0–1 R$^{21}$, $C_3$–$C_6$ alkenyl substituted with 0–1 R$^{15}$ or 0–1 R$^{21}$, $C_3$–$C_7$ cycloalkyl substituted with 0–1 R$^{15}$ or 0–1 R$^{21}$, $C_4$–$C_{11}$ cycloalkylalkyl substituted with 0–1 R$^{15}$ or 0–1 R$^{21}$, aryl substituted with 0–1 R$^{15}$ or 0–2 R$^{11}$ or 0–1 R$^{21}$, or aryl($C_1$–$C_6$ alkyl)- substituted with 0–1 R$^{15}$ or 0–2 R$^{11}$ or 0–1 R$^{21}$;

R$^{11}$ is selected from: H, halogen, CF$_3$, CN, NO$_2$, hydroxy, NR$^2$R$^3$, $C_1$–$C_4$ alkyl substituted with 0–1 R$^{21}$, $C_1$–$C_4$ alkoxy substituted with 0–1 R$^{21}$, aryl substituted with 0–1 R$^{21}$, aryl($C_1$–$C_6$ alkyl)- substituted with 0–1 R$^{21}$, ($C_1$–$C_4$ alkoxy)carbonyl substituted with 0–1 R$^{21}$, ($C_1$–$C_4$ alkyl)carbonyl substituted with 0–1 R$^{21}$, $C_1$–$C_4$ alkylsulfonyl substituted with 0–1 R$^{21}$, or $C_1$–$C_4$ alkylaminosulfonyl substituted with 0–1 R$^{21}$;

W is —C(=O)—N(R$^{13}$)—(C(R$^{12}$)$_2$)$_q$—;

X is —C(R$^{12}$)(R$^{14}$)—C(R$^{12}$)(R$^{15}$)—;

R$^{12}$ is H or $C_1$–$C_6$ alkyl;

R$^{13}$ is selected from: H, $C_1$–$C_6$ alkyl, $C_3$–$C_7$ cycloalkylmethyl, or aryl($C_1$–$C_6$ alkyl)-;

R$^{14}$ is selected from: H, $C_1$–$C_6$ alkylthioalkyl, aryl ($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be substituted independently with 0–1 R$^{16}$ or 0–2 R$^{11}$;

R$^{15}$ is selected from: H, R$^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, CO$_2$R$^{17}$, C(=O)R$^{17}$, CONR$^{17}$R$^{20}$, SO$_2$R$^{17}$, or SO$_2$NR$^{17}$R$^{20}$, provided that any of the above alkyl, cycloalkyl, aryl or heteroaryl groups may be substituted independently with 0–2 R$^{11}$;

Y is —COR$^{19}$;

R$^{16}$ is selected from:
—N(R$^{20}$)—C(=O)—O—R$^{17}$,
—N(R$^{20}$)—C(=O)—R$^{17}$,
—N(R$^{20}$)—C(=O)—NH—R$^{17}$,
—N(R$^{20}$)SO$_2$—R$^{17}$, or
—N(R$^{20}$)SO$_2$—NR$^{20}$R$^{17}$;

R$^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, CF$_3$, and NO$_2$;

R$^{19}$ is —O—(CH$_2$)$_k$N$^+$(R$^{22}$)(R$^{23}$)(R$^{24}$)Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{22}$, R$^{23}$ and R$^{24}$ are independently selected from: H, $C_1$–$C_6$ alkyl, $C_4$–$C_{11}$ cycloalkylalkyl, aryl, aryl($C_1$–$C_6$ alkyl), heteroaryl, heteroaryl($C_1$–$C_6$ alkyl) wherein said alkyl or aryl groups are substituted with 0–2 substituents selected from the group consisting of $C_1$–$C_4$ alkyl, $C_1$–$C_4$ alkoxy, OH, halo, CF$_3$, and nitro;

alternatively R$^{22}$ and R$^{23}$ can be taken together to form a 5–7 membered heterocyclic aromatic or non-aromatic ring system containing 1–3 heteroatoms selected from N, O and S and R$^{24}$ is defined as above or R$^{22}$, R$^{23}$, and R$^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, CF$_3$, and NO$_2$;

R$^{20}$ selected from: H, $C_1$–$C_6$ alkyl, $C_3$–$C_7$ cycloalkyl, $C_4$–$C_{11}$ cycloalkylalkyl, aryl($C_1$–$C_6$ alkyl)-, or heteroaryl($C_1$–$C_6$ alkyl)-;

R$^{21}$ is selected from COOH or NR$^6{}_2$;

k is 2–4;

m is 0–4;

n is 0–4;
p is 0–2;
q is 0–2;
t is 0–4; and
r is 0–2.

3. A compound of claim 1 of the Formula IIa or IIb:

IIa

IIb including stereoisomeric forms thereof, or mixtures of stereoisomeric forms thereof, or pharmaceutically acceptable salt forms thereof wherein:

$X_1$ and $X_3$ are independently selected from nitrogen or carbon;

$R^1$ is selected from:

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_qQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, halogen, $CO_2R^{17}$, $CONR^{17}R^{20}$, $C_1$–$C_6$ alkyl substituted with 0–1 $R^{15}$ or 0–1 $R^{21}$, $C_1$–$C_4$ alkoxy substituted with 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—N($R^{20}$)$R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, $C_1$–$C_4$ alkyl, and $C_4$–$C_{11}$ cycloalkylalkyl;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{20}$ is H or $CH_3$;

$R^{21}$ is selected from COOH or $NR^6_2$;

k is 2;

m is 0 or 1;

n is 1–4; and t is 0 or 1.

4. A compound of claim 1 of the Formula IIa or IIb:

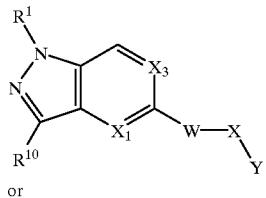

IIa or

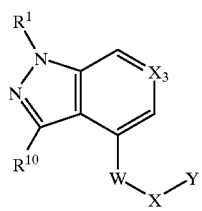

IIb including stereoisomeric forms thereof, or mixtures of stereoisomeric forms thereof, or pharmaceutically acceptable salt forms thereof wherein:

$X_1$ and $X_3$ are independently selected from nitrogen or carbon, provided that at least one of $X_1$ and $X_3$ is carbon;

$R^1$ is selected from:

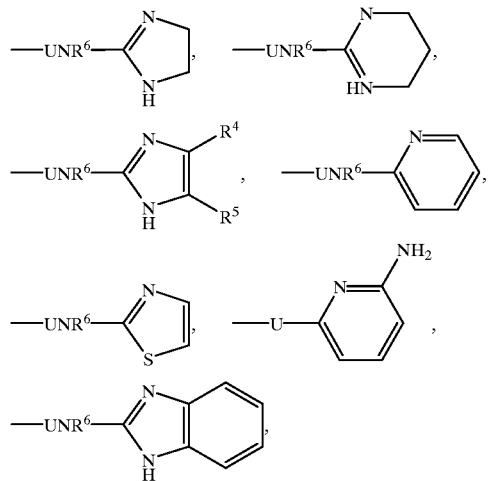

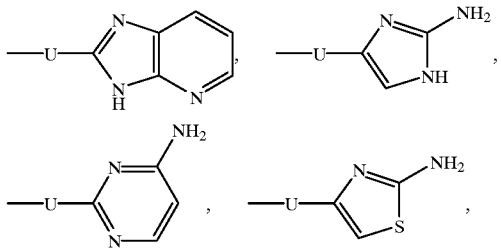

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_t Q(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, halogen, $CO_2R^{17}$, $CONR^{17}R^{20}$, $C_1$–$C_6$ alkyl substituted with 0–1 $R^{15}$ or 0–1 $R^{21}$, $C_1$–$C_4$ alkoxy substituted with 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—N($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—(CH$_2$)$_k$N$^+$(R$^{22}$)(R$^{23}$)(R$^{24}$)Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from: H, methyl, ethyl, propyl and butyl;

alternatively $R^{22}$ and $R^{23}$ can be taken together to form a 5–7 membered heterocyclic ring system containing 1–2 heteroatoms selected from N, O and S and $R^{24}$ is defined as above;

$R^{20}$ is H or CH$_3$;

$R^{21}$ is selected from COOH or NR$^6_2$;

k is 2;

m is 0 or 1;

n is 1–4; and t is 0 or 1.

5. An ammonium ester compound of claim 1 of Formula Ia, including enantiomeric forms, diasteriomeric forms or mixtures of enantiomeric or diasteriomeric forms thereof, and pharmaceutically acceptable salt forms thereof, wherein:

the alkyl ammonium component in the ester group of $R^{19}$ is selected from:

(trimethylammonium)ethyl,
(triethylammonium)ethyl,
(diethylmethylammonium)ethyl,
(1-morpholinomethylammonium)ethyl,
(1-morpholinoethylammonium)ethyl,
(1-pyrrolidinomethylammonium)ethyl, and
(1-pyrrolidinoethylammonium)ethyl; and the acid component of the compound is selected from:

3-[1-[3-(imidazolin-2-ylamino)propyl]indazol-5-ylcarbonylamino]-2-(benzyloxycarbonylamino)-propionic acid, 3-[1-[3-(imidazolin-2-ylamino)propyl]indazol-5-ylcarbonylamino]-2-(2,4,6-trimethylbenzene-sulfonylamino)propionic acid, 3-[1-[3-(imidazolin-2-ylamino)propyl]indazol-5-ylcarbonylamino]-2-(benzenesulfonylamino)propionic acid, 3-[1-[3-(imidazolin-2-ylamino)propyl]indazol-5-ylcarbonylamino]-2-(2,6-dichlorobenzene-sulfonylamino)propionic acid, 3-[1-[3-(imidazolin-2-ylamino)propyl]indazol-5-ylcarbonylamino]-2-(3,5-dimethylisoxazol-4-ylsulfonylamino) propionic acid, 3-[1-[3-(imidazolin-2-ylamino)propyl]indazol-5-ylcarbonylamino]-2-(2,6-dimethylbenzene-sulfonylamino)propionic acid, 3-[1-[3-(imidazolin-2-ylamino)propyl]indazol-5-ylcarbonylamino]-2-(2,6-dimethyl-4-phenyl-benzenesulfonylamino)propionic acid, 3-[1-[3-(imidazolin-2-ylamino)propyl]indazol-5-ylcarbonylamino]-2-(4-phenylbenzenesulfonyl-amino)propionic acid, 3-[1-[3-(tetrahydropyrimid-2-ylamino)propyl]-indazol-5-ylcarbonylamino]-2-(benzyloxy-carbonylamino) propionic acid, 3-[1-[3-(tetrahydropyrimid-2-ylamino)propyl]-indazol-5-ylcarbonylamino]-2-(2,4,6-trimethylbenzenesulfonylamino)propionic acid, 3-[1-[3-(tetrahydropyrimid-2-ylamino)propyl]-indazol-5-ylcarbonylamino]-2-(benzenesulfonyl-amino)propionic acid, 3-[1-[3-(tetrahydropyrimid-2-ylamino)propyl]-indazol-5-ylcarbonylamino]-2-(2,6-dichloro-benzenesulfonylamino)propionic acid, 3-[1-[3-(tetrahydropyrimid-2-ylamino)propyl]-indazol-5-ylcarbonylamino]-2-(3,5-dimethyl-isoxazol-4-ylsulfonylamino)propionic acid, 3-[1-[3-(tetrahydropyrimid-2-ylamino)propyl]-indazol-5-ylcarbonylamino]-2-(2,6-dimethyl-benzenesulfonylamino)propionic acid, 3-[1-[3-(tetrahydropyrimid-2-ylamino)propyl]-indazol-5-ylcarbonylamino]-2-(2,6-dimethyl-4-phenylbenzenesulfonylamino)propionic acid, 3-[1-[3-(tetrahydropyrimid-2-ylamino)propyl]-indazol-5-ylcarbonylamino]-2-(4-phenylbenzene-sulfonylamino) propionic acid, 3-[1-[3-(imidazol-2-ylamino)propyl]indazol-5-yl-carbonylamino]-2-(benzyloxycarbonylamino)-propionic acid, 3-[1-[3-(imidazol-2-ylamino)propyl]indazol-5-yl-carbonylamino]-2-(2,4,6-trimethylbenzene-sulfonylamino)propionic acid, 3-[1-[3-(imidazol-2-ylamino)propyl]indazol-5-yl-carbonyl amino]-2-(benzenesulfonylamino)-propionic acid, 3-[1-[3-(imidazol-2-ylamino)propyl]indazol-5-yl-carbonylamino]-2-(2,6-dichlorobenzene-sulfonylamino) propionic acid, 3-[1-[3-(imidazol-2-ylamino)propyl]indazol-5-yl-carbonylamino]-2-(3,5-dimethylisoxazol-4-ylsulfonylamino)propionic acid, 3-[1-[3-(imidazol-2-ylamino)propyl]indazol-5-yl-carbonylamino]-2-(2,6-dimethylbenzene-sulfonylamino) propionic acid, 3-[1-[3-(imidazol-2-ylamino)propyl]indazol-5-yl-carbonylamino]-2-(2,6-dimethyl-4-phenyl-benzenesulfonylamino)propionic acid, 3-[1-[3-(imidazol-2-ylamino)propyl]indazol-5-yl-carbonylamino]-2-(4-phenylbenzenesulfonyl-amino) propionic acid, 3-[1-[3-(pyridin-2-ylamino)propyl]indazol-5-yl-carbonylamino]-2-(benzyloxycarbonylamino)-propionic acid, 3-[1-[3-(pyridin-2-ylamino)propyl]indazol-5-yl-carbonylamino]-2-(2,4,6-trimethylbenzene-sulfonylamino)propionic acid, 3-[1-[3-(pyridin-2-ylamino)propyl]indazol-5-yl-carbonylamino]-2-(benzenesulfonylamino)-propionic acid, 3-[1-[3-(pyridin-2-ylamino)propyl]indazol-5-yl-carbonylamino]-2-(2,6-dichlorobenzene-sulfonylamino) propionic acid, 3-[1-[3-(pyridin-2-ylamino)propyl]indazol-5-yl-carbonylamino]-2-(3,5-dimethylisoxazol-4-ylsulfonylamino)propionic acid, 3-[1-[3-(pyridin-2-ylamino)propyl]indazol-5-yl-carbonylamino]-2-(2,6-dimethylbenzene-sulfonylamino) propionic acid, 3-[1-[3-(pyridin-2-ylamino)propyl]indazol-5-yl-carbonylamino]-2-(2,6-dimethyl-4-phenyl-benzenesulfonylamino)propionic acid, 3-[1-[3-(pyridin-2-ylamino)propyl]indazol-5-yl-carbonylamino]-2-(4-phenylbenzenesulfonyl-amino) propionic acid, 3-[1-[3-(imidazolin-2-ylamino)propyl]indazol-4-ylcarbonylamino]-2-(benzyloxycarbonylamino)-propionic acid, 3-[1-[3-(imidazolin-2-ylamino)propyl]indazol-4-ylcarbonylamino]-2-(2,4,6-trimethylbenzene-sulfonylamino)propionic acid, 3-[1-[3-(imidazolin-2-ylamino)propyl]indazol-4-ylcarbonylamino]-2-(benzenesulfonylamino)propionic acid,
3-[1-[3-(imidazolin-2-ylamino)propyl]indazol-4-ylcarbonylamino]-2-(2,6-dichlorobenzene-sulfonylamino)propionic acid,
3-[1-[3-(imidazolin-2-ylamino)propyl]indazol-4-ylcarbonylamino]-2-(3,5-dimethylisoxazol-4-ylsulfonylamino) propionic acid,
3-[1-[3-(imidazolin-2-ylamino)propyl]indazol-4-ylcarbonylamino]-2-(2,6-dimethylbenzene-sulfonylamino)propionic acid,
3-[1-[3-(imidazolin-2-ylamino)propyl]indazol-4-ylcarbonylamino]-2-(2,6-dimethyl-4-phenyl-benzenesulfonylamino)propionic acid,
3-[1-[3-(imidazolin-2-ylamino)propyl]indazol-4-ylcarbonylamino]-2-(4-phenylbenzenesulfonyl-amino)propionic acid,
3-[1-[3-(tetrahydropyrimid-2-ylamino)propyl]-indazol-4-ylcarbonylamino]-2-(benzyloxy-carbonylamino)propionic acid,
3-[1-[3-(tetrahydropyrimid-2-ylamino)propyl]-indazol-4-ylcarbonylamino]-2-(2,4,6-trimethyl-benzenesulfonylamino)propionic acid,
3-[1-[3-(tetrahydropyrimid-2-ylamino)propyl]-indazol-4-ylcarbonylamino]-2-(benzenesulfonyl-amino)propionic acid,
3-[1-[3-(tetrahydropyrimid-2-ylamino)propyl]-indazol-4-ylcarbonylamino]-2-(2,6-dichloro-benzenesulfonylamino)propionic acid,
3-[1-[3-(tetrahydropyrimid-2-ylamino)propyl]-indazol-4-ylcarbonylamino]-2-(3,5-dimethyl-isoxazol-4-ylsulfonylamino)propionic acid,
3-[1-[3-(tetrahydropyrimid-2-ylamino)propyl]-indazol-4-ylcarbonylamino]-2-(2,6-dimethyl-benzenesulfonylamino)propionic acid,
3-[1-[3-(tetrahydropyrimid-2-ylamino)propyl]-indazol-4-ylcarbonylamino]-2-(2,6-dimethyl-4-phenylbenzenesulfonylamino)propionic acid,
3-[1-[3-(tetrahydropyrimid-2-ylamino)propyl]-indazol-4-ylcarbonylamino]-2-(4-phenylbenzene-sulfonylamino)propionic acid,
3-[1-[3-(imidazol-2-ylamino)propyl]indazol-4-yl-carbonylamino]-2-(benzyloxycarbonylamino)-propionic acid,
3-[1-[3-(imidazol-2-ylamino)propyl]indazol-4-yl-carbonylamino]-2-(2,4,6-trimethylbenzene-sulfonylamino)propionic acid,
3-[1-[3-(imidazol-2-ylamino)propyl]indazol-4-yl-carbonylamino]-2-(benzenesulfonylamino)-propionic acid,
3-[1-[3-(imidazol-2-ylamino)propyl]indazol-4-yl-carbonylamino]-2-(2,6-dichlorobenzene-sulfonylamino) propionic acid,
3-[1-[3-(imidazol-2-ylamino)propyl]indazol-4-yl-carbonyl amino]-2-(3,5-dimethylisoxazol-4-ylsulfonylamino) propionic acid,
3-[1-[3-(imidazol-2-ylamino)propyl]indazol-4-yl-carbonylamino]-2-(2,6-dimethylbenzene-sulfonylamino) propionic acid,
3-[1-[3-(imidazol-2-ylamino)propyl]indazol-4-yl-carbonylamino]-2-(2,6-dimethyl-4-phenyl-benzenesulfonylamino)propionic acid,
3-[1-[3-(imidazol-2-ylamino)propyl]indazol-4-yl-carbonylamino]-2-(4-phenylbenzenesulfonyl-amino) propionic acid,
3-[1-[3-(pyridin-2-ylamino)propyl]indazol-4-yl-carbonylamino]-2-(benzyloxycarbonylamino)-propionic acid,
3-[1-[3-(pyridin-2-ylamino)propyl]indazol-4-yl-carbonylamino]-2-(2,4,6-trimethylbenzene-sulfonylamino)propionic acid,
3-[1-[3-(pyridin-2-ylamino)propyl]indazol-4-yl-carbonylamino]-2-(benzenesulfonylamino)-propionic acid,
3-[1-[3-(pyridin-2-ylamino)propyl]indazol-4-yl-carbonylamino]-2-(2,6-dichlorobenzene-sulfonylamino) propionic acid,
3-[1-[3-(pyridin-2-ylamino)propyl]indazol-4-yl-carbonylamino]-2-(3,5-dimethylisoxazol-4-ylsulfonylamino)propionic acid,
3-[1-[3-(pyridin-2-ylamino)propyl]indazol-4-yl-carbonylamino]-2-(2,6-dimethylbenzene-sulfonylamino) propionic acid,
3-[1-[3-(pyridin-2-ylamino)propyl]indazol-4-yl-carbonylamino]-2-(2,6-dimethyl-4-phenyl-benzenesulfonylamino)propionic acid, and
3-[1-[3-(pyridin-2-ylamino)propyl]indazol-4-yl-carbonylamino]-2-(4-phenylbenzenesulfonyl-amino) propionic acid.

6. A pharmaceutical composition comprising a compound of claim 1 and a pharmaceutically acceptable carrier.

7. A pharmaceutical composition comprising a compound of claim 2 and a pharmaceutically acceptable carrier.

8. A pharmaceutical composition comprising a compound of claim 3 and a pharmaceutically acceptable carrier.

9. A pharmaceutical composition comprising a compound of claim 4 and a pharmaceutically acceptable carrier.

10. A pharmaceutical composition comprising a compound of claim 5 and a pharmaceutically acceptable carrier.

11. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 1 by iontophoresis.

12. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 2 by iontophoresis.

13. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 3 by iontophoresis.

14. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 4 by iontophoresis.

15. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 5 by iontophoresis.

16. A compound of Formula Ib:

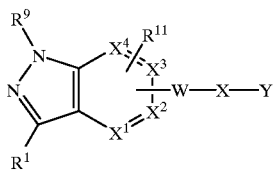

including stereoisomeric forms thereof, or mixtures of stereoisomeric forms thereof, or pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

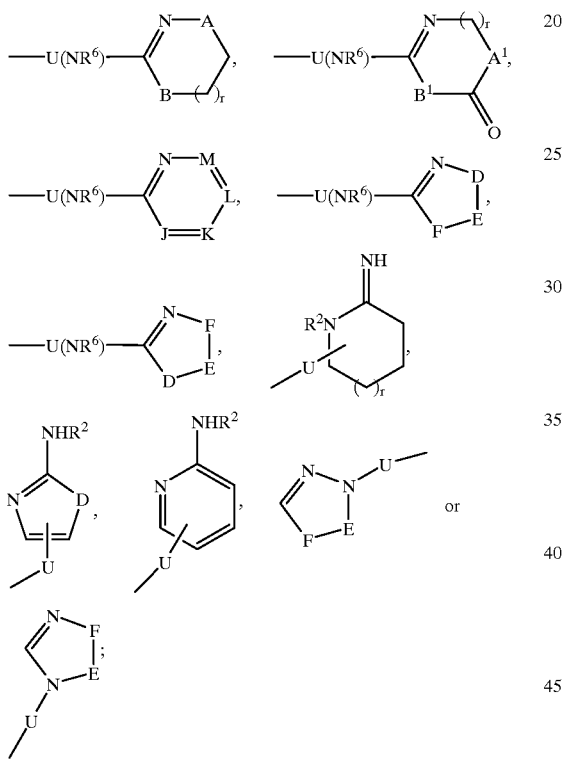

A and B are independently —$CH_2$—, —O—, —N($R^2$)—, or —C(=O)—;
$A^1$ and $B^1$ are independently —$CH_2$— or —N($R^3$)—;
D is —N($R^2$)—, —O—, —S—, —C(=O)— or —$SO_2$—;
E—F is —C($R^4$)=C($R^5$)—, —N=C($R^4$)—, —C($R^4$)=N—, or —C($R^4$)$_2$C($R^5$)$_2$—;
J, K, L and M are independently selected from: —C($R^4$)—, —C($R^5$)— or —N—, provided that at least one of J, K, L and M is not —N—;
$R^2$ is selected from: H, $C_1$–$C_6$ alkyl, ($C_1$–$C_6$ alkyl) carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl $C_1$–$C_6$ alkyl, ($C_1$–$C_6$ alkyl)carbonyl, or arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl)carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—($CH_2$)$_n$—,
—($CH_2$)$_n$($CR^7$=$CR^8$)($CH_2$)$_m$—
—($CH_2$)$_n$(C≡C)($CH_2$)$_m$—
—($CH_2$)$_t$Q($CH_2$)$_m$—
—($CH_2$)$_n$O($CH_2$)$_m$—,
—($CH_2$)$_n$N($R^6$)($CH_2$)$_m$—,
—($CH_2$)$_n$C(=O)($CH_2$)$_m$—,
—($CH_2$)$_n$(C=O)N($R^6$)($CH_2$)$_m$—
—($CH_2$)$_n$N($R^6$)(C=O)($CH_2$)$_m$—, or
—($CH_2$)$_n$S(O)$_p$($CH_2$)$_m$—;
wherein one of the methylene groups is optionally substituted with $R^7$;

Q is selected from: 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$ aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from: —(C($R^{12}$)$_2$)$_q$C(=O)N($R^{13}$)—, or —C(=O)—N($R^{13}$)—(C($R^{12}$)$_2$)$_q$—;

X is —C($R^{12}$)($R^{14}$)—C($R^{12}$)($R^{15}$)—;

$R^{12}$ is selected from: H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl ($C_1$–$C_6$ alkyl)-;

$R^{13}$ is selected from: H, $C_1$-$C_6$ alkyl, $C_3$-$C_7$ cycloalkylmethyl, or aryl($C_1$-$C_6$ alkyl)-;

$R^{14}$ is selected from: H, $C_1$-$C_6$ alkylthio($C_1$-$C_6$ alkyl)-, aryl($C_1$-$C_{10}$ alkylthioalkyl)-, aryl($C_1$-$C_{10}$ alkoxyalkyl)-, $C_1$-$C_{10}$ alkyl, $C_1$-$C_{10}$ alkoxyalkyl, $C_1$-$C_6$ hydroxyalkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl ($C_1$-$C_6$ alkyl)-, heteroaryl($C_1$-$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0-1 $R^{16}$ or 0-2 $R^{11}$;

$R^{15}$ is selected from: H, $R^{16}$, $C_1$-$C_{10}$ alkyl, $C_1$-$C_{10}$ alkoxyalkyl, $C_1$-$C_{10}$ alkylaminoalkyl, $C_1$-$C_{10}$ dialkylaminoalkyl, ($C_1$-$C_{10}$ alkyl)carbonyl, aryl ($C_0$-$C_6$ alkyl)carbonyl, $C_1$-$C_{10}$ alkenyl, $C_1$-$C_{10}$ alkynyl, $C_3$-$C_{10}$ cycloalkyl, $C_3$-$C_{10}$ cycloalkylalkyl, aryl($C_1$-$C_6$ alkyl)-, heteroaryl($C_1$-$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0-2 $R^{11}$;

Y is $-COR^{19}$;

$R^{16}$ is selected from:
  $-N(R^{20})-C(=O)-O-R^{17}$,
  $-N(R^{20})-C(=O)-R^{17}$,
  $-N(R^{20})-C(=O)-NH-R^{17}$,
  $-N(R^{20})SO_2-R^{17}$, or
  $-N(R^{20})SO_2-NR^{20}R^{17}$;

$R^{17}$ is selected from: $C_1$-$C_{10}$ alkyl, $C_3$-$C_{11}$ cycloalkyl, aryl($C_1$-$C_6$ alkyl)-, ($C_1$-$C_6$ alkyl)aryl, heteroaryl ($C_1$-$C_6$ alkyl)-, ($C_1$-$C_6$ alkyl)heteroaryl, biaryl($C_1$-$C_6$ alkyl)-, heteroaryl, or aryl, wherein said aryl or heteroaryl groups are optionally substituted with 0-3 substituents selected from the group consisting of: $C_1$-$C_4$ alkyl, $C_1$-$C_4$ alkoxy, aryl, heteroaryl, halo, cyano, amino, $CF_3$, and $NO_2$;

$R^{19}$ is $-O-(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from H, $C_1$-$C_9$ alkyl, $C_4$-$C_{11}$ cycloalkylalkyl, aryl, aryl($C_1$-$C_6$ alkyl), heteroaryl, and heteroaryl($C_1$-$C_6$ alkyl), wherein said alkyl or aryl groups are substituted with 0-2 substituents selected from the group consisting of $C_1$-$C_4$ alkyl, $C_1$-$C_4$ alkoxy, OH, halo, $CF_3$, and nitro; alternatively $R^{22}$ and $R^{23}$ can be taken together to form a 5-7 membered heterocyclic aromatic or non-aromatic ring system containing 1-3 heteroatoms selected from N, O and S and $R^{24}$ is defined as above or $R^{22}$, $R^{23}$, and $R^{24}$ can be taken together to form a heterobicyclic ring system containing 1-3 heteroatoms selected from N, O and S, wherein said heterocyclic or heterobicyclic ring being optionally substituted with 0-2 groups selected from $C_1$-$C_4$ alkyl, $C_1$-$C_4$ alkoxy, halo, cyano, amino, $CF_3$, and $NO_2$;

$R^{20}$ is selected from: H, $C_1$-$C_6$ alkyl, $C_3$-$C_7$ cycloalkyl, $C_4$-$C_{11}$ cycloalkylalkyl, aryl, aryl($C_1$-$C_6$ alkyl)-, or heteroaryl($C_1$-$C_6$ alkyl)-;

$R^{21}$ is selected from: COOH or $NR^6_2$; and k is 2, 3, 4, 5, or 6;

m is 0, 1, 2, 3, or 4;

n is 0, 1, 2, 3, or 4;

t is 0, 1, 2, 3, or 4;

p is 0, 1, or 2;

q is 0, 1, or 2; and r is 0, 1, or 2;

with the following provisos:
  (1) t, n, m and q are chosen such that the number of atoms connecting $R^1$ and Y is in the range of 10-14; and
  (2) n and m are chosen such that the value of n plus m is greater than one unless U is $-(CH_2)_nQ(CH_2)_m-$.

17. A compound of claim 16 of Formula Ib:

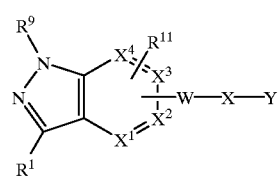

Ib including stereoisomeric forms thereof, or mixtures of stereoisomeric forms thereof, or pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

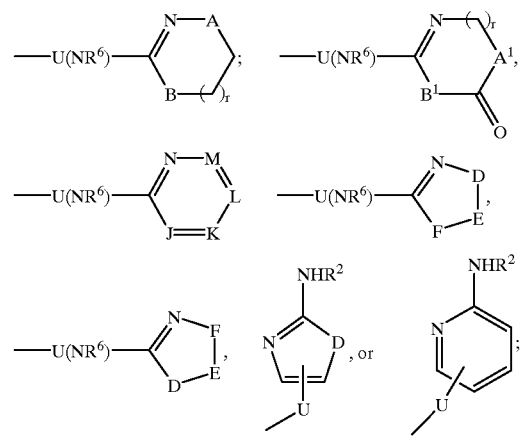

A and B are independently $-CH_2-$, $-O-$, $-N(R^2)-$, or $-C(=O)-$;

$A^1$ and $B^1$ are independently $-CH_2-$ or $-N(R^3)-$;

D is $-N(R^2)-$, $-O-$, $-S-$, $-C(=O)-$ or $-SO_2-$;

E-F is $-C(R^4)=C(R^5)-$, $-N=C(R^4)-$, $-C(R^4)=N-$, or $-C(R^4)_2C(R^5)_2-$;

J, K, L and M are independently selected from $-C(R^4)-$, $-C(R^5)-$ or $-N-$, provided that at least one of J, K, L and M is not $-N-$;

$R^2$ is selected from: H, $C_1$-$C_6$ alkyl, ($C_1$-$C_6$ alkyl) carbonyl, ($C_1$-$C_6$ alkoxy)carbonyl, $C_1$-$C_6$ alkylaminocarbonyl, $C_3$-$C_6$ alkenyl, $C_3$-$C_7$ cycloalkyl, $C_4$-$C_{11}$ cycloalkylalkyl, aryl, heteroaryl ($C_1$-$C_6$ alkyl)carbonyl, heteroarylcarbonyl, aryl ($C_1$-$C_6$ alkyl)-, ($C_1$-$C_6$ alkyl)carbonyl, arylcarbonyl, alkylsulfonyl, arylsulfonyl, aryl($C_1$-$C_6$ alkyl) sulfonyl, heteroarylsulfonyl, heteroaryl($C_1$-$C_6$ alkyl)sulfonyl, aryloxycarbonyl, aryl($C_1$-$C_6$ alkoxy) carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7$=$CR^8)(CH_2)_m$—
—$(CH_2)_tQ(CH_2)_m$—,
—$(CH_2)_nO(CH_2)_m$—,
—$(CH_2)_nN(R^6)(CH_2)_m$—,
—$(CH_2)_nC$(=O)$(CH_2)_m$—, or
—$(CH_2)_nS(O)_p(CH_2)_m$—;
wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C$(=O)$R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$ aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —$C$(=O)—$N(R^{13})$—$(C(R^{12})_2)_q$—;

X is —$C(R^{12})(R^{14})$—$C(R^{12})(R^{15})$—;

$R^{12}$ is H or $C_1$–$C_6$ alkyl;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from: H, $C_1$–$C_6$ alkylthioalkyl, aryl ($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C$(=O)$R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C$(=O)$R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is —$COR^{19}$;

$R^{16}$ is selected from:
—$N(R^{20})$—$C$(=O)—O—$R^{17}$,
—$N(R^{20})$—$C$(=O)—$R^{17}$,
—$N(R^{20})$—$C$(=O)—NH—$R^{17}$,
—$N(R^{20})SO_2$—$R^{17}$, or
—$N(R^{20})SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from H, $C_1$–$C_6$ alkyl, $C_4$–$C_{11}$ cycloalkylalkyl, aryl, aryl($C_1$–$C_6$ alkyl), heteroaryl, and heteroaryl($C_1$–$C_6$ alkyl), wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from: COOH or $NR^6_2$;

k is 2–4;

m is 0–4;

n is 0–4;

t is 0–4;

p is 0–2;

q is 0–2; and r is 0–2.

18. A compound of claim 16 of the Formula IIc or IId:

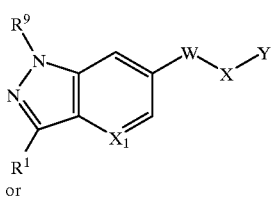

IIc or

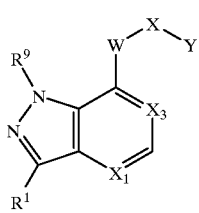

IId including stereoisomeric forms thereof, or mixtures of stereoisomeric forms thereof, or pharmaceutically acceptable salt forms thereof, wherein:

$X_1$ and $X_3$ are independently selected from nitrogen or carbon;

$R^1$ is selected from:

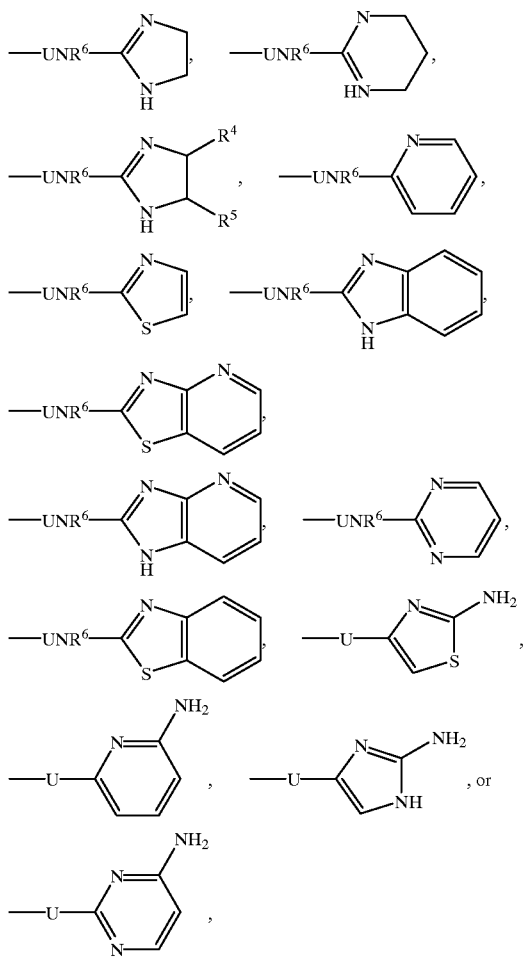

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_nQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH ($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—N($R^{20}$)$R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, $C_1$–$C_4$ alkyl, and $C_4$–$C_{11}$ cycloalkylalkyl;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{20}$ is H or $CH_3$;

$R^{21}$ is selected from COOH or $NR^6_2$;

k is 2;

m is 0 or 1;

n is 1–4; and t is 0 or 1.

19. A compound of claim 16 of the Formula IIc or IId:

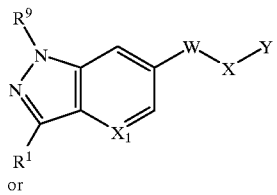   IIc or

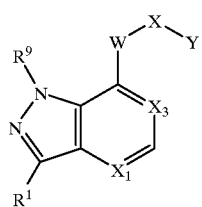   IId including stereoisomeric forms thereof, or mixtures of stereoisomeric forms thereof, or pharmaceutically acceptable salt forms thereof, wherein:

$X_1$ and $X_3$ are independently selected from nitrogen or carbon, provided that at least one of $X_1$ and $X_3$ is carbon;

$R^1$ is selected from:

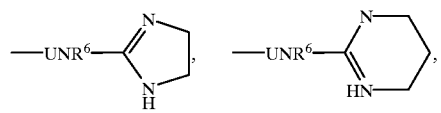

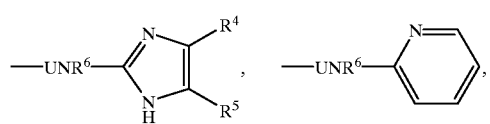

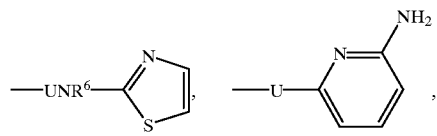

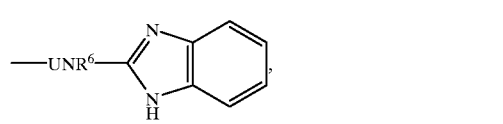

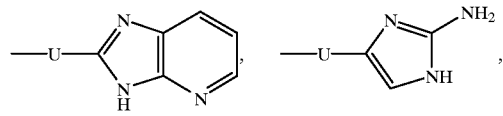

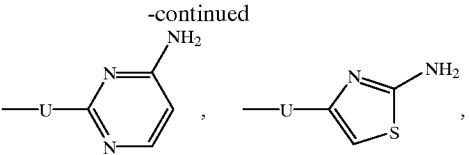

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl:

U is —$(CH_2)_n$—, —$(CH_2)_tQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_{1-6}$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—N($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from: $C_1$–$C_{10}$ alkyl, $C_3$–$C_{11}$cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, methyl, ethyl, propyl and butyl;

alternatively $R^{22}$ and $R^{23}$ can be taken together to form a 5–7 membered heterocyclic ring system containing 1–2 heteroatoms selected from N, O and S and $R^{24}$ is defined as above;

$R^{20}$ is H or $CH_3$;

$R^{21}$ is selected from COOH or $NR^6{}_2$; and k is 2;

m is 0 or 1;

n is 1–4; and t is 0 or 1.

20. An ammonium ester compound of claim 16 of Formula Ib, including enantiomeric forms, diasteriomeric forms or mixtures of enantiomeric or diasteriomeric forms thereof, and pharmaceutically acceptable salt forms thereof, wherein:

the alkyl ammonium component in the ester group of $R^{19}$ is selected from:

(trimethylammonium)ethyl,
(triethylammonium)ethyl,
(diethylmethylammonium)ethyl,
(1-morpholinomethylammonium)ethyl,
(1-morpholinoethylammonium)ethyl,
(1-pyrrolidinomethylammonium)ethyl, and
(1-pyrrolidinoethylammonium)ethyl; and the acid component of the compound is selected from:

3-[3-[3-(imidazolin-2-ylamino)propyl]indazol-6-ylcarbonylamino]-2-(benzyloxycarbonylamino)-propionic acid, 3-[1-methyl-3-[3-(imidazolin-2-ylamino)propyl]-indazol-6-ylcarbonylamino]-2-(2,4,6-trimethyl-benzenesulfonylamino)propionic acid, 3-[3-[3-(imidazolin-2-ylamino)propyl]indazol-6-ylcarbonylamino]-2-(benzenesulfonylamino)propionic acid, 3-[1-methyl-3-[3-(imidazolin-2-ylamino)propyl]-indazol-6-ylcarbonylamino]-2-(2,6-dichloro-benzenesulfonylamino)propionic acid, 3-[3-[3-(imidazolin-2-ylamino)propyl]indazol-6-ylcarbonylamino]-2-(3,5-dimethylisoxazol-4-ylsulfonylamino)propionic acid, 3-[1-methyl-3-[3-(imidazolin-2-ylamino)propyl]-indazol-6-ylcarbonyl amino]-2-(2,6-dimethyl-benzenesulfonylamino)propionic acid, 3-[3-[3-(imidazolin-2-ylamino)propyl]indazol-6-ylcarbonylamino]-2-(2,6-dimethyl-4-phenyl-benzenesulfonylamino)propionic acid, 3-[1-methyl-3-[3-(imidazolin-2-ylamino)propyl]-indazol-6-ylcarbonyl amino]-2-(4-phenylbenzene-sulfonylamino) propionic acid, 3-[3-[3-(tetrahydropyrimid-2-ylamino)propyl]-indazol-6-ylcarbonylamino]-2-(benzyloxy-carbonylamino) propionic acid, 3-[1-methyl-3-[3-(tetrahydropyrimid-2-ylamino)propyl] indazol-6-ylcarbonylamino]-2-(2,4,6-trimethylbenzenesulfonylamino)propionic acid, 3-[3-[3-(tetrahydropyrimid-2-ylamino)propyl]-indazol-6-ylcarbonylamino]-2-(benzenesulfonyl-amino)propionic acid, 3-[1-methyl-3-[3-(tetrahydropyrimid-2-ylamino)propyl] indazol-6-ylcarbonylamino]-2-(2,6-dichlorobenzenesulfonylamino)propionic acid, 3-[3-[3-(tetrahydropyrimid-2-ylamino)propyl]-indazol-6-ylcarbonylamino]-2-(3,5-dimethyl-isoxazol-4-ylsulfonylamino)propionic acid, 3-[1-methyl-3-[3-(tetrahydropyrimid-2-ylamino)propyl] indazol-6-ylcarbonylamino]-2-(2,6-dimethylbenzenesulfonylamino)propionic acid, 3-[3-[3-(tetrahydropyrimid-2-ylamino)propyl]-indazol-6-ylcarbonylamino]-2-(2,6-dimethyl-4-phenylbenzenesulfonylamino)propionic acid, 3-[1-methyl-3-[3-(tetrahydropyrimid-2-ylamino)-propyl]-indazol-6-ylcarbonylamino]-2-(4-phenylbenzenesulfonylamino)propionic acid, 3-[3-[3-(imidazol-2-ylamino)propyl]indazol-6-yl-carbonylamino]-2-(benzyloxycarbonylamino)-propionic acid, 3-[1-methyl-3-[3-(imidazol-2-ylamino)propyl]-indazol-6-ylcarbonylamino]-2-(2,4,6-trimethyl-benzenesulfonylamino)propionic acid, 3-[3-[3-(imidazol-2-ylamino)propyl]indazol-6-yl-carbonylamino]-2-(benzenesulfonylamino)-propionic acid, 3-[1-methyl-3-[3-(imidazol-2-ylamino)propyl]-indazol-6-ylcarbonylamino]-2-(2,6-dichloro-benzenesulfonylamino)propionic acid, 3-[3-[3-(imidazol-2-ylamino)propyl]indazol-6-yl-carbonylamino]-2-(3,5-dimethylisoxazol-4-ylsulfonylamino)propionic acid, 3-[1-methyl-3-[3-(imidazol-2-ylamino)propyl]-indazol-6-ylcarbonyl amino]-2-(2,6-dimethyl-benzenesulfonylamino)propionic acid, 3-[3-[3-(imidazol-2-ylamino)propyl]indazol-6-yl-carbonylamino]-2-(2,6-dimethyl-4-phenyl-benzenesulfonylamino)propionic acid, 3-[1-methyl-3-[3-(imidazol-2-ylamino)propyl]-indazol-6-ylcarbonylamino]-2-(4-phenylbenzene-sulfonylamino) propionic acid, 3-[3-[3-(pyridin-2-ylamino)propyl]indazol-6-yl-carbonylamino]-2-(benzyloxycarbonylamino)-propionic acid, 3-[1-methyl-3-[3-(pyridin-2-ylamino)propyl]indazol-6-ylcarbonylamino]-2-(2,4,6-trimethylbenzene-sulfonylamino)propionic acid, 3-[3-[3-(pyridin-2-ylamino)propyl]indazol-6-yl-carbonylamino]-2-(benzenesulfonylamino)-propionic acid, 3-[1-methyl-3-[3-(pyridin-2-ylamino)propyl]indazol-6-ylcarbonylamino]-2-(2,6-dichlorobenzene-sulfonylamino)propionic acid, 3-[3-[3-(pyridin-2-ylamino)propyl]indazol-6-yl-carbonylamino]-2-(3,5-dimethylisoxazol-4-ylsulfonylamino)propionic acid, 3-[1-methyl-3-[3-(pyridin-2-ylamino)propyl]indazol-6-ylcarbonylamino]-2-(2,6-dimethylbenzene-sulfonylamino)propionic acid, 3-[3-[3-(pyridin-2-ylamino)propyl]indazol-6-yl-carbonylamino]-2-(2,6-dimethyl-4-phenyl-benzenesulfonylamino)propionic acid, 3-[1-methyl-3-[3-(pyridin-2-ylamino)propyl]indazol-6-ylcarbonylamino]-2-(4-phenylbenzenesulfonylamino) propionic acid, 3-[3-[3-(imidazolin-2-ylamino)propyl]indazol-7-ylcarbonylamino]-2-(benzyloxycarbonylamino)-propionic acid, 3-[1-methyl-3-[3-(imidazolin-2-ylamino)propyl]-indazol-7-ylcarbonylamino]-2-(2,4,6-trimethylbenzenesulfonylamino)propionic acid, 3-[3-[3-(imidazolin-2-ylamino)propyl]indazol-7-ylcarbonylamino]-2-(benzenesulfonylamino)propionic acid, 3-[1-methyl-3-[3-(imidazolin-2-ylamino)propyl]-indazol-7-ylcarbonylamino]-2-(2,6-dichlorobenzenesulfonylamino)propionic acid, 3-[3-[3-(imidazolin-2-ylamino)propyl]indazol-7-ylcarbonylamino]-2-(3,5-dimethylisoxazol-4-ylsulfonylamino)propionic acid, 3-[1-methyl-3-[3-(imidazolin-2-ylamino)propyl]-indazol-7-ylcarbonylamino]-2-(2,6-dimethylbenzenesulfonylamino)propionic acid, 3-[3-[3-(imidazolin-2-ylamino)propyl]indazol-7-ylcarbonylamino]-2-(2,6-dimethyl-4-phenylbenzenesulfonylamino)propionic acid, 3-[1-methyl-3-[3-(imidazolin-2-ylamino)propyl]-indazol-7-ylcarbonylamino]-2-(4-phenylbenzenesulfonylamino)propionic acid, 3-[3-[3-(tetrahydropyrimid-2-ylamino)propyl]-indazol-7-ylcarbonylamino]-2-(benzyloxy-carbonylamino)propionic acid, 3-[1-methyl-3-[3-(tetrahydropyrimid-2-ylamino)propyl]indazol-7-ylcarbonylamino]-2-(2,4,6-trimethylbenzenesulfonylamino)propionic acid, 3-[3-[3-(tetrahydropyrimid-2-ylamino)propyl]-indazol-7-ylcarbonylamino]-2-(benzenesulfonyl-amino)propionic acid, 3-[1-methyl-3-[3-(tetrahydropyrimid-2-ylamino)propyl]indazol-7-ylcarbonylamino]-2-(2,6-dichlorobenzenesulfonylamino)propionic acid, 3-[3-[3-(tetrahydropyrimid-2-ylamino)propyl]-indazol-7-ylcarbonylamino]-2-(3,5-dimethyl-isoxazol-4-ylsulfonylamino)propionic acid, 3-[1-methyl-3-[3-(tetrahydropyrimid-2-ylamino)propyl]indazol-7-ylcarbonylamino]-2-(2,6-dimethylbenzenesulfonylamino)propionic acid, 3-[3-[3-(tetrahydropyrimid-2-ylamino)propyl]-indazol-7-ylcarbonylamino]-2-(2,6-dimethyl-4-phenylbenzenesulfonylamino)propionic acid, 3-[1-methyl-3-[3-(tetrahydropyrimid-2-ylamino)propyl]indazol-7-ylcarbonylamino]-2-(4-phenylbenzenesulfonylamino)propionic acid, 3-[3-[3-(imidazol-2-ylamino)propyl]indazol-7-ylcarbonylamino]-2-(benzyloxycarbonylamino)-propionic acid, 3-[1-methyl-3-[3-(imidazol-2-ylamino)propyl]-indazol-7-ylcarbonylamino]-2-(2,4,6-trimethylbenzenesulfonylamino)propionic acid, 3-[3-[3-(imidazol-2-ylamino)propyl]indazol-7-ylcarbonylamino]-2-(benzenesulfonylamino)-propionic acid, 3-[1-methyl-3-[3-(imidazol-2-ylamino)propyl]-indazol-7-ylcarbonylamino]-2-(2,6-dichlorobenzenesulfonylamino)propionic acid, 3-[3-[3-(imidazol-2-ylamino)propyl]indazol-7-ylcarbonylamino]-2-(3,5-dimethylisoxazol-4-ylsulfonylamino)propionic acid, 3-[1-methyl-3-[3-(imidazol-2-ylamino)propyl]-indazol-7-ylcarbonylamino]-2-(2,6-dimethylbenzenesulfonylamino)propionic acid, 3-[3-[3-(imidazol-2-ylamino)propyl]indazol-7-ylcarbonylamino]-2-(2,6-dimethyl-4-phenylbenzenesulfonylamino)propionic acid, 3-[1-methyl-3-[3-(imidazol-2-ylamino)propyl]-indazol-7-ylcarbonylamino]-2-(4-phenylbenzenesulfonylamino)propionic acid, 3-[3-[3-(pyridin-2-ylamino)propyl]indazol-7-ylcarbonylamino]-2-(benzyloxycarbonylamino)-propionic acid, 3-[1-methyl-3-[3-(pyridin-2-ylamino)propyl]indazol-7-ylcarbonylamino]-2-(2,4,6-trimethylbenzenesulfonylamino)propionic acid, 3-[3-[3-(pyridin-2-ylamino)propyl]indazol-7-ylcarbonylamino]-2-(benzenesulfonylamino)-propionic acid, 3-[1-methyl-3-[3-(pyridin-2-ylamino)propyl]indazol-7-ylcarbonylamino]-2-(2,6-dichlorobenzenesulfonylamino)propionic acid, 3-[3-[3-(pyridin-2-ylamino)propyl]indazol-7-ylcarbonylamino]-2-(3,5-dimethylisoxazol-4-ylsulfonylamino)propionic acid, 3-[1-methyl-3-[3-(pyridin-2-ylamino)propyl]indazol-7-ylcarbonylamino]-2-(2,6-dimethylbenzenesulfonylamino)propionic acid, 3-[3-[3-(pyridin-2-ylamino)propyl]indazol-7-ylcarbonylamino]-2-(2,6-dimethyl-4-phenylbenzenesulfonylamino)propionic acid, and 3-[1-methyl-3-[3-(pyridin-2-ylamino)propyl]indazol-7-ylcarbonylamino]-2-(4-phenylbenzenesulfonylamino)propionic acid.

21. A pharmaceutical composition comprising a compound of claim 16 and a pharmaceutically acceptable carrier.

22. A pharmaceutical composition comprising a compound of claim 17 and a pharmaceutically acceptable carrier.

23. A pharmaceutical composition comprising a compound of claim 18 and a pharmaceutically acceptable carrier.

24. A pharmaceutical composition comprising a compound of claim 19 and a pharmaceutically acceptable carrier.

25. A pharmaceutical composition comprising a compound of claim 20 and a pharmaceutically acceptable carrier.

26. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 16 by iontophoresis.

27. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 17 by iontophoresis.

28. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 18 by iontophoresis.

29. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 19 by iontophoresis.

30. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 20 by iontophoresis.

31. A compound of Formula Ic:

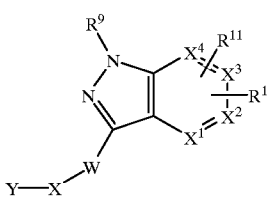

including stereoisomeric forms thereof, or mixtures of stereoisomeric forms thereof, or pharmaceutically acceptable salt forms, thereof wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

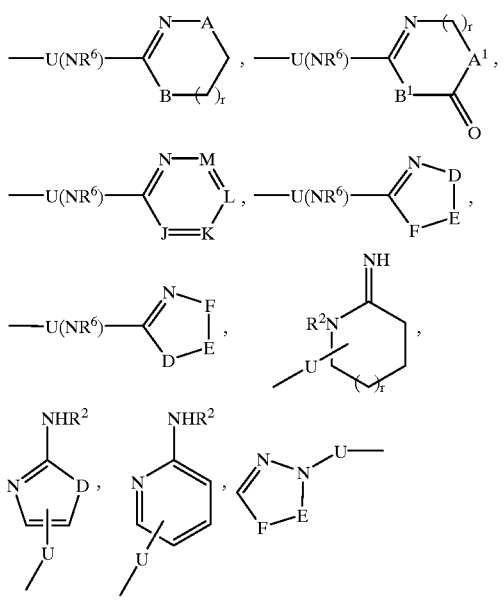

or

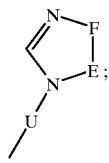

A and B are independently —CH$_2$—, —O—, —N(R$^2$)—, or —C(=O)—;
A$^1$ and B$^1$ are independently —CH$_2$— or —N(R$^3$)—;
D is —N(R$^2$)—, —O—, —S—, —C(=O)— or —SO$_2$—;
E—F is —C(R$^4$)=C(R$^5$)—, —N=C(R$^4$)—, —C(R$^4$)=N—, or —C(R$^4$)$_2$C(R$^5$)$_2$—;
J, K, L and M are independently selected from —C(R$^4$)—, —C(R$^5$)— or —N—, provided that at least one of J, K, L and M is not —N—;
R$^2$ is selected from: H, C$_1$–C$_6$ alkyl, (C$_1$–C$_6$ alkyl)carbonyl, (C$_1$–C$_6$ alkoxy)carbonyl; (C$_1$–C$_6$ alkyl)aminocarbonyl, C$_3$–C$_6$ alkenyl, C$_3$–C$_7$ cycloalkyl, C$_4$–C$_{11}$ cycloalkylalkyl, aryl, heteroaryl(C$_1$–C$_6$ alkyl)carbonyl, heteroarylcarbonyl, aryl C$_1$–C$_6$ alkyl, (C$_1$–C$_6$ alkyl)carbonyl, or arylcarbonyl, C$_1$–C$_6$ alkylsulfonyl, arylsulfonyl, aryl(C$_1$–C$_6$ alkyl)sulfonyl, heteroarylsulfonyl, heteroaryl(C$_1$–C$_6$ alkyl)sulfonyl, aryloxycarbonyl, or aryl(C$_1$–C$_6$ alkoxy)carbonyl, wherein said aryl groups are substituted with 0–2 substituents selected from the group consisting of C$_1$–C$_4$ alkyl, C$_1$–C$_4$ alkoxy, halo, CF$_3$, and nitro;

R$^3$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_1$–C$_6$ alkyl)-;

R$^4$ and R$^5$ are independently selected from: H, C$_1$–C$_4$ alkoxy, NR$^2$R$^3$, halogen, NO$_2$, CN, CF$_3$, C$_1$–C$_6$ alkyl, C$_3$–C$_6$ alkenyl, C$_3$–C$_7$ cycloalkyl, C$_4$–C$_{11}$cycloalkylalkyl, aryl, aryl(C$_1$–C$_6$ alkyl)-, (C$_1$–C$_6$ alkyl)carbonyl, (C$_1$–C$_6$ alkoxy)carbonyl, arylcarbonyl, or alternatively, when substituents on adjacent atoms, R$^4$ and R$^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: C$_1$–C$_4$ alkyl, C$_1$–C$_4$ alkoxy, halo, cyano, amino, CF$_3$, or NO$_2$;

U is selected from:
—(CH$_2$)$_n$—,
—(CH$_2$)$_n$(CR$^7$=CR$^8$)(CH$_2$)$_m$—
—(CH$_2$)$_n$(C≡C)(CH$_2$)$_m$—
—(CH$_2$)$_t$Q(CH$_2$)$_m$—
—(CH$_2$)$_n$O(CH$_2$)$_m$—,
—(CH$_2$)$_n$N(R$^6$)(CH$_2$)$_m$—,
—(CH$_2$)$_n$C(=O)(CH$_2$)$_m$—,
—(CH$_2$)$_n$(C=O)N(R$^6$)(CH$_2$)$_m$—
—(CH$_2$)$_n$N(R$^6$)(C=O)(CH$_2$)$_m$—, or
—(CH$_2$)$_n$S(O)$_p$(CH$_2$)$_m$—;
wherein one of the methylene groups is optionally substituted with R$^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

R$^6$ is selected from: H, C$_1$–C$_4$ alkyl, or benzyl;
R$^7$ and R$^8$ are independently selected from: H, C$_1$–C$_6$ alkyl, C$_3$–C$_7$ cycloalkyl, C$_4$–C$_{11}$cycloalkylalkyl, aryl, aryl(C$_1$–C$_6$ alkyl)-, or heteroaryl(C$_0$–C$_6$ alkyl)-;

R$^9$ is selected from: H, CO$_2$R$^{17}$, C(=O)R$^{17}$, CONR$^{17}$R$^{20}$, —SO$_2$R$^{17}$, —SO$_2$NR$^{17}$R$^{20}$, C$_1$–C$_6$ alkyl substituted with 0–1 R$^{15}$ or 0–1 R$^{21}$, C$_3$–C$_6$ alkenyl substituted with 0–1 R$^{15}$ or 0–1 R$^{21}$, C$_3$–C$_7$ cycloalkyl substituted with 0–1 R$^{15}$ or 0–1 R$^{21}$, C$_4$–C$_{11}$ cycloalkylalkyl substituted with 0–1 R$^{15}$ or 0–1 R$^{21}$, aryl substituted with 0–1 R$^{15}$ or 0–2 R$^{11}$ or 0–1 R$^{21}$, or aryl(C$_1$–C$_6$ alkyl)- substituted with 0–1 R$^{15}$ or 0–2 R$^{11}$ or 0–1 R$^{21}$;

R$^{11}$ is selected from H, halogen, CF$_3$, CN, NO$_2$, hydroxy, NR$^2$R$^3$, C$_1$–C$_4$ alkyl substituted with 0–1 R$^{21}$, C$_1$–C$_4$ alkoxy substituted with 0–1 R$^{21}$, aryl substituted with 0–1 R$^{21}$, aryl(C$_1$–C$_6$ alkyl)- substituted with 0–1 R$^{21}$, (C$_1$–C$_4$ alkoxy)carbonyl substituted with 0–1 R$^{21}$, (C$_1$–C$_4$ alkyl)carbonyl substituted with 0–1 R$^{21}$, C$_1$–C$_4$ alkylsulfonyl substituted with 0–1 R$^{21}$, or C$_1$–C$_4$ alkylaminosulfonyl substituted with 0–1 R$^{21}$;

W is selected from:
—(C(R$^{12}$)$_2$)$_q$C(=O)N(R$^{13}$)—, or
—C(=O)—N(R$^{13}$)—(C(R$^{12}$)$_2$)$_q$—;

X is —C(R$^{12}$)(R$^{14}$)—C(R$^{12}$)(R$^{15}$)—;

R$^{12}$ is selected from: H, halogen, C$_1$–C$_6$ alkyl, C$_2$–C$_6$ alkenyl, C$_2$–C$_6$ alkynyl, C$_3$–C$_7$ cycloalkyl, C$_4$–C$_{10}$ cycloalkylalkyl, (C$_1$–C$_4$ alkyl)carbonyl, aryl, or aryl (C$_1$–C$_6$ alkyl)-;

R$^{13}$ is selected from: H, C$_1$–C$_6$ alkyl, C$_3$–C$_7$ cycloalkylmethyl, or aryl(C$_1$–C$_6$ alkyl)-

R$^{14}$ is selected from: H, C$_1$–C$_6$ alkylthio(C$_1$–C$_6$ alkyl)-, aryl(C$_1$–C$_{10}$ alkylthioalkyl)-, aryl(C$_1$–C$_{10}$ alkoxyalkyl)-, C$_1$–C$_{10}$ alkyl, C$_1$–C$_{10}$ alkoxyalkyl, C$_1$–C$_6$ hydroxyalkyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl (C$_1$–C$_6$ alkyl)-, heteroaryl(C$_1$–C$_6$ alkyl)-, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be unsubstituted or substituted independently with 0–1 R$^{16}$ or 0–2 R$^{11}$;

R$^{15}$ is selected from: H, R$^{16}$, C$_1$–C$_{10}$ alkyl, C$_1$–C$_{10}$ alkoxyalkyl, C$_1$–C$_{10}$ alkylaminoalkyl, C$_1$–C$_{10}$ dialkylaminoalkyl, (C$_1$–C$_{10}$ alkyl)carbonyl, aryl (C$_0$–C$_6$ alkyl)carbonyl, C$_1$–C$_{10}$ alkenyl, C$_1$–C$_{10}$ alkynyl, C$_3$–C$_{10}$ cycloalkyl, C$_3$–C$_{10}$ cycloalkylalkyl, aryl(C$_1$–C$_6$ alkyl)-, heteroaryl(C$_1$–C$_6$ alkyl)-, aryl, heteroaryl, CO$_2$R$^{17}$, C(=O)R$^{17}$, CONR$^{17}$R$^{20}$, SO$_2$R$^{17}$, or SO$_2$NR$^{17}$R$^{20}$, provided that any of the above alkyl, cycloalkyl, aryl or heteroaryl groups may be unsubstituted or substituted independently with 0–2 R$^{11}$;

Y is —COR$^{19}$;

R$^{16}$ is selected from:
—N(R$^{20}$)—C(=O)—O—R$^{17}$,
—N(R$^{20}$)—C(=O)—R$^{17}$,
—N(R$^{20}$)—C(=O)—NH—R$^{17}$,
—N(R$^{20}$)SO$_2$—R$^{17}$, or
—N(R$^{20}$)SO$_2$—NR$^{20}$R$^{17}$;

R$^{17}$ is selected from: C$_1$–C$_{10}$ alkyl, C$_3$–C$_{11}$ cycloalkyl, aryl(C$_1$–C$_6$ alkyl)-, (C$_1$–C$_6$ alkyl)aryl, heteroaryl (C$_1$–C$_6$ alkyl)-, (C$_1$–C$_6$ alkyl)heteroaryl, biaryl(C$_1$–C$_6$ alkyl)-, heteroaryl, or aryl, wherein said aryl or heteroaryl groups are optionally substituted with 0–3 substituents selected from the group consisting of: C$_1$–C$_4$ alkyl, C$_1$–C$_4$ alkoxy, aryl, heteroaryl, halo, cyano, amino, CF$_3$, and NO$_2$;

R$^{19}$ is —O—(CH$_2$)$_k$N$^+$(R$^{22}$)(R$^{23}$)(R$^{24}$)Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{22}$, R$^{23}$ and R$^{24}$ are independently selected from H, C$_1$–C$_9$ alkyl, C$_4$–C$_{11}$ cycloalkylalkyl, aryl, aryl(C$_1$–C$_6$ alkyl), heteroaryl, and heteroaryl(C$_1$–C$_6$ alkyl), wherein said alkyl or aryl groups are substituted with 0–2 substituents selected from the group consisting of C$_1$–C$_4$ alkyl, C$_1$–C$_4$ alkoxy, OH, halo, CF$_3$, and nitro;

alternatively R$^{22}$ and R$^{23}$ can be taken together to form a 5–7 membered heterocyclic aromatic or non-aromatic ring system containing 1–3 heteroatoms selected from N, O and S and R$^{24}$ is defined as above or R$^{22}$, R$^{23}$, and R$^{24}$ can be taken together to form a heterobicyclic ring system containing 1–3 heteroatoms selected from N, O and S, wherein said heterocyclic or heterobicyclic ring being optionally substituted with 0–2 groups selected from C$_1$–C$_4$ alkyl, C$_1$–C$_4$ alkoxy, halo, cyano, amino, CF$_3$, and NO$_2$;

R$^{20}$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_1$–C$_6$ alkyl)-;

R$^{21}$ is selected from: COOH or NR$^6{}_2$; and k is 2, 3, 4, 5, or 6;
m is 0, 1, 2, 3, or 4;
n is 0, 1, 2, 3, or 4;
t is 0, 1, 2, 3, or 4;
p is 0, 1, or 2;
q is 0, 1, or 2; and
r is 0, 1, or 2;

with the following provisos:
(1) t, n, m and q are chosen such that the number of atoms connecting R$^1$ and Y is in the range of 10–14; and
(2) n and m are chosen such that the value of n plus m is greater than one unless U is —(CH$_2$)$_t$Q(CH$_2$)$_m$—.

32. A compound of claim 31 of the Formula Ic:

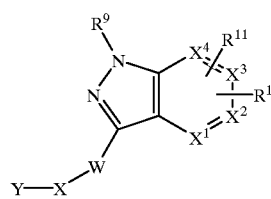

Ic including stereoisomeric forms thereof, or mixtures of stereoisomeric forms thereof, or pharmaceutically acceptable salt forms thereof wherein:

X$^1$, X$^2$, X$^3$, and X$^4$ are independently selected from nitrogen or carbon provided that at least two of X$^1$, X$^2$, X$^3$ and X$^4$ are carbon;

R$^1$ is selected from:

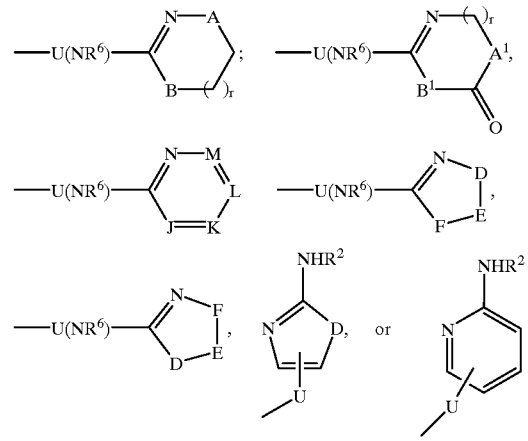

A and B are independently —CH$_2$—, —O—, —N(R$^2$)—, or —C(=O)—;
A$^1$ and B$^1$ are independently —CH$_2$— or —N(R$^3$)—;
D is —N(R$^2$)—, —O—, —S—, —C(=O)— or —SO$_2$—;
E—F is —C(R$^4$)=C(R$^5$)—, —N=C(R$^4$)—, —C(R$^4$)=N—, or —C(R$^4$)$_2$C(R$^5$)$_2$—;
J, K, L and M are independently selected from: —C(R$^4$)—, —C(R$^5$)— or —N—, provided that at least one of J, K, L and M is not —N—;
R$^2$ is selected from: H, C$_1$–C$_6$ alkyl, (C$_1$–C$_6$ alkyl) carbonyl, (C$_1$–C$_6$ alkoxy)carbonyl, C$_1$–C$_6$ alkylaminocarbonyl, C$_3$–C$_6$ alkenyl, C$_3$–C$_7$ cycloalkyl, C$_4$–C$_{11}$ cycloalkylalkyl, aryl, heteroaryl (C$_1$–C$_6$ alkyl)carbonyl, heteroarylcarbonyl, aryl (C$_1$–C$_6$ alkyl)-, (C$_1$–C$_6$ alkyl)carbonyl, arylcarbonyl, alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, aryl($C_1$–$C_6$ alkoxy) carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7=CR^8)(CH_2)_m$—
—$(CH_2)_tQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—, or
—$(CH_2)_nS(O)_p(CH_2)_m$—;
wherein one of the methylene groups is optionally substituted with $R^7$;

Q is selected from 1,2-phenylene, 1,3-phenylene, 2,3-pyridinylene, 3,4-pyridinylene, or 2,4-pyridinylene;
$R^6$ is selected from: H, $C_1$–$C_4$ alkyl, or benzyl;
$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —$C(=O)$—$N(R^{13})$—$(C(R^{12})_2)_q$—;
X is —$C(R^{12})(R^{14})$—$C(R^{12})(R^{15})$—;
$R^{12}$ is H or $C_1$–$C_6$ alkyl;
$R^{13}$ is selected from: H, $C_1$–$C_6$ alkyl, $C_3$–$C_7$ cycloalkylmethyl, or aryl($C_1$–$C_6$ alkyl)-;
$R^{14}$ is selected from: H, $C_1$–$C_6$ alkylthioalkyl, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $C_{02}R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from: H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is —$COR^{19}$;

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R^{17}$, or
—$N(R^{20})SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —$O$—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$ and $R^{24}$ are independently selected from H, $C_1$–$C_6$ alkyl, $C_4$–$C_{11}$ cycloalkylalkyl, aryl, aryl($C_1$–$C_6$ alkyl), heteroaryl, and heteroaryl($C_1$–$C_6$ alkyl), wherein said alkyl or aryl groups are substituted with 0–2 substituents selected from the group consisting of $C_1$–$C_4$ alkyl, $C_1$–$C_4$ alkoxy, OH, halo, $CF_3$, and nitro;

alternatively $R^{22}$ and $R^{23}$ can be taken together to form a 5–7 membered heterocyclic aromatic or non-aromatic ring system containing 1–3 heteroatoms selected from N, O and S and $R^{24}$ is defined as above or $R^{22}$, $R^{23}$, and $R^{24}$ can be taken together to form a heterobicyclic ring system containing 1–3 heteroatoms selected from N, O and S, wherein said heterocyclic or heterobicyclic ring being optionally substituted with 0–2 groups selected from $C_1$–$C_4$ alkyl, $C_1$–$C_4$ alkoxy, halo, cyano, amino, $CF_3$, and $NO_2$;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl) —;

$R^{21}$ is selected from: COOH or $NR^6_2$;
k is 2–4;
m is 0–4;
n is 0–4;
t is 0–4;
p is 0–2;
q is 0–2; and
r is 0–2.

33. A compound of claim 31 of the Formula IIe or IIf:

IIe

IIf including stereoisomeric forms thereof, or mixtures of stereoisomeric forms thereof, or pharmaceutically acceptable salt forms thereof, wherein:

$R^1$ is selected from:

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_rQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—N($R^{20}$)$R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is —O—$(CH_2)_kN^+(R^{22})(R^{23})(R^{24})Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{22}$, $R^{23}$, and $R^{24}$ are independently selected from H, $C_1$–$C_4$ alkyl, and $C_4$–$C_{11}$ cycloalkylalkyl;

alternatively $R^{22}$ and $R^{23}$ can be taken together to form a 5–7 membered heterocyclic ring system containing 1–2 heteroatoms selected from N, O and S and $R^{24}$ is defined as above or $R^{22}$, $R^{23}$, and $R^{24}$ can be taken together to form a heterobicyclic ring system containing 1–2 heteroatoms selected from N, O and S;

$R^{20}$ is H or $CH_3$;

$R^{21}$ is selected from COOH or $NR^6_2$;

k is 2;
m is 0 or 1;
n is 1–4; and
t is 0 or 1.

34. A compound of claim 31 of the Formula IIe or IIf:

IIe

IIf including stereoisomeric forms thereof, or mixtures of stereoisomeric forms thereof, or pharmaceutically acceptable salt forms thereof, wherein:

$R^1$ is selected from:

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl:

U is —$(CH_2)_n$—, —$(CH_2)_tQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ selected from: H, $C_1$–$C_4$ alkyl, or benzyl;

$R^7$ is selected from $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^7$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from: $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl ($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from
$Z^-$(trimethylammonium)ethyl—O—,
$Z^-$(triethylammonium)ethyl—O—,
$Z^-$(diethylmethylammonium)ethyl—O—,
$Z^-$(1-morpholinomethylammonium)ethyl—O—,
$Z^-$(1-morpholinoethylammonium)ethyl—O—,
$Z^-$(1-pyrrolidinomethylammonium)ethyl—O—, and
$Z^-$(1-pyrrolidinoethyl)ammonium)ethyl—O—;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoracetate, citrate, oxalate, succinate, and malonate;

$R^{20}$ is H or $CH_3$;

$R^{21}$ is selected from COOH or $NR^6_2$; and m is 0 or 1;
n is 1–4; and
t is 0 or 1.

35. A pharmaceutical composition comprising a compound of claim 31 and a pharmaceutically acceptable carrier.

36. A pharmaceutical composition comprising a compound of claim 32 and a pharmaceutically acceptable carrier.

37. A pharmaceutical composition comprising a compound of claim 33 and a pharmaceutically acceptable carrier.

38. A pharmaceutical composition comprising a compound of claim 34 and a pharmaceutically acceptable carrier.

39. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 31 by iontophoresis.

40. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 32 by iontophoresis.

41. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 33 by iontophoresis.

42. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 34 by iontophoresis.

* * * * *